US010035859B2

(12) United States Patent
Violette et al.

(10) Patent No.: US 10,035,859 B2
(45) Date of Patent: Jul. 31, 2018

(54) ANTI-ALPHA V BETA 6 ANTIBODIES AND USES THEREOF

(71) Applicant: Biogen MA Inc., Cambridge, MA (US)

(72) Inventors: Shelia M. Violette, Lexington, MA (US); Paul H. Weinreb, Andover, MA (US); Timothy David Jones, Babraham (GB); Francis Joseph Carr, Aberdeen (GB); Anja Sibylle Tessarz, Cambridge (GB)

(73) Assignee: Biogen MA Inc., Cambridge, MA (US)

( * ) Notice: Subject to any disclaimer, the term of this patent is extended or adjusted under 35 U.S.C. 154(b) by 42 days.

(21) Appl. No.: 14/772,512

(22) PCT Filed: Mar. 14, 2014

(86) PCT No.: PCT/US2014/028888
§ 371 (c)(1),
(2) Date: Sep. 3, 2015

(87) PCT Pub. No.: WO2014/144466
PCT Pub. Date: Sep. 18, 2014

(65) Prior Publication Data
US 2016/0031992 A1 Feb. 4, 2016

Related U.S. Application Data

(60) Provisional application No. 61/847,634, filed on Jul. 18, 2013, provisional application No. 61/790,408, filed on Mar. 15, 2013.

(51) Int. Cl.
*A61K 39/395* (2006.01)
*C07K 16/00* (2006.01)
*C07K 16/46* (2006.01)
*C07K 16/28* (2006.01)

(52) U.S. Cl.
CPC ...... *C07K 16/2839* (2013.01); *C07K 16/2842* (2013.01); *C07K 2317/24* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,683,195 A | 7/1987 | Mullis et al. |
| 4,732,863 A | 3/1988 | Tomasi et al. |
| 4,975,278 A | 12/1990 | Senter et al. |
| 5,019,368 A | 5/1991 | Epstein et al. |
| 5,208,020 A | 5/1993 | Chari et al. |
| 5,223,493 A | 6/1993 | Boltralik |
| 5,225,539 A | 7/1993 | Winter et al. |
| 5,420,120 A | 5/1995 | Boltralik |
| 5,530,101 A * | 6/1996 | Queen .......... C07K 16/00 424/133.1 |
| 5,565,332 A | 10/1996 | Hoogenboom et al. |
| 5,580,859 A | 12/1996 | Feigner et al. |
| 5,589,466 A | 12/1996 | Feigner et al. |
| 5,654,316 A | 8/1997 | Carruthers et al. |
| 5,688,960 A | 11/1997 | Shankar |
| 5,691,362 A | 11/1997 | McCormick et al. |
| 5,693,761 A | 12/1997 | Queen et al. |
| 5,696,267 A | 12/1997 | Reichard et al. |
| 5,719,156 A | 2/1998 | Shue et al. |
| 5,733,743 A | 3/1998 | Johnson et al. |
| 5,783,579 A | 7/1998 | McCormick |
| 5,789,422 A | 8/1998 | Reichard et al. |
| 5,789,650 A | 8/1998 | Lonberg et al. |
| 5,795,894 A | 8/1998 | Shue et al. |
| 5,798,359 A | 8/1998 | Shue et al. |
| 5,821,337 A | 10/1998 | Carter et al. |
| 5,827,690 A | 10/1998 | Meade et al. |
| 5,849,876 A | 12/1998 | Linsley et al. |
| 5,859,205 A | 1/1999 | Adair et al. |
| 5,869,619 A | 2/1999 | Studnicka |
| 5,892,019 A | 4/1999 | Schlom et al. |
| 5,939,598 A | 8/1999 | Kucherlapati et al. |
| 5,942,417 A | 8/1999 | Ni et al. |
| 5,962,643 A | 10/1999 | Sheppard et al. |
| 5,985,278 A | 11/1999 | Mitjans et al. |
| 6,075,181 A | 6/2000 | Kucherlapati et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,267,958 B1 | 7/2001 | Andya et al. |
| 6,291,650 B1 | 9/2001 | Winter et al. |
| 6,300,064 B1 | 10/2001 | Knappik et al. |

(Continued)

FOREIGN PATENT DOCUMENTS

| | | |
|---|---|---|
| CA | 2 355 874 | 6/2000 |
| CN | 1288469 | 3/2001 |
| EP | 239 400 | 9/1987 |
| EP | 0 719 859 | 7/1996 |
| EP | 843 961 | 5/1998 |
| JP | 2005-506331 | 3/2005 |
| JP | 2005-528099 | 9/2005 |
| WO | WO 1981/001145 | 4/1981 |
| WO | WO 1988/007378 | 10/1988 |
| WO | WO 1990/007861 | 7/1990 |

(Continued)

OTHER PUBLICATIONS

BioSpace—Print News Article, Cellmid Signs Antibody Humanisation Collaboration. pp. 1-2, (Apr. 13, 2011).*
Nash, G, ImmunoCellular Therapeutics Announces Successful Humanization of Two Antibody Candidates. pp. 1-2, Sep. 23, 2009.*

(Continued)

*Primary Examiner* — Maher M Haddad
(74) *Attorney, Agent, or Firm* — Fish & Richardson P.C.

(57) ABSTRACT

Humanized antibodies and antibody fragments thereof that bind to αvβ6 are disclosed. Also disclosed are methods of using these antibodies and antibody fragments to treat or prevent αvβ6-mediated diseases such as fibrosis and cancer.

21 Claims, 12 Drawing Sheets

(56) References Cited

U.S. PATENT DOCUMENTS

| | | | |
|---|---|---|---|
| 6,303,313 | B1 | 10/2001 | Wigler et al. |
| 6,307,026 | B1 | 10/2001 | King et al. |
| 6,358,710 | B1 | 3/2002 | Graves et al. |
| 6,692,741 | B2 | 2/2004 | Huang et al. |
| 6,787,322 | B2 | 9/2004 | Sheppard et al. |
| 6,933,368 | B2 | 8/2005 | Co et al. |
| 7,150,871 | B2 | 12/2006 | Huang et al. |
| 7,465,449 | B2 | 12/2008 | Violate et al. |
| 7,544,358 | B2 | 6/2009 | Huang et al. |
| 7,550,142 | B2 | 6/2009 | Giles-Komar et al. |
| 7,927,590 | B2 | 4/2011 | Violette et al. |
| 7,943,742 | B2 | 5/2011 | Violate et al. |
| 8,153,126 | B2 | 4/2012 | Violette et al. |
| RE44,681 | E | 12/2013 | Violette et al. |
| 2001/0056076 | A1 | 12/2001 | Huang et al. |
| 2002/0004482 | A1 | 1/2002 | Huang et al. |
| 2004/0048312 | A1 | 3/2004 | Li et al. |
| 2004/0142877 | A1 | 7/2004 | Schadt et al. |
| 2004/0253311 | A1 | 12/2004 | Berlin et al. |
| 2005/0148562 | A1 | 7/2005 | Pairet et al. |
| 2005/0255102 | A1 | 11/2005 | Violette et al. |
| 2008/0286269 | A1 | 11/2008 | Violette et al. |
| 2008/0317667 | A1 | 12/2008 | Violette et al. |
| 2009/0028853 | A1 | 1/2009 | Sheppard et al. |
| 2009/0074790 | A1 | 3/2009 | Reiss et al. |
| 2009/0186036 | A1 | 7/2009 | Violette et al. |
| 2011/0287007 | A1 | 11/2011 | Sheppard et al. |
| 2011/0293512 | A1 | 12/2011 | Violette et al. |
| 2011/0305629 | A1 | 12/2011 | Violette et al. |
| 2011/0319405 | A1 | 12/2011 | Rosen et al. |
| 2012/0014973 | A1* | 1/2012 | Naparstek ......... C07K 16/1289 424/173.1 |
| 2012/0027754 | A1 | 2/2012 | Sheppard et al. |
| 2012/0251532 | A1 | 10/2012 | Violette et al. |
| 2014/0294809 | A1 | 10/2014 | Violette et al. |
| 2015/0086570 | A1 | 3/2015 | Violette et al. |
| 2015/0140609 | A1 | 5/2015 | Violette et al. |
| 2016/0017042 | A1 | 1/2016 | Violette et al. |

FOREIGN PATENT DOCUMENTS

| | | |
|---|---|---|
| WO | WO 1991/016927 | 11/1991 |
| WO | WO 1993/021232 | 10/1993 |
| WO | WO 1994/011026 | 5/1994 |
| WO | WO 1997/006822 | 2/1997 |
| WO | WO 1999/007405 | 2/1999 |
| WO | WO 1999/037683 | 7/1999 |
| WO | WO 2001/081421 | 11/2001 |
| WO | WO 2002/012501 | 2/2002 |
| WO | WO 2002/050039 | 6/2002 |
| WO | WO 2002/083854 | 10/2002 |
| WO | WO 2003/026692 | 4/2003 |
| WO | WO 2003/072040 | 9/2003 |
| WO | WO 2003/087340 | 10/2003 |
| WO | WO 2003/097615 | 11/2003 |
| WO | WO 2003/100033 | 12/2003 |
| WO | WO 2004/056308 | 7/2004 |
| WO | WO 2005/039547 | 5/2005 |
| WO | WO 2005/044794 | 5/2005 |
| WO | WO 2007/008712 | 1/2007 |
| WO | WO 2008/008315 | 1/2008 |
| WO | WO 2008/147434 | 12/2008 |
| WO | WO 2009/103542 | 8/2009 |
| WO | WO 2010/072348 | 7/2010 |
| WO | WO 2012/031008 | 3/2012 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91.*

Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*

Perry LCA, Jones TD, Baker MP. New approaches to prediction of immune responses to therapeutic proteins during preclinical development. Drugs R D. 2008.*

Jones TD, Crompton LJ, Carr FJ, Baker MP. Deimmunization of monoclonal antibodies. Methods Mol Biol. Jan. 2009;525:405-23, xiv.*

U.S. Appl. No. 10/507,662, Issued.
U.S. Appl. No. 12/260,510, Issued.
U.S. Appl. No. 13/443,261, Abandoned.
U.S. Appl. No. 14/444,701, Pending.
U.S. Appl. No. 11/483,190, Issued.
U.S. Appl. No. 13/109,168, Issued.
U.S. Appl. No. 14/161,207, Published.
U.S. Appl. No. 11/822,859, Issued.
U.S. Appl. No. 13/088,774, Abandoned.
U.S. Appl. No. 11/872,876, Abandoned.
U.S. Appl. No. 13/204,382, Abandoned.
U.S. Appl. No. 13/204,420, Abandoned.
U.S. Appl. No. 13/713,588, Abandoned.
U.S. Appl. No. 14/387,762, Published.
U.S. Appl. No. 14/772,863, Published.

Kowal-Bielecka et al., "Cyclooxygenase- and Lipoxygenase-Derived Eicosanoids in Bronchoalveolar Lavage Fluid From Patients With Scleroderma Lung Disease," Arthritis & Rheumatism, 52(12):3783-3791 (Dec. 2005).

Schnell et al., "Endothelin-1 Induces LOX-1 Expression Fibroblasts and Venous Endothelial Cells of Lungs In Vitro: Effects of Bosetan, B60, Pulmonary Fibrosis: The Fibroblast," American Journal of Respiratory and Critical Care Medicine, Meeting Abstracts American Thoracic Society, 2009, International Conference, May 15-20, 2009, San Diego, California, 1 page.

Violette et al., "Identification of biomarkers to monitor the activity of STX-100, a humanized anti-αvβ6 antibody, in a phase 2A trial in idiopathic pulmonary fibrosis," American Journal of Respiratory and Critical Care Medicine, 185:A2659 (May 2012), Abstract 2 pages.

Zhang et al., "Blockade of LOX-1 Prevents Endotoxin-Induced Acute Lung Inflammation and Injury in Mice," J Innate Immun., 1:358-365 (Oct. 2008).

Minami et al., "Transforming growth factor-b1 increases the expression of Lectin-like oxidized low-density lipoprotein receptor-1," Biochemical and Biophysical Research Communications 272, 357-361 (2000).

Varga et al., "Transforming growth factor β as a therapeutic target in systemic sclerosis," Nat Rev. Rheumatol., Apr. 2009;5(4):200-206.

Abe et al., "An Assay for Transforming Growth Factor-β Using Cells Transfected with a Plasminogen Activator Inhibitor-1 Promoter-Luciferase Construct[1]," Anal Biochem, 216(2):276-284, 1994.

Agrez et al., "The αvβ6 Integrin Promotes Proliferation of Colon Carcinoma Cells through a Unique Region of the β6 Cytoplasmic Domain," J Cell Biol, 127(2):547-556, Oct. 1994.

Agrez et al., "The αvβ6 integrin induces gelatinase B secretion in colon cancer cells," Int. J Cancer, 81(1):90-97, 1999.

Ahmed et al., "Overexpression of αvβ6 integrin in serous epithelial ovarian cancer regulates extracellular matrix degradation via the plasminogen activation cascade," Carcinogenesis, 23(2):237-244, Feb. 2002.

Ahmed et al., "αvβ6 integrin—A marker for the malignant potential of epithelial ovarian cancer," J Histochem Cytochem, 50(10):1371-1380, Oct. 2002.

Akhurst et al., "TGF-β signaling in cancer—a double-edged sword," Trends Cell Biol, 11(11):S44-S51, Nov. 2001.

Akhurst, "TGF-β antagonists: why suppress a tumor suppressor?," J Clin Invest., 109(12):1533-1536, Jun. 2002.

Albelda, "Role of integrins and other cell adhesion molecules in tumor progression and metastasis," Lab Invest, 68(1):4-17, Jan. 1993.

(56) References Cited

OTHER PUBLICATIONS

Aluwihare et al., "Mice that lack activity of αvβ6- and αvβ8-integrins reproduce the abnormalities of Tgfb1- and Tgfb3-null mice," J Cell Sci, 122(Pt 2):227-32, 2009.
Annes et al., "Making sense of latent TGFβ activation," J Cell Sci, 116(Pt 2):217-224, 2003.
Araya et al., "Integrin-mediated transforming growth factor-β activation regulates homeostasis of the pulmonary epithelial-mesenchymal trophic unit," Am J Pathol, 169(2):405-415, Aug. 2006.
Arend et al., "Mouse β6 integrin sequence, pattern of expression, and role in kidney development," J Am Soc Nephrol, 11(12):2297-2305, 2000.
Baraldo et al., "Decreased expression of TGF-β type II receptor in bronchial glands of smokers with COPD," Thorax, 60:998-1002, Oct. 2005.
Barcellos-Hoff et al., "Immunohistochemical detection of active transforming growth factor-β in situ using engineered tissue," Am J Pathol, 147(5):1228-1237, Nov. 1995.
Barcellos-Hoff, "Latency and activation in the control of TGF-β," J Mammary Gland Biol Neoplasia, 1(4):353-363, Oct. 1996.
Bates and Mercurio, "Tumor necrosis factor-α stimulates the epithelial-to-mesenchymal transition of human colonic organoids," Mol Biol Cell, 14(5):1790-1800, May 2003.
Bates et al., "Transcriptional activation of integrin β6 during the epithelial-mesenchymal transition defines a novel prognostic indicator of aggressive colon carcinoma," J Clin Invest, 115(2):339-347, Feb. 2005.
Beiboer et al., "Guided selection of a pan carcinoma specific antibody reveals similar binding characteristics yet structural divergence between the original murine antibody and its human equivalent," J Mol. Biol, 296:833-849, 2000.
Bendig, "Humanization of Rodent Monoclonal Antibodies by CDR Grafting," METHODS: a Companion to Methods in Enzymology, 8:83-93, 1995.
Blobe et al., "Role of transforming growth factor β in human disease," N Engl J Med, 342:1350-1358, May 4, 2000.
Bodey et al., "Failure of cancer vaccines: the significant limitations of this approach to immunotherapy," Anticancer Res, 20:2665-2676, 2000.
Bodey et al., "Genetically engineered antibodies for direct antineoplastic treatment and systematic delivery of various therapeutic agents to cancer cells," Expert Opinion Biological Therapy, 1(4):603-617, 2001.
Bonniaud et al., "Progressive transforming growth factor β1-induced lung fibrosis is blocked by an orally active ALK5 kinase inhibitor," Am J Respir Crit Care Med, 171(8):889-898, 2005.
Bonniaud et al., "Smad3 null mice develop airspace enlargement and are resistant to TGF-β-mediated pulmonary fibrosis," J Immunol, 173(3):2099-2108, 2004.
Border and Noble, "Interactions of transforming growth factor-β and angiotensin II in renal fibrosis," Hypertension, 31(1 P 2):181-188, 1998.
Bottinger and Bitzer, "TGF-β signaling in renal disease," J Am Soc Nephrol, 13(10):2600-2610, 2002.
Breuss et al., "Expression of the β6 integrin subunit in development, neoplasia and tissue repair suggests a role in epithelial remodeling," J Cell Sci, 108(Pt 6):2241-2251, 1995.
Breuss et al., "Restricted distribution of integrin β 6 mRNA in primate epithelial tissues," J HistoChem Cytochem, 41(10):1521-1527, Oct. 1993.
Broekelmann et al., "Transforming growth factor β 1 is present at sites of extracellular matrix gene expression in human pulmonary fibrosis," Proc Natl Acad Sci USA, 88(15):6642-6646, Aug. 1991.
Brown et al., "Tolerance of single, but not multiple, amino acid replacements in antibody VH CDR 2: a means of minimizing B cell wastage from somatic hypermutation?" J Immunol, 156(9):3285-91, 1996.
Brunton et al., "The protrusive phase and full development of integrin-dependent adhesions in colon epithelial cells require FAK- and ERK-mediated actin spike formation: deregulation in cancer cells," Neoplasia, 3(3):215-226, 2001.
Busk et al., "Characterization of the integrin αvβ6 as a fibronectin-binding protein," J Biol Chem, 267(9):5790-5796, 1992.
Carrasquillo et al., "Indium-III T101 monoclonal antibody is superior to iodine-131 T101 in imaging of cutaneous T-cell lymphoma," J Nucl Med, 28(3):281-287, 1987.
Chapman, "Disorders of lung matrix remodeling," J Clin Invest, 113(2):148-157, 2004.
Chari et al., "Immunoconjugates containing novel maytansinoids: promising anticancer drugs," Cancer Res, 52(1):127-131, Jan. 1992.
Chevalier et al., "Renal tubulointerstitial injury from ureteral obstruction in the neonatal rat is allenuated by IGF-1," Kidney Int., 57(3):882-890, 2000.
Cho et al., "Inhibition of airway remodeling in IL-5-deficient mice," J Clin Invest, 113:551-560, Feb. 2004.
Chorev et al., "Approach to Discovering Novel Therapeutic Agents for Osteoporosis Based on Integrin Receptor Blockade," Biopolymers, 37:367-375, 1995.
Co et al., "Humanized antibodies for antiviral therapy," Proc Natl Acad Sci, 88:2869-2873, Apr. 1991.
Collard et al., "Combined corticosteroid and cyclophosphamide therapy does not alter survival in idiopathic pulmonary fibrosis," Chest, 125(6):2169-2174, Jun. 2004.
Colman, "Effects of amino acid sequence changes on antibody-antigen interactions," Res in Immun, 145:33-36, 1994.
Cooper et al., "Safety-modified episomal vectors for human gene therapy," Proc Natl Acad Sci USA, 94:6450-6455, Jun. 1997.
Cosgrove et al., "Collagen COL4A3 knockout: a mouse model for autosomal Alport syndrome," Genes Dev, 10 (23):2981-2992, 1996.
Cosgrove et al., "Integrin α1β1 and transforming growth factor-β 1 play distinct roles in alport glomerular pathogenesis and serve as dual targets for metabolic therapy," Am J Path, 157(5):1649-1659, Nov. 2000.
Dai et al., "Transforming growth factor-β 1 potentiates renal tubular epithelial cell death by a mechanism independent of Smad signaling," J Biol Chem, 278(14):12537-12545, 2003.
Damiano, "Integrins as novel drug targets for overcoming innate drug resistance," Curr Cancer Drug Targets, 2(1):37-43, 2002.
Davies et al., "Affinity improvement of single antibody VH domains: residues in all three hypervariable regions affect antigen binding," Immunotech, 2(3):169-179, Sep. 1996.
De Boer et al., "Transforming growth Factor β1 and Recruitment of Macrophages and Mast cells in Airways in Chronic Obstructive Pulmonary Disease," Am J Respir Crit Care Med, 158:1951-1957, 1998.
De Pascalis et al., "Grafting of "abbreviated" complementarity-determining regions containing specificity-determining residues essential for ligand contact to engineer a less immunogenic humanized monoclonal antibody," J Immunol, 169:3076-3084, 2002.
Deman et al., "Altered antioxidant defence in a mouse adriamycin model of glomerulosclerosis," Nephrol Dial Transplant, 16(1):147-150, 2001.
Denton et al., "Activation of a fibroblast-specific enhancer of the proα2(1) collagen gene in tight-skin mice," Arthritis Rheum, 44(3):712-722, Mar. 2001.
Dixit et al., Identification of a Sequence within the Integrin β6 Subunit Cytoplasmic Domain That is Required to Support the Specific Effect of αvβ6 on Proliferation in Three-dimensioinal Culture, J Biol Chem, 271(42):25976-25980, 1996.
Douglas et al., "Colchicine versus prednisone in the treatment of idiopathic pulmonary fibrosis. A randomized prospective study. Members of the Lung Study Group," Am J Respir Crit Care Med, 158(1):220-225, 1998.
Eickelberg et al., "Extracellular matrix deposition by primary human lung fibroblasts in response to TGF-β 1 and TGF-β3," Am J Physiol, 276(5 Pt 1):L814-L824, 1999.
Esteban et al., "New method for the chelation of indium-III to monoclonal antibodies: biodistribution and imaging of athymic mice bearing human colon carcinoma xenografts," J Nucl Med, 28(5):861-870, 1987.

(56) References Cited

OTHER PUBLICATIONS

European Search Report in European Application No. 06774580, dated Jun. 5, 2009, 12 pages.
European Search Report in European Application No. 07810296.9, dated Apr. 8, 2010, 5 pages.
European Search Report in European Application No. 11008296, dated Apr. 16, 2012, 6 pages.
Extended European Search Report in European Application No. 10012545.9, dated Apr. 29, 2011, 17 pages.
Extended European Search Report in European Application No. 10013155.6, dated Apr. 28, 2011, 10 pages.
Extended European Search Report in European Application No. 13768248.0, dated Aug. 19, 2015, 7 pages.
Franko et al., "Development of Fibrosis after Lung Irradiation in Relation to Inflammation and Lung Function in a Mouse Strain Prone to Fibrosis," Radiat. Res., 140(3):347-355, 1994.
George et al., "Transforming Growth Factor-β Initiates Wound Repair in Rat Liver through Induction of the EIIIA-Fibronectin Splice Isoform," Am J Pathol, 156(1):115-124, Jan. 2000.
George et al., "In vivo inhibition of rat stellate cell activation by soluble transforming growth factor β type II receptor: a potential new therapy for hepatic fibrosis," Proc Natl Acad Sci USA, 96(22):12719-12724, Oct. 26, 1999.
Ghannad et al, "Absence of αvβ6 integrin is linked to initiation and progression of periodontal disease," International Association for Dental Research, IADR, Abstract 85, Jul. 1-5, 2008.
Giusti et al., "Somatic diversification of S107 from an antiphosphocholine to an anti-DNA autoantibody is due to a single base change in its heavy chain variable region," Proc Natl Acad Sci USA, 84(9):2926-30, May 1987.
Gleizes et al., "TGF-β latency: biological significance and mechanisms of activation," Stem Cells, 15(3):190-197, 1997.
Griffiths et al., "Inactivation of the β 6 integrin subunit gene protects against bleomycin-induced pulmonary fibrosis," Concurrent Symposium 7: Extracellular Matrix: Regulation and Cell Behavior, 960-965, 1996, XP-000944784, p. 166A, Abstract only.
Guy et al., "Induction of mammary tumors by expression of polyomavirus middle T oncogene: a transgenic mouse model for metastatic disease," Mol Cell Biol, 12(3):954-961, Mar. 1992.
Hakkinen et al., "Immunolocalization of tenascin-C, α9 integrin subunit, and αvβ6 integrin during wound healing in human oral mucosa," J HistoChem CytoChem, 48(7):985-998, 2000.
Hakkinen et al., "Increased expression of β6-integrin in skin leads to spontaneous development of chronic wounds," Am J Pathol, 164(1):229-242, Jan. 2004.
Halder et al., "A specific inhibitor of TGF-β receptor kinase, SB-431542, as a potent antitumor agent for human cancers," Neoplasia, 7(5):509-521, May 2005.
Hall et al., "A single amino acid mutation in CDRs of the 3-14-9 L chain abolished expression of the IDA 10-defined idiotope and antigen binding," J Immunol, 149(5):1605-1612, Sep. 1992.
Hamidi et al., "Expression of α(v)β6 integrin in oral leukoplakia," Br. J Cancer, 82(8):1433-1440, 2000.
Haston et al., "Inheritance of susceptibility to bleomycin-induced pulmonary fibrosis in the mouse," Cancer Res., 56(11):2596-2601, Jun. 1, 1996.
Hezel et al. "TGF-β and αvβ6 integrin act in a common pathway to suppress pancreatic cancer progression," Cancer Res, 72(18):4840-4845, Sep. 2012.
Hinman et al., "Preparation and characterization of monoclonal antibody conjugates of the calicheamicins: a novel and potent family of antitumor antibiotics," Cancer Research, 53(14):3336-3342, Jul. 1, 1993.
Holt et al., "Domain antibodies: proteins for therapy," Trends in BioTech, 21(11):484-490, Nov. 2003.
Horan et al., "Partial Inhibition of Integrin αvβ6 Prevents Pulmonary Fibrosis Without Exacerbating Inflammation," Am J Respir Crit Care Med, 177(1):56-65, 2008.

Huang et al., "A Point Mutation in the Integrin β6 Subunit Abolishes Both αvβ6 Binding to Fibronectin and Receptor Localization to Focal Contacts," Am J Respir Cell Mol Biol, 13(2):245-251, 1995.
Huang et al., "Expression of the Human Integrin β6 Subunit in Alveolar Type II Cells and Bronchiolar Epithelial Cells Reverses Lung Inflammation in β6 Knockout Mice," Am J Respir Cell Mol Biol, 19(4):636-642, 1998.
Huang et al., "Inactivation of the integrin β 6 subunit gene reveals a role of epithelial integrins in regulating inflammation in the lung and skin," J Cell Biol, 133(4):921-928, May 1996.
Huang et al., "The integrin αvβ6 is critical for keratinocyte migration on both its known ligand, fibronectin, and on vitronectin," J Cell Sci, 111(Pt 15):2189-2195, Aug. 1998.
Hynes, "Integrins: versatility, modulation, and signaling in cell adhesion," Cell, 69:11-25, Apr. 3, 1992.
Iacobuzio-Donahue et al., "Missense mutations of MADH4: characterization of the mutational hot spot and functional consequences in human tumors," Clin Cancer Res, 10:1597-1604, Mar. 2004.
Inazaki et al., "Smad3 deficiency attenuates renal fibrosis, inflammation, and apoptosis after unilateral ureteral obstruction," Kidney Int, 66(2):597-604, 2004.
International Preliminary Report on Patentability in International Application No. PCT/US07/15692, dated Oct. 20, 2011, 87 pages.
International Preliminary Report on Patentability in International Application No. PCT/US2007/081473, dated Apr. 22, 2009, 7 pages.
International Preliminary Report on Patentability in International Application No. PCT/US2013/032082, dated Oct. 1, 2014, 13 pages.
International Preliminary Report on Patentability in International Application No. PCT/US2014/027826, dated Sep. 15, 2015, 10 pages.
International Preliminary Report on Patentability in International Application No. PCT/US2014/028888, dated Sep. 15, 2015, 9 pages.
International Prelminary Report on Patentability and Written Opinion in International Application No. PCT/US2007/081473, dated Apr. 22, 2009, 7 pages.
International Search Report and Written Opinion in International Application No. PCT/US2013/032082, dated Jul. 8, 2013, 16 pages.
International Search Report and Written Opinion in International Application No. PCT/US2014/027826, dated Sep. 18, 2014, 16 pages.
International Search Report and Written Opinion in International Application No. PCT/US2014/028888, dated Jul. 7, 2014, 15 pages.
Iyer et al., "Targeting TGFβ signaling for cancer therapy," Cancer Biol Ther, 4(3):261-266, Mar. 2005.
Jakobovits et al., "Immunoglobulin Gene Expression in Development and Disease," Ann NY Acad Sci, 764:525-535, Sep. 29, 1995.
Jalkanen et al., "Cell surface proteoglycan of mouse mammary epithelial cells is shed by cleavage of its matrix-binding ectodomain from its membrane-associated domain," J Cell Biol, 105(6 Pt 2):3087-3096, Dec. 1987.
Jalkanen et al., "Heparan sulfate proteoglycans from mouse mammary epithelial cells: localization on the cell surface with a monoclonal antibody," J Cell Biol, 101(3):976-985, Sep. 1985.
Janes and Watt, "Switch from αvβ5 to αvβ6 integrin expression protects squamous cell carcinomas from anoikis," J Cell Biol, 166(3):419-431, Aug. 2004.
Ji and Si, "Inhibition of hepatitis B virus by retroviral vectors expressing antisense RNA," J Viral Hepat, 4:167-173, Jan. 1997.
Juliano, "Signal transduction by integrins and its role in the regulation of tumor growth," Cancer Metastasis Rev., 13:25-30, Mar. 1994.
Kaiser, "Cancer. First pass at cancer genome reveals complex landscape," Science, 313:1370, Sep. 8, 2006.
Kaminski et al., "Global analysis of gene expression in pulmonary fibrosis reveals distinct programs regulating lung inflammation and fibrosis," Proc Natl Acad Sci USA, 97(4):1778-1783, Feb. 15, 2000.
Kaneda et al., "Prevention of Restenosis by Gene Therapy," Ann NY Acad Sci, 811:299-310, 1997.

(56) References Cited

OTHER PUBLICATIONS

Kasuga et al., "Effects of anti-TGF-β type II receptor antibody on experimental glomerulonephritis," Kidney Int., 60 (5):1745-1755, 2001.
Kennedy et al., "Protein-Protein Coupling Reactions and the Applications of Protein Conjugates," Clin Chim Acta, 70:1-31, Jul. 1976.
Khalil, "TGF-β: from latent to active," Microbes Infect, 1(15):1255-1263, Dec. 1999.
Klimka et al., "Human anti-CD30 recombinant antibodies by guided phage antibody selection using cell palming," Br J Cancer, 83:252-260, Jul. 2000.
Knight et al., "Enteric Expression of the Integrin αvβ6 is Essential for Nematode-Induced Mucosal Mast Cell Hyperplasia and Expression of the Granule Chymase, Mouse Mast Cell Protease-1," Am J Pathol, 161(3):771-779, Sep. 2002.
Koivisto et al., "Different integrins mediate cell spreading, haptotaxis and lateral migration of HaCaT keratinocytes on fibronectin," Cell Adhes Commun, 7(3):245-257, 1999.
Kolbinger et al., "Humanization of a mouse anti-human IgE antibody: a potential therapeutic for IgE-mediated allergies," Protein Eng., 6(8):971-980, Nov. 1993.
Konigshoff et al., "TGF-β signaling in COPD: deciphering genetic and cellular susceptibilities for future therapeutic regimen," Swiss Med Wkly, 139(39-40):554-563, 2009.
Koopman Van Aarsen et al., "Antibody-Mediated Blockade of Integrin αvβ6 Inhibits Tumor Progression in vivo by a Transforming Growth Factor-β-Regulated Mechanism," Cancer Res, 68(2):561-570, Jan. 2008.
Kracklauer et al., "TGFβ1 Signaling Via αVβ6 Integrin," Mol Cancer 2(28), Aug. 7, 2003, 16 pages.
Kunicki et al., "Molecular Determinants of Arg-Gly-Asp Ligand Specificity for $β_3$ Integrins," J Biol Chem, 272(7):4103-4107, Feb. 14, 1997.
Kunicki et al., "The Exchange of Arg-Gly-Asp (RGD) and Arg-Tyr-Asp (RYD) Binding Sequences in a recombinant Murine Fab Fragment Specific for the Integrin $α_{IIb}β_3$ Does Not Alter Integrin Recognition," J Biol Chem, 270(28):16660-16665, Jul. 1995.
Kuntz, "Structure-based strategies for drug design and discovery," Science, 257:1078-1082, Aug. 21, 1992.
Kussie et al., "A single engineered amino acid substitution changes antibody fine specificity," J Immunol, 152(1):146-52, 1994.
Leask et al.. "TGF-β signaling and the fibrotic response," FASEB J, 18(7):816-827, 2004.
Lee et al., "Increased vaccine-Specific T Cell Frequency After Peptide-Based Vaccination Correlates with Increased Susceptibility to In Vitro Stimulation but Does Not Lead to Tumor Regression," J Immunol, 163:6292-6300, 1999.
Lehmann et al., "A Monoclonal Antibody Inhibits Adhesion to Fibronectin and Vitronectin of a Colon Carcinoma Cell Line and Recognizes the Integrins $α_vβ_3$, $α_vβ_5$, and $α_vβ_6$," Cancer Res, 54(8):2102-2107, Apr. 1994.
Leone et al., "A blocking monoclonal antibody to integrin αvβ6 inhibits tumor growth in a human pharyngeal 3 xenograft model," Proceedings of the Annual Meeting of the American Association for Cancer Research, vol. 44, XP008070338, 2003.
Li et al., "Transforming growth factor-β regulation of immune responses," Annu Rev Immunol, 24:99-146, 2006.
Li et al., "αvβ6-Fyn signaling promotes oral cancer progression," J Biol Chem, 278(43):41646-41653, Oct. 2003.
Liu et al., "Fine mapping of the antigen-antibody interaction of scFv215, a recombinant antibody inhibiting RNA polymerase II from *Drosophila melanogaster*," J Mol Recognit, 12(2):103-11, 1999.
Ludbrook et al., "The integrin αvβ3 is a receptor for the latency-associated peptides of transofrming growth factors $β_1$ and $β_3$," BioChem J, 369(Pt 2):311-318, 2003.
Ma et al., "Protection against unilateral ureteral obstruction (UUO) induced tuboloinsterstitial fibrosis in αvβ6 −/− mice," Lab Investigation, 81:189A, Jan. 2001.
Ma et al., "Transforming Growth Factor β (TGFB) Dependent and Independent Pathways of Induction of Tubulointerstitial Fibrosis in αvβ6−/− mice," J Am Soc Nephrol, 12:819A, 2001.
Ma et al., "Accelerated fibrosis and collagen deposition develop in the renal interstitium of angiotensin type 2 receptor null mutant mice during ureteral obstruction," Kidney Int, 53(4):937-944, 1998.
Ma et al., "Transforming growth factor-β-dependent and -independent pathways of induction of tubulointerstitial fibrosis in β6(−/−) mice," Am J Pathol, 163(4):1261-1273, 2003.
Massague, "TGF-β signal transduction," Annu Rev BioChem, 67:753-791, 1998.
Maynard, "Antibody Engineering," Annu Rev Biomed Eng, 2:339-376, 2000.
Mellman, "What Next for Cancer Immunotherapy?" The Scientist, 20(1):47-56, 2006.
Miller et al., "Ligand binding to proteins: the binding landscape model," Protein Sci, 6:2166-2179, 1997.
Miller et al., "MCF10DCIS.com xenograft model of human comedo ductal carcinoma in situ," J Natl Cancer Inst, 92(14):1185-1186, Jul. 19, 2000.
Miner and Sanes, "Molecular and functional defects in kidneys of mice lacking collagen α 3(IV): implications for Alport syndrome," J Cell Biol, 135(5):1403-1413, Dec. 1996.
Mitjans et al., "An anti-αv-Integrin antibody that blocks integrin function inhibits the development of a human melanoma in nude mice," J Cell Sci., 108(Pt 8):2825-2838, 1995.
Morgan et al., "The integrin cytoplasmic-tall motif EKQKVDLSTDC is sufficient to promote tumor cell invasion mediated by matrix metalloproteinase (MMP)-2 or MMP-9," J Biol Chem, 279(25):26533-26539, Jun. 2004.
Morris et al., "Loss of integrin αvβ6-mediated TGF-β activation causes Mmp12-dependent emphysema," Nature, 422(6928):169-173, Mar. 2003.
Movsas et al., "Pulmonary radiation injury," Chest, 111(4):1061-1076, Apr. 1997.
Mu et al., "The integrin αvβ8 mediates epithelial homeostasis through MT1-MMP-dependent activation of TGF-β1," J Cell Biol, 157(3):493-507, Apr. 29, 2002.
Munger et al., "The Integrin αvβ6 Binds and Activates Latent TGFβ1: A Mechanism for Regulating Pulmonary Infmallation and Fibrosis," Cell, 96(3):319-328, Feb. 5, 1999.
Munger et al., "Latent transforming growth factor-β: structural features and mechanisms of activation," Kidney Int., 51:1376-1382, 1997.
Muraoka et al., "Blockade of TGF-β inhibits mammary tumor cell viability, migration, and metastases," J Clin Invest., 109(12):1551-1559, Jun. 2002.
Murayama and Horiuchi, "Brief Communication: Antisense Oligonucleotides to p53 Tumor Suppressor Suppress the Induction of Apoptosis by Epidermal Growth Factor in NCI-H 596 Human Lung Cancer Cells," Antisense Nucleic Acid Drug Dev, 7:109-114, Apr. 1997.
Neuberger et al., "Recombinant antibodies possessing novel effector functions," Nature, 312:604-608, Dec. 1984.
Neurohr et al., "Activation of Transforming Growth Factor-β by the Integrin aiphaVβ8 Delays Epithelial Wound Closure," Am J Respir Cell Mol Biol, 35:252-259, 2006.
Niidome et al., "Binding of Cationic α-Helical Peptides to Plasmid DNA and Their Gene Transfer Abilities into Cells," J Biol Chem, 272:15307-15312, Jun. 1997.
Niu et al., "The αvβ6 integrin regulates its own expression with cell crowding: implications for tumour progression," Int J Cancer, 92(1):40-48, 2001.
O'Brien et al., "Humanization of monoclonal antibodies by CDR grafting," Methods Mol. Biol, 207:81-100, 2003.
Oft et al., "TGFβ signaling is necessary for carcinoma cell invasiveness and metastasis," Curr. Biol, 8(23):1243-1252, 1998.
Ohta, "Gene polymorphism in airway remodeling of asthma," Tokyo University School of Medicine, 20-26, with English translation, 2004.
Orlandi et al., "Cloning immunoglobulin variable domains for expression by the polymerase chain reaction," Proc Natl Acad Sci USA, 86(10):3833-3837, May 1989.

(56) References Cited

OTHER PUBLICATIONS

Palmer et al., "An Association Between Alveolar Cell Proliferation and Interstitial Fibrosis Following Acute Lung Injury," Chest, 69(2):307-309, Feb. 1976.
Pasqualini et al., "A Peptide Isolated from Phage Display Libraries is a Structural and Functional Mimic of an RGD-binding Site on Integrins," J Cell Biol, 130(5):1189-1196, Sep. 1995.
Paul, Fundamental Immunology, 3rd ed, 242:292-295, 1993.
Pierschbacher et al., "Manipulation of Cellular Interactions With Biomaterials Toward a Therapeutic Outcome: A Perspective," J Cell. BioChem, 56(2):150-154, Oct. 1994.
Pini et al., "Design and use of a phage display library; Human antibodies with subnanomolar affinity against a marker of angiogenesis eluted from a two-dimensional gel," J Biol Chem, 273(34):21769-21776, Aug. 1998.
Pittet et al., "TGF-β is a critical mediator of acute lung injury," J Clin Invest, 107(12):1537-1544, Jun. 2001.
PLoS Medicine, 3(4):0420, Apr. 2006.
Pons et al., "Decreased macrophage release of TGF-β and TIMP-1 in chronic obstructive pulmonary disease," Eur. Respir J, 26(1):60-66, 2005.
Presta, "Antibody engineering for therapeutics," Curr Opin in Struct Biol, 13:519-525, 2003.
Prieto et al., "Multiple integrins mediate cell attachment to cytotactin/tenascin," Proc Natl Acad Sci USA, 90(21):10154-10158, Nov. 1993.
Puthawala et al., "Inhibition of integrin αvβ6, an activator of latent transforming growth factor-β, prevents radiation induced lung fibrosis," Am J Respir Crit Care Med, 177(1):82-90, 2008.
Queen et al., "A humanized antibody that binds to the interleukin 2 receptor," Proc Natl Acad Sci USA, 86(24):10029-10033, Dec. 1989.
Raguse et al., "Cilengitide (EMD 121974) arrests the growth of a heavily pretreated highly vascularized head and neck tumour," Oral Oncol, 40(2):228-230, 2004.
Redman, "Orofacial and gastrointestinal hyperplasia and neoplasia in smad4$^{+/-}$ and efl $^{+/-}$/smad4$^{+/-}$ mutant mice," J Oral Pathol Med, 34(1): 23-9, 2005.
Regezi et al., "Tenascin and β6 integrin are overexpressed in floor of mouth in situ carcinomas and invasive squamous cell carcinomas," Oral Oncol, 38:332-336, 2002.
Riechmann et al., "Reshaping human antibodies for therapy," Nature, 332(24):323-327, Mar. 1988.
Ritter et al., "Serological analysis for human anti-human antibody responses in colon cancer patients treated with repeated doses of humanized monoclonal antibody A33," Cancer Research, 61:6851-6859, Sep. 15, 2001.
Roberts et al., "Transforming growth factor type β: rapid induction of fibrosis and angiogenesis in vivo and stimulation of collagen formation in vitro," Proc Natl Acad Sci USA, 83(12):4167-4171, Jun. 1986.
Rudikoff et al., "Single amino acid substitution altering antigen-binding specificity," Proc Natl Acad Sci USA, 79(6):1979-1983, Mar. 1982.
Ruoslahti and Giancotti, "Integrins and tumor cell dissemination," Cancer Cells, 1:119-126, Dec. 1989.
Ruoslahti and Reed, "Anchorage dependence, 1994 integrins, and apoptosis," Cell, 77:477-478, May 20, 1994.
Ruoslahti, "RGD and Other Recognition Sequences for Integrins," Ann Rev Cell Dev Biol, 12:697-715, 1996.
Ruoslahti, "Integrins," J Clin Invest, 87(1):1-5, Jan. 1991.
Sampson et al., "Global gene expression analysis reveals a role for the al integrin in renal pathogenesis," J Biol Chem, 276(36):34182-34188, 2001.
Schildbach et al., "Contribution of a single heavy chain residue to specificity of an anti-digoxin monoclonal antibody," Protein Sci, 3(5):737-49, 1994.
Schildbach et al., "Heavy chain position 50 is a determinant of affinity and specificity for the anti-digoxin antibody 26-10," J Biol Chem, 268(29):21739-47, Oct. 1993.

Schuurs and Van Weemen, "Enzyme-Immunoassay," Clin Chim Acta, 81:1-40, 1977.
Selman, "Idiopathic pulmonary fibrosis challenges for the future," Chest, 120(1):8-10, Jul. 2001.
Shapiro, "The pathophysiology of COPD: What goes wrong and why?" Proceedings Adv Stud Med, 3(2B):S91-S98, Feb. 2003.
Sheppard et al., "Complete Amino Acid Sequence of a Novel Integrin β Subunit (β6) Identified in Epithelial Cells Using the Polymerase Chain Reaction," J Biol Chem, 265(20):11502-11507, 1990.
Sheppard et al., "Integrin-mediated activation of transforming growth factor-β(1) in pulmonary fibrosis," Chest, 120(S1):49S-53S, Jul. 2001.
Sheppard, "Airway Epithelial Integrins: Why So Many?" Am J Respir Cell Mol Biol, 19(3):349-351, 1998.
Sheppard, "Transforming growth factor β: a central modulator of pulmonary and airway inflammation and fibrosis," Proc Am Thorac Soc, 3(5):413-417, Jul. 2006.
Sheppard. "Functions of pulmonary epithelial integrins: from development to disease," Physiol Rev, 83(3):673-686, Jul. 2003.
Shihab et al., "Transforming growth factor-β and matrix protein expression in acute and chronic rejection of human renal allografts," J Am Soc Nephrol, 6(2):286-294, 1995.
Sime et al., "Adenovector-mediated gene transfer of active transforming growth factor-β 1 induces prolonged severe fibrosis in rat lung," J Clin Invest, 100(4):768-776, Aug. 1997.
Sipos et al., "Immunohistochemical screening for β6-integrin subunit expression in adenocarcinomas using a novel monoclonal antibody reveals strong up-regulation in pancreatic ductal adenocarcinomas in vivo and in vitro," Histopathology, 45:226-236, 2004.
Sleijfer, "Bleomycin-induced pneumonitis," Chest, 120(2):617-624, Aug. 2001.
Smith et al., "Building Synthetic Antibodies as Adhesive Ligands for Integrins," J Biol Chem, 269:32788-32795, Dec. 1994.
Stedman's Medical Dictionary, 25th ed, pp. 1652-1653, 1990.
Subramanian et al.., "Targeting Endogenous Transforming Growth Factor—Receptor Signaling in SMAD4-Deficient Human Pancreatic Carcinoma Cells Inhibits Their Invasive Phenotype," Cancer Res, 64(15):5200-5211, XP08102563, Aug. 2004.
Tamura et al., "Structural correlates of an anti-carcinoma antibody: identification of specificity-determining residues (SDRs) and development of a minimally immunogenic antibody variant by retention of SDRs only," J Immunol, 164:1432-1441, 2000.
Tatler et al., "Integrin αvβ5-mediated TGF-β activation by airway smooth muscle cells in asthma," J Immunol, 187:6094-6107, 2011.
Thomas and Massague, "TGF-β directly targets cytotoxic T cell functions during tumor evasion of immune surveillance," Cancer Cell, 8:369-380, Nov. 2005.
Thomas et al., "αvβ6 Integrin Upregulates Matrix Metalloproteinase 9 and Promotes Migration of Normal Oral Keratinocytes," J Invest Dermatol., 116:898-904, 2001.
Thomas et al., "Binding of TGF-β1 latency-associated peptide (LAP) to α(v)β6 integrin modulates behaviour of squamous carcinoma cells," Br. J Cancer 87(8):859-867, 2002.
Thomas et al., "Expression of the αvβ6 integrin promotes migration and invasion in squamous carcinoma cells," J Invest Dermatol, 117(1):67-73, 2001.
Thomas et al., "αvβ6 Integrin in Wound Heading and Cancer of the Oral Cavity," J Oral Pathol Med, 35(1):1-10, 2006.
Thomas et al., "αvβ6 integrin promotes invasion of squamous carcinoma cells through up-regulation of matrix metalloproteinase-9," Int J Cancer, 92(5):641-650, 2001.
Torra et al., "Collagen type IV (α3-α4) nephropathy: from isolated haematuria to renal failure," Nephrol Dial Transplant, 19(10):2429-2432, 2004.
Trevillian et al., "αvβ6 Integrin expression in diseased and transplanted kidneys," Kidney Int, 66:1423-1433, 2004.
Tsushima et al., "Acute Lung Injury Review," Inter Med, 48:621-630, 2009.
Turner-Warwick et al., "Cryptogenic fibrosing alveolitis: response to corticosteroid treatment and its effect on survival," Thorax, 35(8):593-599, 1980.

(56) References Cited

OTHER PUBLICATIONS

Vajdos et al., "Comprehensive functional maps of the antigen-binding site of an anti-ErbB2 antibody obtained with shotgun scanning mutagenesis," J Mol Biol, 320(2):415-428, 2002.

Van Den Broek and Van De Vijver, "Assesment of problems in diagnostic and research immunohistochemistry associate with epitope instability in stored paraffin sections," Appl ImmunohistoChem, Mol Morphol, 8(4):316-321, Dec. 2000.

Varga et al., "Transforming growth factor $\beta$ (TGF $\beta$) causes a persistent increase in steady-state amounts of type 33 I and type III collagen and fibronectin mRNAs in normal human dermal fibroblasts," BioChem J, 247(3):597-604, 1987.

Vidal et al., "Nouvelle strategie pour vectorisation d'ARN dans des cellules de mammiferes. Utilisation d'un vecteur peptidique," CR Acad Sci III, 320:279-287, Apr. 1997, includes English Abstract and English Abridged Version.

Wada et al., "Cloning of mouse integrin $\alpha v$ cDNA and role of the $\alpha v$-related matrix receptors in metanephric development," J Cell Biol, 132(6):1161-1176, Mar. 1996.

Wahl, "Transforming growth factor $\beta$: the good, the bad, and the ugly," J Exp Med, 180(5):1587-1590, Nov. 1994.

Walker et al., "Valvular myofibroblast activation by transforming growth factor-$\beta$: implications for pathological extracellular matrix remodeling in heart valve disease," Circ Res, 95(3):253-260, Aug. 6, 2004.

Wang et al., "Progressive adriamycin nephropathy in mice: sequence of histologic and immunohistochemical events," Kidney Int, 58(4):1797-1804, 2000.

Wang et al., "Reduction of bleomycin induced lung fibrosis by transforming growth factor $\beta$ soluble receptor in hamsters," Thorax, 54(9):805-812, 1999.

Watanabe et al., "Regression of Established Tumors Expressing P-glycoprotein by Combinations of Adriamycin, Cyclosporin Derivatives, and MRK-16 Antibodies," J Natl Cancer Institute, 89(7):512-518, Apr. 1997.

Weinacker et al., "Role of the Integrin $\alpha v \beta 6$ in Cell Attachment to Fibronectin, Heterologous Expression of Intact and Secreted Forms of the Receptor," J Biol Chem, 269(9):6940-6948, Mar. 1994.

Weinreb et al., "Function-blocking integrin $\alpha v \beta 6$ monoclonal antibodies: distinct ligand-mimetic and non ligand-mimetic classes," J Biol Chem, 279(17):17875-17887, Apr. 2004.

Wheeler and Bernard, "Acute lung injury and the acute respiratory distress syndrome: a clinical review," Lancet, 369:1553-64, Apr. 2007.

Wu and Kabat., "An analysis of the sequences of the variable regions of Bence Jones proteins and myeloma light chains and their implications for antibody complementarity," J Exp Med, 132(2):211-250, 1970.

Wu et al., "Stepwise in vitro affinity maturation of Vitaxin, an $\alpha_v \beta_3$-specific humanized mAb," Proc Natl Acad Sci USA, 95(11):6037-6042, May 1998.

Wyckoff et al., "A critical step in metastasis: in vivo analysis of intravasation at the primly tumor," Cancer Res, 60(9):2504-2511, May 2000.

Xiang et al., "Study of B72.3 combining sites by molecular modeling and site-directed mutagenesis," Protein Eng., 13(5):339-344, 2000.

Xiao et al., "Adeno-associated virus (AAV) vector antisense gene transfer in vivo decreases $GABA_A$ $\alpha_1$ containing receptors and increases inferior collicular seizure sensitivity," Brain Res, 756:76-83, 1997.

Xu et al., "Lysophosphatidic Acid Induces avB6 ntegrin-Mediated TGF-B Activation via the LPA2 Receptor and the Small G Protein Gaq," Am J of Pathol, 174:1264-1279, Apr. 2009.

Xue et al., "Role of the av~6 Integrin in Human Oral Squamous Cell Carcinoma Growth in Vivo in Vitro," Biochemical and Biophysical Research Communications, 288:610-618, 2001.

Yamamoto et al., "Expression of transforming growth factor $\beta$ is elevated in human and experimental diabetic nephropathy," Proc Natl Acad Sci USA, 90(5):1814-1818, Mar. 1993.

Yang et al., "Lifetime exposure to a soluble TGF-$\beta$ antagonist protects mice against metastasis without adverse side effects," J Clin Invest., 109(12):1607-1615, Jun. 2002.

Yokosaki et al., "Differential effects of the integrins $\alpha 9 \beta 1$, $\alpha v \beta 3$, and $\alpha v \beta 6$ on cell proliferative responses to tenascin. Roles of the $\beta$ subunit extracellular and cytoplasmic domains," J Biol Chem, 271(39):24144-24150, Sep. 1996.

Zambruno et al., "Transforming growth factor-$\beta$ 1 modulates $\beta 1$ and $\beta 5$ integrin receptors and induces the de novo expression of the $\alpha v \beta 6$ heterodimer in normal human keratinocytes: implications for wound healing," J Cell Biol, 129(3):853-865, May 1995.

Zhang et al., "Monoclonal antibody recognizing a carcinoembryonic antigen epitope differentially expressed in human colonie carcinoma versus normal adult colon tissues," Cancer Research, 49:5766-5773, Oct. 15, 1989.

Zisman et al., "Cyclophosphamide in the treatment of idiopathic pulmonary fibrosis: a prospective study in patients who failed to respond to corticosteroids," Chest, 117(6):1619-1626, Jun. 2000.

Ziyadeh et al., "Long-term prevention of renal insufficiency, excess matrix gene expression, and glomerular mesangial matrix expansion by treatment with monoclonal antitransforming growth factor-$\beta$ antibody in db/db diabetic mice," Proc Natl Acad Sci USA, 97(14):8015-8020, Jul. 5, 2000.

\* cited by examiner

FIGURE 1

|  | CDR1 | CDR2 |
|---|---|---|
| 1A8 VH Murine: | QVQFQQSGPELVRPGVSVKISCKGSSYTFTDYTMHWVKISHAKTLEWIGVIDTYYGKTNYNQKFEGKATMTVDKSSSTAYM |  |
| 1A8 VH1: | QVQFVQSGPELKKPGEASVKVSCKGSSYTFTDYTMHWVKLAHAKTLEWIGVIDTYYGKTNYNQKFEGRATMTVDKSSSTAYM |  |
| 1A8 VH2: | QVQLVQSGAEVKKPGASVKVSCKGSSYTFTDYTMHWVKLASAKTLEWIGVIDTYYGKTNYNQKFEGRATMTVDKSSSTAYM |  |
| 1A8 VH3: | QVQLVQSGAEVKKPGASVKVSCKGSSYTFTDYTMHWVKLASAKTLEWIGVIDTYYGKTNYNQKFEGRATMTVDKSSSTAYM |  |
| 1A8 VH4: | QVQLVQSGAEVKKPGASVKLSCKGSSYTFTDYTMHWVKLASAKTLEWIGVIDTYYGKTNYNQKFEGRATITVDKSSSTAYM |  |
| 1A8 VH5: | QVQFVQSGPELKKPGASVKLSCKGSSYTFTDYTMHWVKLAHAKTLEWIGVIDTYYGKTNYNQKFEGRATITVDKSSSTAYM |  |
| 1A8 VH6: | QVQFVQSGPELKKPGASVKLSCKGSSYTFTDYTMHWVKLAHAKTLEWIGVIDTYYGKTNYNQKFEGKATMTVDKSSSTAYM |  |

|  | CDR3 |  |
|---|---|---|
| 1A8 VH Murine: | DLARLTSEDSAVYYCARGGFRRGDRPSLRYAMDSWGQGTSVTVSS | (SEQ ID NO:48) |
| 1A8 VH1: | ELARLRSEDSAVYYCARGGFRRGDRPSLRYAMDSWGQGTSVTVSS | (SEQ ID NO:1) |
| 1A8 VH2: | ELSSLRSEDTAVYYCARGGFRRGDRPSLRYAMDSWGQGTLVTVSS | (SEQ ID NO:3) |
| 1A8 VH3: | ELSSLRSEDTAVYYCARGGFRRGDRPSLRYAMDSWGQGTLVTVSS | (SEQ ID NO:5) |
| 1A8 VH4: | ELSSLRSEDTAVYYCARGGFRRGDRPSLRYAMDSWGQGTSVTVSS | (SEQ ID NO:7) |
| 1A8 VH5: | ELARLTSEDSAVYYCARGGFRRGDRPSLRYAMDSWGQGTSVTVSS | (SEQ ID NO:50) |
| 1A8 VH6: | DLARLTSEDSAVYYCARGGFRRGDRPSLRYAMDSWGQGTSVTVSS | (SEQ ID NO:52) |

FIGURE 2

```
                                    CDR1                                                      CDR2
1A8 Vk Murine: DIVLTQSPASLAVSLGQRATISCRASQSVSISTYSYIHWFQQKPGQPPKLLIKYASNLESGVPARFSGSGSGTDFTLNIHP
1A8 Vk1:       DIVLTQSPDSLAVSLGERATINCRASQSVSISTYSYIHWFQQKPGQPPKLLIKYASNLESGVPDRFSGSGSGTDFTLNIHP
1A8 Vk2:       DIVLTQSPDSLAVSLGERATINCRASQSVSISTYSYIHWFQQKPGQPPKLLIKYASNLESGVPDRFSGSGSGTDFTLKISR
1A8 Vk3:       DIVMTQSPDSLAVSLGERATINCRASQSVSISTYSYIHWFQQKPGQPPKLLIKYASNLESGVPDRFSGSGSGTDFTLKISR CDR3
1A8 Vk Murine: VEEEDTAIYYCQHSWEIPYTFGGGTKVEIK    (SEQ ID NO:49)
1A8 Vk1:       VEEEDVGIYYCQHSWEIPYTFGGGTKVEIK    (SEQ ID NO:9 )
1A8 Vk2:       VEEEDVGIYYCQHSWEIPYTFGGGTKVEIK    (SEQ ID NO:11)
1A8 Vk3:       VEAEDVGIYYCQHSWEIPYTFGGGTKVEIK    (SEQ ID NO:13)
```

ANTI-ALPHA V BETA 6 ANTIBODIES AND USES THEREOF

CROSS-REFERENCE TO RELATED APPLICATIONS

This application claims the benefit of priority to U.S. Provisional Appl. No. 61/790,408 filed Mar. 15, 2013, and U.S. Provisional Appl. No. 61/847,634 filed Jul. 18, 2013, the contents of both of which are incorporated by reference in their entirety herein.

FIELD

This invention relates generally to antibodies that bind to the alpha v beta 6 ($\alpha v \beta_6$) integrin and uses thereof.

BACKGROUND

Integrins are cell surface glycoprotein receptors that bind extracellular matrix proteins and mediate cell-cell and cell-extracellular matrix interactions (generally referred to as cell adhesion events). These receptors are composed of noncovalently associated alpha ($\alpha$) and beta ($\beta$) chains that combine to give a variety of heterodimeric proteins with distinct cellular and adhesive specificities. Certain integrins have been implicated in the regulation of a variety of cellular processes including cellular adhesion, migration, invasion, differentiation, proliferation, apoptosis, and gene expression.

The $\alpha_v\beta_6$ receptor is one member of a family of integrins that are expressed as cell surface heterodimeric proteins. While the $\alpha_v$ subunit can form a heterodimer with a variety of $\beta$ subunits ($\beta$ is $\beta_3$, $\beta_5$, $\beta_6$ and $\beta_8$), the $\beta_6$ subunit can only be expressed as a heterodimer with the $\alpha_v$ subunit. The extracellular and cytoplasmic domains of the $\beta_6$ subunit mediate different cellular activities: the extracellular and transmembrane domains have been shown to mediate TGF-$\beta$ activation and adhesion; whereas the cytoplasmic domain of the $\beta_6$ subunit contains a unique 11-amino acid sequence that is important in mediating $\alpha v \beta 6$ regulated cell proliferation, MMP production, migration, and promotes survival.

$\alpha v \beta 6$ can bind to several ligands including fibronectin, tenascin, and the latency associated peptide-1 and -3 (LAP1 and LAP3) (the N-terminal 278 amino acids of the latent precursor form of TGF-$\beta$1). The TGF-$\beta$ cytokine is synthesized as a latent complex in which the N-terminal LAP is non-covalently associated with the mature active C-terminal TGF-$\beta$ cytokine. The latent TGF-$\beta$ complex cannot bind to its cognate receptor and thus is not biologically active until converted to an active form. $\alpha v \beta 6$ binds LAP1 and LAP3 through interaction with an arginine-glycine-aspartate ("RGD") motif and this binding of $\alpha v \beta 6$ to LAP1 or LAP3 leads to activation of the latent precursor form of TGF-$\beta$1 and TGF-$\beta$3 as a result of a conformational change in the latent complex allowing TGF-$\beta$ to bind to its receptor. Thus, upregulated expression of $\alpha v \beta 6$ can lead to local activation of TGF-$\beta$, which in turn can activate a cascade of downstream events.

The TGF-$\beta$ cytokine is a pleiotropic growth factor that regulates cell proliferation, differentiation, and immune responses. TGF-$\beta$ also plays a role in cancer. TGF-$\beta$ is recognized to have tumor suppressor and growth inhibitory activity, yet many tumors evolve a resistance to growth suppressive activities of TGF-$\beta$. In established tumors, TGF-$\beta$ expression and activity has been implicated in promoting tumor survival, progression, and metastases. This is thought to be mediated by both autocrine and paracrine effects in the local tumor-stromal environment, including the effects of TGF-$\beta$ on immune surveillance, angiogenesis, and increased tumor interstitial pressure. Several studies have shown the antitumor and anti-metastatic effects of inhibiting TGF-$\beta$.

The $\alpha v \beta 6$ integrin has multiple regulatory functions in tumor cell biology. The expression of $\alpha_v \beta_6$ is restricted to epithelial cells where it is expressed at relatively low levels in healthy tissue and significantly upregulated during development, injury, and wound healing. $\alpha_v \beta_6$ is upregulated on cancers of epithelial origin, including colon cancer, squamous cell cancer, ovarian cancer, and breast cancer.

Murine $\alpha v \beta 6$ antibodies have been shown to be able to effectively inhibit tumor growth in a human tumor xenograft model. Furthermore, several murine $\alpha v \beta 6$ antibodies have been shown to be effective in preventing fibrosis of the kidney and lung. However, murine antibodies are unsuitable for treatment of human subjects because murine antibodies can evoke anti-mouse immunoglobulin antibody production in the human subject's body. Reduction of the immunogenicity of therapeutic antibodies is desirable because induction of an immune response can cause a spectrum of adverse effects in a subject, ranging from accelerated elimination of the therapeutic antibody with consequent loss of efficacy to fatal anaphylaxis at the most extreme.

Accordingly, there is a need to develop $\alpha v \beta 6$ antibodies that are less antigenic in humans and that are useful in the treatment of diseases involved in the $\alpha v \beta 6$ pathway, such as fibrosis and cancers.

SUMMARY

This disclosure features antibodies and antigen-binding fragments thereof that specifically bind to $\alpha v \beta 6$ and their use to treat or prevent $\alpha v \beta 6$-mediated diseases or conditions such as fibrosis and cancer.

In one aspect, the application discloses an isolated antibody or an antigen-binding fragment thereof that specifically binds to $\alpha v \beta 6$, wherein the antibody or the antigen-binding fragment thereof comprises a heavy chain variable region that is at least 93% identical to the amino acid sequence set forth in SEQ ID NO:1. In certain embodiments, the antibody or an antigen-binding fragment thereof comprises a heavy chain variable region that is at least 94%, at least 95%, at least 96%, at least 97%, at least 98%, at least 99% or 100% identical to the amino acid sequence set forth in SEQ ID NO:1. In certain embodiments, any of the above antibodies or antigen-binding fragments thereof further comprises a light chain variable region that is at least 95%, at least 96%, at least 97%, at least 98%, at least 99% or 100% identical to the amino acid sequence set forth in SEQ ID NO:9. In a specific embodiment, the antibody or an antigen-binding fragment thereof comprises a heavy chain variable region that comprises the amino acid sequence set forth in SEQ ID NO:1 and a light chain variable region that comprises the amino acid sequence set forth in SEQ ID NO:9. In certain embodiments of this aspect, the antibody or an antigen-binding fragment thereof comprises a heavy chain variable region that is at least 94%, at least 95%, at least 96%, at least 97%, at least 98%, at least 99% or 100% identical to the amino acid sequence set forth in SEQ ID NO:1 and further comprises a light chain variable region that is at least 92%, at least 93%, at least 94%, at least 95%, at least 96%, at least 97%, at least 98%, at least 99% or 100% identical to the amino acid sequence set forth in SEQ ID NO:11. In a specific embodiment, the antibody or an antigen-binding fragment thereof comprises a heavy chain variable region that comprises the amino acid sequence set forth in SEQ ID NO:1 and a light chain variable region that comprises the amino acid sequence set forth in SEQ ID NO:11. In certain embodiments of this aspect, the antibody or an antigen-binding fragment thereof comprises a heavy chain variable region that is at least 94%, at least 95%, at least 96%, at least 97%, at least 98%, at least 99%, or 100% identical to the amino acid sequence set forth in SEQ ID NO:1 and further comprises a light chain variable region that is at least 91%, at least 92%, at least 93%, at least 94%, at least 95%, at least 96%, at least 97%, at least 98%, at least 99%, or 100% identical to the amino acid sequence set forth in SEQ ID NO:13. In a specific embodiment, the antibody or an antigen-binding fragment thereof comprises a heavy chain variable region that comprises the amino acid sequence set forth in SEQ ID NO:1 and a light chain variable region that comprises the amino acid sequence set forth in SEQ ID NO:13. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer (i.e., 2, 1, or zero) amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer (i.e., 2, 1, or zero) amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer (i.e., 2, 1, or zero) amino acid positions; the heavy chain CDR 2 comprises or consists of the amino acid sequence set forth in SEQ ID NO: 60 or the amino acid sequence set forth in SEQ ID NO: 60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer amino acid positions; the heavy chain CDR 2 comprises or consists of the amino acid sequence set forth in SEQ ID NO: 60 or the amino acid sequence set forth in SEQ ID NO:60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer (i.e., 2, 1, or zero) amino acid positions; the heavy chain CDR 2 comprises or consists of the amino acid sequence set forth in SEQ ID NO: 62 or the amino acid sequence set forth in SEQ ID NO: 62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer amino acid positions; the heavy chain CDR 2 comprises or consists of the amino acid sequence set forth in SEQ ID NO: 62 or the amino acid sequence set forth in SEQ ID NO:62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions; and light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63; and light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments, the antibody has an isotype selected from the group consisting of IgG1, IgG2, IgG3, and IgG4. In certain embodiments, the antigen-binding fragment is selected from the group consisting of an Fab, an Fab', an F(ab')2, an Fv, a diabody, an scFv, and an sc(Fv)2. In certain embodiments, the antibody or antigen-binding fragment thereof is conjugated to a substance selected from the group consisting of a toxin, a radionuclide, a fluorescent label, polyethylene glycol, and a cytotoxic agent. In certain embodiments, the antibody or antigen-binding fragment thereof is conjugated to an agent that is useful in treating or preventing the condition the antibody or antigen-binding fragment thereof is being used to treat or prevent. Examples of such agents include microRNAs, siRNAs, anti-miRs, small molecule drugs, and other chemical moieties. In some embodiments, the antibody or the antigen-binding fragment thereof is formulated with a pharmaceutically acceptable carrier as a pharmaceutical composition. In some embodiments, the antibody or the antigen-binding fragment thereof is used to treat a cancer in a human subject in need thereof, comprising administering to the human subject the antibody or the antigen-binding fragment thereof. In some embodiments where the antibody or the antigen-binding fragment thereof is used to treat cancer, it is conjugated to a cytotoxic agent. In some embodiments where the antibody or the antigen-binding fragment thereof is used to treat cancer, it is conjugated to a miRNA, siRNA, anti-miR, or small molecule drug that is useful in treating that particular cancer. In some embodiments, the antibody or the antigen-binding fragment thereof is administered to a human subject having a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer. In some embodiments, the antibody or the antigen-binding fragment thereof is used to treat or prevent a fibrotic disease in a human subject in need thereof, comprising administering to the human subject the antibody or the antigen-binding fragment thereof. In some embodiments, the fibrotic disease is lung fibrosis, kidney fibrosis, or liver fibrosis. In a particular embodiment, the lung fibrosis is idiopathic pulmonary fibrosis. In a particular embodiment, the lung fibrosis is usual interstitial pneumonia (UIP). In certain embodiments, the human subject with kidney fibrosis has diabetes or focal segmental glomerular sclerosis (FSGS). In some embodiments, the antibody or the antigen-binding fragment thereof is used to treat or prevent a condition such as acute lung injury, acute kidney injury, scleroderma, or Alport's syndrome in a human subject in need thereof, comprising administering to the human subject the antibody or the antigen-binding fragment thereof. In some embodiments, the antibody or the antigen-binding fragment thereof is used to treat or prevent an injury to an epithelium in a human subject in need thereof, comprising administering to the human subject the antibody or the antigen-binding fragment thereof. In certain embodiments, the injury to the epithelium is acute tissue injury of the lung, acute tissue injury of the kidney, or acute tissue injury of the liver. In some embodiments, the antibody or the antigen-binding fragment thereof is used to treat or prevent acute exacerbations of idiopathic pulmonary fibrosis in a human subject in need thereof, comprising administering to the human subject the antibody or the antigen-binding fragment thereof. In some embodiments, the antibody or the antigen-binding fragment thereof is used to treat or prevent a viral infection wherein the viral infection proceeds, at least in part, due to an interaction between a viral RGD-containing protein and αvβ6. In certain embodiments, the antibodies or antigen binding fragments of this aspect inhibit αvβ6 binding to LAP of TGF-β, inhibit αvβ6 binding to RGD-motif containing ligands of αvβ6 (e.g., tenascin, fibronectin), inhibit TGF-β signaling, and/or inhibit TGF-β activation.

In another aspect, the application discloses an isolated antibody or an antigen-binding fragment thereof that specifically binds to αvβ6, wherein the antibody or the antigen-binding fragment thereof comprises a heavy chain variable region that is at least 87% identical to the amino acid sequence set forth in SEQ ID NO:3. In certain embodiments, the antibody or an antigen-binding fragment thereof comprises a heavy chain variable region that is at least 88%, at least 89%, at least 90%, at least 91%, at least 92%, at least 93%, at least 94%, at least 95%, at least 96%, at least 97%, at least 98%, at least 99% or 100% identical to the amino acid sequence set forth in SEQ ID NO:3. In certain embodiments, any of the above antibodies or antigen-binding fragments thereof further comprises a light chain variable region that is at least 95%, at least 96%, at least 97%, at least 98%, at least 99% or 100% identical to the amino acid sequence set forth in SEQ ID NO:9. In a specific embodiment, the antibody or an antigen-binding fragment thereof comprises a heavy chain variable region that comprises the amino acid sequence set forth in SEQ ID NO:3 and a light chain variable region that comprises the amino acid sequence set forth in SEQ ID NO:9. In certain embodiments of this aspect, the antibody or an antigen-binding fragment thereof comprises a heavy chain variable region that is at least 88%, at least 89%, at least 90%, at least 91%, at least 92%, at least 93%, at least 94%, at least 95%, at least 96%, at least 97%, at least 98%, at least 99% or 100% identical to the amino acid sequence set forth in SEQ ID NO:3 and further comprises a light chain variable region that is at least 92%, at least 93%, at least 94%, at least 95%, at least 96%, at least 97%, at least 98%, at least 99% or 100% identical to the amino acid sequence set forth in SEQ ID NO:11. In a specific embodiment, the antibody or an antigen-binding fragment thereof comprises a heavy chain variable region that comprises the amino acid sequence set forth in SEQ ID NO:3 and a light chain variable region that comprises the amino acid sequence set forth in SEQ ID NO:11. In certain embodiments of this aspect, the antibody or an antigen-binding fragment thereof comprises a heavy chain variable region that is at least 88%, at least 89%, at least 90%, at least 91%, at least 92%, at least 93%, at least 94%, at least 95%, at least 96%, at least 97%, at least 98%, at least 99%, or 100% identical to the amino acid sequence set forth in SEQ ID NO:3 and further comprises a light chain variable region that is at least 91%, at least 92%, at least 93%, at least 94%, at least 95%, at least 96%, at least 97%, at least 98%, at least 99%, or 100% identical to the amino acid sequence set forth in SEQ ID NO:13. In a specific embodiment, the antibody or an antigen-binding fragment thereof comprises a heavy chain variable region that comprises the amino acid sequence set forth in SEQ ID NO:3 and a light chain variable region that comprises the amino acid sequence set forth in SEQ ID NO:13. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer (i.e., 2, 1, or zero) amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer (i.e., 2, 1, or zero) amino acid positions; the heavy chain CDR 2 comprises or consists of the amino acid sequence set forth in SEQ ID NO: 60 or the amino acid sequence set forth in SEQ ID NO: 60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer amino acid positions; the heavy chain CDR 2 comprises or consists of the amino acid sequence set forth in SEQ ID NO: 60 or the amino acid sequence set forth in SEQ ID NO:60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer (i.e., 2, 1, or zero) amino acid positions; the heavy chain CDR 2 comprises or consists of the amino acid sequence set forth in SEQ ID NO: 62 or the amino acid sequence set forth in SEQ ID NO: 62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer amino acid positions; the heavy chain CDR 2 comprises or consists of the amino acid sequence set forth in SEQ ID NO: 62 or the amino acid sequence set forth in SEQ ID NO:62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions; and light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63; and light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments, the antibody has an isotype selected from the group consisting of IgG1, IgG2, IgG3, and IgG4. In certain embodiments, the antigen-binding fragment is selected from the group consisting of an Fab, an Fab', an F(ab')2, an Fv, a diabody, an scFv, and an sc(Fv)2. In certain embodiments, the antibody or antigen-binding fragment thereof is conjugated to a substance selected from the group consisting of a toxin, a radionuclide, a fluorescent label, polyethylene glycol, and a cytotoxic agent. In certain embodiments, the antibody or antigen-binding fragment thereof is conjugated to an agent that is useful in treating or preventing the condition the antibody or antigen-binding fragment thereof is being used to treat or prevent. Examples of such agents include microRNAs, siRNAs, anti-miRs, small molecule drugs, and other chemical moieties. In some embodiments, the antibody or the antigen-binding fragment thereof is formulated with a pharmaceutically acceptable carrier as a pharmaceutical composition. In some embodiments, the antibody or the antigen-binding fragment thereof is used to treat a cancer in a human subject in need thereof, comprising administering to the human subject the antibody or the antigen-binding fragment thereof. In some embodiments where the antibody or the antigen-binding fragment thereof is used to treat cancer, it is conjugated to a cytotoxic agent. In some embodiments where the antibody or the antigen-binding fragment thereof is used to treat cancer, it is conjugated to a miRNA, siRNA, anti-miR, or small molecule drug that is useful in treating that particular cancer. In some embodiments, the antibody or the antigen-binding fragment thereof is administered to a human subject having a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer. In some embodiments, the antibody or the antigen-binding fragment thereof is used to treat or prevent a fibrotic disease in a human subject in need thereof, comprising administering to the human subject the antibody or the antigen-binding fragment thereof. In some embodiments, the fibrotic disease is lung fibrosis, kidney fibrosis, or liver fibrosis. In a particular embodiment, the lung fibrosis is idiopathic pulmonary fibrosis. In a particular embodiment, the lung fibrosis is usual interstitial pneumonia (UIP). In certain embodiments, the human subject with kidney fibrosis has diabetes or focal segmental glomerular sclerosis (FSGS). In some embodiments, the antibody or the antigen-binding fragment thereof is used to treat or prevent a condition such as acute lung injury, acute kidney injury, scleroderma, or Alport's syndrome in a human subject in need thereof, comprising administering to the human subject the antibody or the antigen-binding fragment thereof. In some embodiments, the antibody or the antigen-binding fragment thereof is used to treat or prevent injury to an epithelium in a human subject in need thereof, comprising administering to the human subject the antibody or the antigen-binding fragment thereof. In certain embodiments, the injury to the epithelium is acute tissue injury of the lung, acute tissue injury of the kidney, or acute tissue injury of the liver. In some embodiments, the antibody or the antigen-binding fragment thereof is used to treat or prevent acute exacerbations of idiopathic pulmonary fibrosis in a human subject in need thereof, comprising administering to the human subject the antibody or the antigen-binding fragment thereof. In some embodiments, the antibody or the antigen-binding fragment thereof is used to treat or prevent a viral infection wherein the viral infection proceeds, at least in part, due to an interaction between a viral RGD-containing protein and $\alpha v\beta 6$. In certain embodiments, the antibodies or antigen binding fragments of this aspect inhibit $\alpha v\beta 6$ binding to LAP of TGF-$\beta$, inhibit $\alpha v\beta 6$ binding to RGD-motif containing ligands of $\alpha v\beta 6$ (e.g., tenascin, fibronectin), inhibit TGF-$\beta$ signaling, and/or inhibit TGF-$\beta$ activation.

In a further aspect, the application discloses an isolated antibody or an antigen-binding fragment thereof that specifically binds to $\alpha v\beta 6$, wherein the antibody or the antigen-binding fragment thereof comprises a heavy chain variable region that is at least 86% identical to the amino acid sequence set forth in SEQ ID NO:5. In certain embodiments, the antibody or an antigen-binding fragment thereof comprises a heavy chain variable region that is at least 87%, at least 88%, at least 89%, at least 90%, at least 91%, at least 92%, at least 93%, at least 94%, at least 95%, at least 96%, at least 97%, at least 98%, at least 99% or 100% identical to the amino acid sequence set forth in SEQ ID NO:5. In certain embodiments, any of the above antibodies or antigen-binding fragments thereof further comprises a light chain variable region that is at least 95%, at least 96%, at least 97%, at least 98%, at least 99% or 100% identical to the amino acid sequence set forth in SEQ ID NO:9. In a specific embodiment, the antibody or an antigen-binding fragment thereof comprises a heavy chain variable region that comprises the amino acid sequence set forth in SEQ ID NO:5 and a light chain variable region that comprises the amino acid sequence set forth in SEQ ID NO:9. In certain embodiments of this aspect, the antibody or an antigen-binding fragment thereof comprises a heavy chain variable region that is at least 87%, at least 88%, at least 89%, at least 90%, at least 91%, at least 92%, at least 93%, at least 94%, at least 95%, at least 96%, at least 97%, at least 98%, at least 99% or 100% identical to the amino acid sequence set forth in SEQ ID NO:5 and further comprises a light chain variable region that is at least 92%, at least 93%, at least 94%, at least 95%, at least 96%, at least 97%, at least 98%, at least 99% or 100% identical to the amino acid sequence set forth in SEQ ID NO:11. In a specific embodiment, the antibody or an antigen-binding fragment thereof comprises a heavy chain variable region that comprises the amino acid sequence set forth in SEQ ID NO:5 and a light chain variable region that comprises the amino acid sequence set forth in SEQ ID NO:11. In certain embodiments of this aspect, the antibody or an antigen-binding fragment thereof comprises a heavy chain variable region that is at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence set forth in SEQ ID NO:5 and further comprises a light chain variable region that is at least 91%, at least 92%, at least 93%, at least 94%, at least 95%, at least 96%, at least 97%, at least 98%, at least 99%, or 100% identical to the amino acid sequence set forth in SEQ ID NO:13. In a specific embodiment, the antibody or an antigen-binding fragment thereof comprises a heavy chain variable region that comprises the amino acid sequence set forth in SEQ ID NO:5 and a light chain variable region that comprises the amino acid sequence set forth in SEQ ID NO:13. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer (i.e., 2, 1, or zero) amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer (i.e., 2, 1, or zero) amino acid positions; the heavy chain CDR 2 comprises or consists of the amino acid sequence set forth in SEQ ID NO: 60 or the amino acid sequence set forth in SEQ ID NO: 60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer amino acid positions; the heavy chain CDR 2 comprises or consists of the amino acid sequence set forth in SEQ ID NO: 60 or the amino acid sequence set forth in SEQ ID NO:60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer (i.e., 2, 1, or zero) amino acid positions; the heavy chain CDR 2 comprises or consists of the amino acid sequence set forth in SEQ ID NO: 62 or the amino acid sequence set forth in SEQ ID NO: 62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer amino acid positions; the heavy chain CDR 2 comprises or consists of the amino acid sequence set forth in SEQ ID NO: 62 or the amino acid sequence set forth in SEQ ID NO:62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions; and light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63; and light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments, the antibody has an isotype selected from the group consisting of IgG1, IgG2, IgG3, and IgG4. In certain embodiments, the antigen-binding fragment is selected from the group consisting of an Fab, an Fab', an F(ab')2, an Fv, a diabody, an scFv, and an sc(Fv)2. In certain embodiments, the antibody or antigen-binding fragment thereof is conjugated to a substance selected from the group consisting of a toxin, a radionuclide, a fluorescent label, polyethylene glycol, and a cytotoxic agent. In certain embodiments, the antibody or antigen-binding fragment thereof is conjugated to an agent that is useful in treating or preventing the condition the antibody or antigen-binding fragment thereof is being used to treat or prevent. Examples of such agents include microRNAs, siRNAs, anti-miRs, small molecule drugs, and other chemical moieties. In some embodiments, the antibody or the antigen-binding fragment thereof is formulated with a pharmaceutically acceptable carrier as a pharmaceutical composition. In some embodiments, the antibody or the antigen-binding fragment thereof is used to treat a cancer in a human subject in need thereof, comprising administering to the human subject the antibody or the antigen-binding fragment thereof. In some embodiments where the antibody or the antigen-binding fragment thereof is used to treat cancer, it is conjugated to a cytotoxic agent. In some embodiments where the antibody or the antigen-binding fragment thereof is used to treat cancer, it is conjugated to a miRNA, siRNA, anti-miR, or small molecule drug that is useful in treating that particular cancer. In some embodiments, the antibody or the antigen-binding fragment thereof is administered to a human subject having a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer. In some embodiments, the antibody or the antigen-binding fragment thereof is used to treat or prevent a fibrotic disease in a human subject in need thereof, comprising administering to the human subject the antibody or the antigen-binding fragment thereof. In some embodiments, the fibrotic disease is lung fibrosis, kidney fibrosis, or liver fibrosis. In a particular embodiment, the lung fibrosis is idiopathic pulmonary fibrosis. In a particular embodiment, the lung fibrosis is usual interstitial pneumonia (UIP). In certain embodiments, the human subject with kidney fibrosis has diabetes or focal segmental glomerular sclerosis (FSGS). In some embodiments, the antibody or the antigen-binding fragment thereof is used to treat or prevent a condition such as acute lung injury, acute kidney injury, scleroderma, or Alport's syndrome in a human subject in need thereof, comprising administering to the human subject the antibody or the antigen-binding fragment thereof. In some embodiments, the antibody or the antigen-binding fragment thereof is used to treat or prevent injury to an epithelium in a human subject in need thereof, comprising administering to the human subject the antibody or the antigen-binding fragment thereof. In certain embodiments, the injury to the epithelium is acute tissue injury of the lung, acute tissue injury of the kidney, or acute tissue injury of the liver. In some embodiments, the antibody or the antigen-binding fragment thereof is used to treat or prevent acute exacerbations of idiopathic pulmonary fibrosis in a human subject in need thereof, comprising administering to the human subject the antibody or the antigen-binding fragment thereof. In some embodiments, the antibody or the antigen-binding fragment thereof is used to treat or prevent a viral infection wherein the viral infection proceeds, at least in part, due to an interaction between a viral RGD-containing protein and αvβ6. In certain embodiments, the antibodies or antigen binding fragments of this aspect inhibit αvβ6 binding to LAP of TGF-β, inhibit αvβ6 binding to RGD-motif containing ligands of αvβ6 (e.g., tenascin, fibronectin), inhibit TGF-β signaling, and/or inhibit TGF-β activation.

In another aspect, the application discloses an isolated antibody or an antigen-binding fragment thereof that specifically binds to αvβ6, wherein the antibody or the antigen-binding fragment thereof comprises a heavy chain variable region that is at least 85% identical to the amino acid sequence set forth in SEQ ID NO:7. In certain embodiments, the antibody or an antigen-binding fragment thereof comprises a heavy chain variable region that is at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the amino acid sequence set forth in SEQ ID NO:7. In certain embodiments, any of the above antibodies or antigen-binding fragments thereof further comprises a light chain variable region that is at least 95%, at least 96%, at least 97%, at least 98%, at least 99% or 100% identical to the amino acid sequence set forth in SEQ ID NO:9. In a specific embodiment, the antibody or an antigen-binding fragment thereof comprises a heavy chain variable region that comprises the amino acid sequence set forth in SEQ ID NO:7 and a light chain variable region that comprises the amino acid sequence set forth in SEQ ID NO:9. In certain embodiments of this aspect, the antibody or an antigen-binding fragment thereof comprises a heavy chain variable region that is at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the amino acid sequence set forth in SEQ ID NO:7 and further comprises a light chain variable region that is at least 92%, at least 93%, at least 94%, at least 95%, at least 96%, at least 97%, at least 98%, at least 99% or 100% identical to the amino acid sequence set forth in SEQ ID NO:11. In a specific embodiment, the antibody or an antigen-binding fragment thereof comprises a heavy chain variable region that comprises the amino acid sequence set forth in SEQ ID NO:7 and a light chain variable region that comprises the amino acid sequence set forth in SEQ ID NO:11. In certain embodiments of this aspect, the antibody or an antigen-binding fragment thereof comprises a heavy chain variable region that is at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence set forth in SEQ ID NO:7 and further comprises a light chain variable region that is at least 91%, at least 92%, at least 93%, at least 94%, at least 95%, at least 96%, at least 97%, at least 98%, at least 99%, or 100% identical to the amino acid sequence set forth in SEQ ID NO:13. In a specific embodiment, the antibody or an antigen-binding fragment thereof comprises a heavy chain variable region that comprises the amino acid sequence set forth in SEQ ID NO:7 and a light chain variable region that comprises the amino acid sequence set forth in SEQ ID NO:13. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer (i.e., 2, 1, or zero) amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer (i.e., 2, 1, or zero) amino acid positions; the heavy chain CDR 2 comprises or consists of the amino acid sequence set forth in SEQ ID NO: 60 or the amino acid sequence set forth in SEQ ID NO: 60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer amino acid positions; the heavy chain CDR 2 comprises or consists of the amino acid sequence set forth in SEQ ID NO: 60 or the amino acid sequence set forth in SEQ ID NO:60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO:

61 with a substitution at two or fewer (i.e., 2, 1, or zero) amino acid positions; the heavy chain CDR 2 comprises or consists of the amino acid sequence set forth in SEQ ID NO: 62 or the amino acid sequence set forth in SEQ ID NO: 62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer amino acid positions; the heavy chain CDR 2 comprises or consists of the amino acid sequence set forth in SEQ ID NO: 62 or the amino acid sequence set forth in SEQ ID NO:62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions; and light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63; and light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments, the antibody has an isotype selected from the group consisting of IgG1, IgG2, IgG3, and IgG4. In certain embodiments, the antigen-binding fragment is selected from the group consisting of an Fab, an Fab', an F(ab')2, an Fv, a diabody, an scFv, and an sc(Fv)2. In certain embodiments, the antibody or antigen-binding fragment thereof is conjugated to a substance selected from the group consisting of a toxin, a radionuclide, a fluorescent label, polyethylene glycol, and a cytotoxic agent. In certain embodiments, the antibody or antigen-binding fragment thereof is conjugated to an agent that is useful in treating or preventing the condition the antibody or antigen-binding fragment thereof is being used to treat or prevent. Examples of such agents include microRNAs, siRNAs, anti-miRs, small molecule drugs, and other chemical moieties. In some embodiments, the antibody or the antigen-binding fragment thereof is formulated with a pharmaceutically acceptable carrier as a pharmaceutical composition. In some embodiments, the antibody or the antigen-binding fragment thereof is used to treat a cancer in a human subject in need thereof, comprising administering to the human subject the antibody or the antigen-binding fragment thereof. In some embodiments where the antibody or the antigen-binding fragment thereof is used to treat cancer, it is conjugated to a cytotoxic agent. In some embodiments where the antibody or the antigen-binding fragment thereof is used to treat cancer, it is conjugated to a miRNA, siRNA, anti-miR, or small molecule drug that is useful in treating that particular cancer. In some embodiments, the antibody or the antigen-binding fragment thereof is administered to a human subject having a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer. In some embodiments, the antibody or the antigen-binding fragment thereof is used to treat or prevent a fibrotic disease in a human subject in need thereof, comprising administering to the human subject the antibody or the antigen-binding fragment thereof. In some embodiments, the fibrotic disease is lung fibrosis, kidney fibrosis, or liver fibrosis. In a particular embodiment, the lung fibrosis is idiopathic pulmonary fibrosis. In a particular embodiment, the lung fibrosis is usual interstitial pneumonia (UIP). In certain embodiments, the human subject with kidney fibrosis has diabetes or focal segmental glomerular sclerosis (FSGS). In some embodiments, the antibody or the antigen-binding fragment thereof is used to treat or prevent a condition such as acute lung injury, acute kidney injury, scleroderma, or Alport's syndrome in a human subject in need thereof, comprising administering to the human subject the antibody or the antigen-binding fragment thereof. In some embodiments, the antibody or the antigen-binding fragment thereof is used to treat or prevent injury to an epithelium in a human subject in need thereof, comprising administering to the human subject the antibody or the antigen-binding fragment thereof. In certain embodiments, the injury to the epithelium is acute tissue injury of the lung, acute tissue injury of the kidney, or acute tissue injury of the liver. In some embodiments, the antibody or the antigen-binding fragment thereof is used to treat or prevent acute exacerbations of idiopathic pulmonary fibrosis in a human subject in need thereof, comprising administering to the human subject the antibody or the antigen-binding fragment thereof. In some embodiments, the antibody or the antigen-binding fragment thereof is used to treat or prevent a viral infection wherein the viral infection proceeds, at least in part, due to an interaction between a viral RGD-containing protein and αvβ6. In certain embodiments, the antibodies or antigen binding fragments of this aspect inhibit αvβ6 binding to LAP of TGF-β, inhibit αvβ6 binding to RGD-motif containing ligands of αvβ6 (e.g., tenascin, fibronectin), inhibit TGF-β signaling, and/or inhibit TGF-β activation.

In another aspect, the application discloses an isolated antibody or an antigen-binding fragment thereof that specifically binds to αvβ6, wherein the antibody or the antigen-binding fragment thereof comprises a heavy chain variable region that is at least 95% identical to the amino acid sequence set forth in SEQ ID NO: 50. In certain embodiments, the antibody or an antigen-binding fragment thereof comprises a heavy chain variable region that is at least 96%, at least 97%, at least 98%, at least 99% or 100% identical to the amino acid sequence set forth in SEQ ID NO: 50. In certain embodiments, any of the above antibodies or antigen-binding fragments thereof further comprises a light chain variable region that is at least 95%, at least 96%, at least 97%, at least 98%, at least 99% or 100% identical to the amino acid sequence set forth in SEQ ID NO:9. In a specific embodiment, the antibody or an antigen-binding fragment thereof comprises a heavy chain variable region that comprises the amino acid sequence set forth in SEQ ID NO:50 and a light chain variable region that comprises the amino acid sequence set forth in SEQ ID NO:9. In certain embodiments of this aspect, the antibody or an antigen-binding fragment thereof comprises a heavy chain variable region that is at least 95%, at least 96%, at least 97%, at least 98%, at least 99% or 100% identical to the amino acid sequence set forth in SEQ ID NO:50 and further comprises a light chain variable region that is at least 92%, at least 93%, at least 94%, at least 95%, at least 96%, at least 97%, at least 98%, at least 99% or 100% identical to the amino acid sequence set forth in SEQ ID NO:11. In a specific embodiment, the antibody or an antigen-binding fragment thereof comprises a heavy chain variable region that comprises the amino acid sequence set forth in SEQ ID NO: 50 and a light chain variable region that comprises the amino acid sequence set forth in SEQ ID NO:11. In certain embodiments of this aspect, the antibody or an antigen-binding fragment thereof comprises a heavy chain variable region that is at least 95%, at least 96%, at least 97%, at least 98%, at least 99%, or 100% identical to the amino acid sequence set forth in SEQ ID NO: 50 and further comprises a light chain variable region that is at least 91%, at least 92%, at least 93%, at least 94%, at least 95%, at least 96%, at least 97%, at least 98%, at least 99%, or 100% identical to the amino acid sequence set forth in SEQ ID NO:13. In a specific embodiment, the antibody or an antigen-binding fragment thereof comprises a heavy chain variable region that comprises the amino acid sequence set forth in SEQ ID NO:50 and a light chain variable region that comprises the amino acid sequence set forth in SEQ ID NO:13. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 or consists of comprises the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer (i.e., 2, 1, or zero) amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer (i.e., 2, 1, or zero) amino acid positions; the heavy chain CDR 2 comprises or consists of the amino acid sequence set forth in SEQ ID NO: 60 or the amino acid sequence set forth in SEQ ID NO: 60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer amino acid positions; the heavy chain CDR 2 comprises or consists of the amino acid sequence set forth in SEQ ID NO: 60 or the amino acid sequence set forth in SEQ ID NO:60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer (i.e., 2, 1, or zero) amino acid positions; the heavy chain CDR 2 comprises or consists of the amino acid sequence set forth in SEQ ID NO: 62 or the amino acid sequence set forth in SEQ ID NO: 62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer amino acid positions; the heavy chain CDR 2 comprises or consists of the amino acid sequence set forth in SEQ ID NO: 62 or the amino acid sequence set forth in SEQ ID NO:62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions; and light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63; and light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments, the antibody has an isotype selected from the group consisting of IgG1, IgG2, IgG3, and IgG4. In certain embodiments, the antigen-binding fragment is selected from the group consisting of an Fab, an Fab', an F(ab')2, an Fv, a diabody, an scFv, and an sc(Fv)2. In certain embodiments, the antibody or antigen-binding fragment thereof is conjugated to a substance selected from the group consisting of a toxin, a radionuclide, a fluorescent label, polyethylene glycol, and a cytotoxic agent. In certain embodiments, the antibody or antigen-binding fragment thereof is conjugated to an agent that is useful in treating or preventing the condition the antibody or antigen-binding fragment thereof is being used to treat or prevent. Examples of such agents include microRNAs, siRNAs, anti-miRs, small molecule drugs, and other chemical moieties. In some embodiments, the antibody or the antigen-binding fragment thereof is formulated with a pharmaceutically acceptable carrier as a pharmaceutical composition. In some embodiments, the antibody or the antigen-binding fragment thereof is used to treat a cancer in a human subject in need thereof, comprising administering to the human subject the antibody or the antigen-binding fragment thereof. In some embodiments where the antibody or the antigen-binding fragment thereof is used to treat cancer, it is conjugated to a cytotoxic agent. In some embodiments where the antibody or the antigen-binding fragment thereof is used to treat cancer, it is conjugated to a miRNA, siRNA, anti-miR, or small molecule drug that is useful in treating that particular cancer. In some embodiments, the antibody or the antigen-binding fragment thereof is administered to a human subject having a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer. In some embodiments, the antibody or the antigen-binding fragment thereof is used to treat or prevent a fibrotic disease in a human subject in need thereof, comprising administering to the human subject the antibody or the antigen-binding fragment thereof. In some embodiments, the fibrotic disease is lung fibrosis, kidney fibrosis, or liver fibrosis. In a particular embodiment, the lung fibrosis is idiopathic pulmonary fibrosis. In a particular embodiment, the lung fibrosis is usual interstitial pneumonia (UIP). In certain embodiments, the human subject with kidney fibrosis has diabetes or focal segmental glomerular sclerosis (FSGS). In some embodiments, the antibody or the antigen-binding fragment thereof is used to treat or prevent a condition such as acute lung injury, acute kidney injury, scleroderma, or Alport's syndrome in a human subject in need thereof, comprising administering to the human subject the antibody or the antigen-binding fragment thereof. In some embodiments, the antibody or the antigen-binding fragment thereof is used to treat or prevent injury to an epithelium in a human subject in need thereof, comprising administering to the human subject the antibody or the antigen-binding fragment thereof. In certain embodiments, the injury to the epithelium is acute tissue injury of the lung, acute tissue injury of the kidney, or acute tissue injury of the liver. In some embodiments, the antibody or the antigen-binding fragment thereof is used to treat or prevent acute exacerbations of idiopathic pulmonary fibrosis in a human subject in need thereof, comprising administering to the human subject the antibody or the antigen-binding fragment thereof. In some embodiments, the antibody or the antigen-binding fragment thereof is used to treat or prevent a viral infection wherein the viral infection proceeds, at least in part, due to an interaction between a viral RGD-containing protein and αvβ6. In certain embodiments, the antibodies or antigen binding fragments of this aspect inhibit αvβ6 binding to LAP of TGF-β, inhibit αvβ6 binding to RGD-motif containing ligands of αvβ6 (e.g., tenascin, fibronectin), inhibit TGF-β signaling, and/or inhibit TGF-β activation.

In a further aspect, the application discloses an isolated antibody or an antigen-binding fragment thereof that specifically binds to αvβ6, wherein the antibody or the antigen-binding fragment thereof comprises a heavy chain variable region that is at least 96.5% identical to the amino acid sequence set forth in SEQ ID NO: 52. In certain embodiments, the antibody or an antigen-binding fragment thereof comprises a heavy chain variable region that is at least 97%, at least 98%, at least 99% or 100% identical to the amino acid sequence set forth in SEQ ID NO: 52. In certain embodiments, any of the above antibodies or antigen-binding fragments thereof further comprises a light chain variable region that is at least 95%, at least 96%, at least 97%, at least 98%, at least 99% or 100% identical to the amino acid sequence set forth in SEQ ID NO:9. In a specific embodiment, the antibody or an antigen-binding fragment thereof comprises a heavy chain variable region that comprises the amino acid sequence set forth in SEQ ID NO: 52 and a light chain variable region that comprises the amino acid sequence set forth in SEQ ID NO:9. In certain embodiments of this aspect, the antibody or an antigen-binding fragment thereof comprises a heavy chain variable region that is at least 96.5%, at least 97%, at least 98%, at least 99% or 100% identical to the amino acid sequence set forth in SEQ ID NO:52 and further comprises a light chain variable region that is at least 92%, at least 93%, at least 94%, at least 95%, at least 96%, at least 97%, at least 98%, at least 99% or 100% identical to the amino acid sequence set forth in SEQ ID NO:11. In a specific embodiment, the antibody or an antigen-binding fragment thereof comprises a heavy chain variable region that comprises the amino acid sequence set forth in SEQ ID NO: 52 and a light chain variable region that comprises the amino acid sequence set forth in SEQ ID NO:11. In certain embodiments of this aspect, the antibody or an antigen-binding fragment thereof comprises a heavy chain variable region that is at least 96.5%, at least 97%, at least 98%, at least 99%, or 100% identical to the amino acid sequence set forth in SEQ ID NO:52 and further comprises a light chain variable region that is at least 91%, at least 92%, at least 93%, at least 94%, at least 95%, at least 96%, at least 97%, at least 98%, at least 99%, or 100% identical to the amino acid sequence set forth in SEQ ID NO:13. In a specific embodiment, the antibody or an antigen-binding fragment thereof comprises a heavy chain variable region that comprises the amino acid sequence set forth in SEQ ID NO:52 and a light chain variable region that comprises the amino acid sequence set forth in SEQ ID NO:13. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15 or the amino acid sequence set forth in SEQ ID NO: 15 with a substitution at two or fewer amino acid positions; the heavy chain CDR 2 comprises or consists of the amino acid sequence set forth in SEQ ID NO: 16 or the amino acid sequence set forth in SEQ ID NO: 16 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 15; the heavy chain CDR 2 comprises or consists of the amino acid sequence set forth in SEQ ID NO: 16; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer (i.e., 2, 1, or zero) amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57 or the amino acid sequence set forth in SEQ ID NO: 57 with a substitution at two or fewer amino acid positions; the heavy chain CDR 2 comprises or consists of the amino acid sequence set forth in SEQ ID NO: 58 or the amino acid sequence set forth in SEQ ID NO: 58 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 57; the heavy chain CDR 2 comprises or consists of the amino acid sequence set forth in SEQ ID NO: 58; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer (i.e., 2, 1, or zero) amino acid positions; the heavy chain CDR 2 comprises or consists of the amino acid sequence set forth in SEQ ID NO: 60 or the amino acid sequence set forth in SEQ ID NO: 60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59 or the amino acid sequence set forth in SEQ ID NO: 59 with a substitution at two or fewer amino acid positions; the heavy chain CDR 2 comprises or consists of the amino acid sequence set forth in SEQ ID NO: 60 or the amino acid sequence set forth in SEQ ID NO:60 with a substitution at two or fewer amino acid positions; and the heavy chain CDR 3 comprises or consists of the amino acid sequence set forth in SEQ ID NO: 17 or the amino acid sequence set forth in SEQ ID NO: 17 with a substitution at two or fewer amino acid positions; and light chain CDRs 1, 2 and 3 wherein the light chain CDR 1 comprises or consists of the amino acid sequence set forth in SEQ ID NO: 18 or the amino acid sequence set forth in SEQ ID NO: 18 with a substitution at two or fewer amino acid positions; the light chain CDR 2 comprises or consists of the amino acid sequence set forth in SEQ ID NO: 19 or the amino acid sequence set forth in SEQ ID NO: 19 with a substitution at two or fewer amino acid positions; and the light chain CDR 3 comprises or consists of the amino acid sequence set forth in SEQ ID NO: 20 or the amino acid sequence set forth in SEQ ID NO: 20 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 59; the heavy chain CDR 2 comprises or consists of the amino acid sequence set forth in SEQ ID NO: 60; and the heavy chain CDR 3 comprises or consists of the amino acid sequence set forth in SEQ ID NO: 17; and light chain CDRs 1, 2 and 3 wherein the light chain CDR 1 comprises or consists of the amino acid sequence set forth in SEQ ID NO: 18; the light chain CDR 2 comprises or consists of the amino acid sequence set forth in SEQ ID NO: 19; and the light chain CDR 3 comprises or consists of the amino acid sequence set forth in SEQ ID NO: 20. In certain embodiments of this aspect, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer (i.e., 2, 1, or zero) amino acid positions; the heavy chain CDR 2 comprises or consists of the amino acid sequence set forth in SEQ ID NO: 62 or the amino acid sequence set forth in SEQ ID NO: 62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions. In a specific embodiment, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63. In certain embodiments wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61 or the amino acid sequence set forth in SEQ ID NO: 61 with a substitution at two or fewer amino acid positions; the heavy chain CDR 2 comprises or consists of the amino acid sequence set forth in SEQ ID NO: 62 or the amino acid sequence set forth in SEQ ID NO:62 with a substitution at two or fewer amino acid positions; and the heavy chain CDR 3 comprises or consists of the amino acid sequence set forth in SEQ ID NO: 63 or the amino acid sequence set forth in SEQ ID NO: 63 with a substitution at two or fewer amino acid positions; and light chain CDRs 1, 2 and 3 wherein the light chain CDR 1 comprises or consists of the amino acid sequence set forth in SEQ ID NO: 64 or the amino acid sequence set forth in SEQ ID NO: 64 with a substitution at two or fewer amino acid positions; the light chain CDR 2 comprises or consists of the amino acid sequence set forth in SEQ ID NO: 65 or the amino acid sequence set forth in SEQ ID NO: 65 with a substitution at two or fewer amino acid positions; and the light chain CDR 3 comprises or consists of the amino acid sequence set forth in SEQ ID NO: 66 or the amino acid sequence set forth in SEQ ID NO: 66 with a substitution at two or fewer amino acid positions. In a specific embodiment wherein the antibody or antibody-binding fragment thereof comprises a heavy chain variable region and a light chain variable region, the antibody or the antigen-binding fragment thereof comprises heavy chain CDRs 1, 2 and 3 wherein the heavy chain CDR 1 comprises or consists of the amino acid sequence set forth in SEQ ID NO: 61; the heavy chain CDR 2 comprises or consists of the amino acid sequence set forth in SEQ ID NO: 62; and the heavy chain CDR 3 comprises or consists of the amino acid sequence set forth in SEQ ID NO: 63; and light chain CDRs 1, 2 and 3 wherein the light chain CDR 1 comprises or consists of the amino acid sequence set forth in SEQ ID NO: 64; the light chain CDR 2 comprises or consists of the amino acid sequence set forth in SEQ ID NO: 65; and the light chain CDR 3 comprises or consists of the amino acid sequence set forth in SEQ ID NO: 66. In certain embodiments, the antibody has an isotype selected from the group consisting of IgG1, IgG2, IgG3, and IgG4. In certain embodiments, the antigen-binding fragment is selected from the group consisting of an Fab, an Fab', an F(ab')2, an Fv, a diabody, an scFv, and an sc(Fv)2. In certain embodiments, the antibody or antigen-binding fragment thereof is conjugated to a substance selected from the group consisting of a toxin, a radionuclide, a fluorescent label, polyethylene glycol, and a cytotoxic agent. In certain embodiments, the antibody or antigen-binding fragment thereof is conjugated to an agent that is useful in treating or preventing the condition the antibody or antigen-binding fragment thereof is being used to treat or prevent. Examples of such agents include micro-RNAs, siRNAs, anti-miRs, small molecule drugs, and other chemical moieties. In some embodiments, the antibody or the antigen-binding fragment thereof is formulated with a pharmaceutically acceptable carrier as a pharmaceutical composition. In some embodiments, the antibody or the antigen-binding fragment thereof is used to treat a cancer in a human subject in need thereof, comprising administering to the human subject the antibody or the antigen-binding fragment thereof. In some embodiments where the antibody or the antigen-binding fragment thereof is used to treat cancer, it is conjugated to a cytotoxic agent. In some embodiments where the antibody or the antigen-binding fragment thereof is used to treat cancer, it is conjugated to a miRNA, siRNA, anti-miR, or small molecule drug that is useful in treating that particular cancer. In some embodiments, the antibody or the antigen-binding fragment thereof is administered to a human subject having a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer. In some embodiments, the antibody or the antigen-binding fragment thereof is used to treat or prevent a fibrotic disease in a human subject in need thereof, comprising administering to the human subject the antibody or the antigen-binding fragment thereof. In some embodiments, the fibrotic disease is lung fibrosis, kidney fibrosis, or liver fibrosis. In a particular embodiment, the lung fibrosis is idiopathic pulmonary fibrosis. In a particular embodiment, the lung fibrosis is usual interstitial pneumonia (UIP). In certain embodiments, the human subject with kidney fibrosis has diabetes or focal segmental glomerular sclerosis (FSGS). In some embodiments, the antibody or the antigen-binding fragment thereof is used to treat or prevent a condition such as acute lung injury, acute kidney injury, scleroderma, or Alport's syndrome in a human subject in need thereof, comprising administering to the human subject the antibody or the antigen-binding fragment thereof. In some embodiments, the antibody or the antigen-binding fragment thereof is used to treat or prevent injury to an epithelium in a human subject in need thereof, comprising administering to the human subject the antibody or the antigen-binding fragment thereof. In certain embodiments, the injury to the epithelium is acute tissue injury of the lung, acute tissue injury of the kidney, or acute tissue injury of the liver. In some embodiments, the antibody or the antigen-binding fragment thereof is used to treat or prevent acute exacerbations of idiopathic pulmonary fibrosis in a human subject in need thereof, comprising administering to the human subject the antibody or the antigen-binding fragment thereof. In some embodiments, the antibody or the antigen-binding fragment thereof is used to treat or prevent a viral infection wherein the viral infection proceeds, at least in part, due to an interaction between a viral RGD-containing protein and αvβ6. In certain embodiments, the antibodies or antigen binding fragments of this aspect inhibit αvβ6 binding to LAP of TGF-β, inhibit αvβ6 binding to RGD-motif containing ligands of αvβ6 (e.g., tenascin, fibronectin), inhibit TGF-β signaling, and/or inhibit TGF-β activation.

In another aspect, this application features an isolated nucleic acid comprising a nucleotide sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence set forth in SEQ ID NOs.: 2, 4, 6, 8, 51, or 53. The proteins encoded by these nucleic acids specifically bind to αvβ6. This disclosure also includes proteins encoded by any of the above nucleic acids. In addition, this disclosure includes recombinant vectors comprising any of the above nucleic acids. Furthermore, this application provides host cells comprising recombinant vectors comprising any of the above nucleic acids.

In another aspect, this application features an isolated nucleic acid comprising a nucleotide sequence that encodes a polypeptide comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an amino acid sequence set forth in SEQ ID NOs.: 1, 3, 5, 7, 50, or 52. The proteins encoded by these nucleic acids specifically bind to αvβ6. This disclosure also includes proteins encoded by any of the above nucleic acids. In addition, this disclosure includes recombinant vectors comprising any of the above nucleic acids. Furthermore, this application provides host cells comprising recombinant vectors comprising any of the above nucleic acids.

In another aspect, this application features an isolated nucleic acid comprising a nucleotide sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence set forth in SEQ ID NOs.: 10, 12, or 14. The proteins encoded by these nucleic acids when combined with one of the proteins of SEQ ID NOs: 1, 3, 5, 7, 50, or 52 specifically bind to αvβ6. This disclosure also includes proteins encoded by any of the above nucleic acids. In addition, this disclosure includes recombinant vectors comprising any of the above nucleic acids. Furthermore, this application provides host cells comprising recombinant vectors comprising any of the above nucleic acids.

In another aspect, this application features an isolated nucleic acid comprising a nucleotide sequence that encodes a polypeptide comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an amino acid sequence set forth in SEQ ID NOs.: 9, 11, or 13. The proteins encoded by these nucleic acids when combined with one of the proteins of SEQ ID NOs: 1, 3, 5, 7, 50, or 52 specifically bind to αvβ6. This disclosure also includes proteins encoded by any of the above nucleic acids. In addition, this disclosure includes recombinant vectors comprising any of the above nucleic acids. Furthermore, this application provides host cells comprising recombinant vectors comprising any of the above nucleic acids.

In yet another aspect, this disclosure features a method of preparing a humanized antibody comprising culturing a host cell comprising recombinant vectors comprising the nucleic acid sequence set forth in SEQ ID NO: 2 and the nucleic acid sequence set forth in any one of SEQ ID NOs: 10, 12, or 14, under conditions appropriate for expression of a humanized antibody, wherein humanized antibody chains are expressed and a humanized antibody is produced. In certain embodiments, the method further involves isolating the humanized antibody. In some embodiments, the host cell is a CHO cell.

In yet another aspect, this disclosure features a method of preparing a humanized antibody comprising culturing a host cell comprising recombinant vectors comprising the nucleic acid sequence set forth in SEQ ID NO: 4 and the nucleic acid sequence set forth in any one of SEQ ID NOs: 10, 12, or 14, under conditions appropriate for expression of a humanized antibody, wherein humanized antibody chains are expressed and a humanized antibody is produced. In certain embodiments, the method further involves isolating the humanized antibody. In certain embodiments, the method further involves conjugating the antibody with a cytotoxic agent. In some embodiments, the host cell is a CHO cell.

In yet another aspect, this disclosure features a method of preparing a humanized antibody comprising culturing a host cell comprising recombinant vectors comprising the nucleic acid sequence set forth in SEQ ID NO: 6 and the nucleic acid sequence set forth in any one of SEQ ID NOs: 10, 12, or 14, under conditions appropriate for expression of a humanized antibody, wherein humanized antibody chains are expressed and a humanized antibody is produced. In certain embodiments, the method further involves isolating the humanized antibody. In certain embodiments, the method further involves conjugating the antibody with a cytotoxic agent. In some embodiments, the host cell is a CHO cell.

In yet another aspect, this disclosure features a method of preparing a humanized antibody comprising culturing a host cell comprising recombinant vectors comprising the nucleic acid sequence set forth in SEQ ID NO: 8 and the nucleic acid sequence set forth in any one of SEQ ID NOs: 10, 12, or 14, under conditions appropriate for expression of a humanized antibody, wherein humanized antibody chains are expressed and a humanized antibody is produced. In certain embodiments, the method further involves isolating the humanized antibody. In certain embodiments, the method further involves conjugating the antibody with a cytotoxic agent. In some embodiments, the host cell is a CHO cell.

In yet another aspect, this disclosure features a method of preparing a humanized antibody comprising culturing a host cell comprising recombinant vectors comprising the nucleic acid sequence set forth in SEQ ID NO: 51 and the nucleic acid sequence set forth in any one of SEQ ID NOs: 10, 12, or 14, under conditions appropriate for expression of a humanized antibody, wherein humanized antibody chains are expressed and a humanized antibody is produced. In certain embodiments, the method further involves isolating the humanized antibody. In certain embodiments, the method further involves conjugating the antibody with a cytotoxic agent. In some embodiments, the host cell is a CHO cell.

In yet another aspect, this disclosure features a method of preparing a humanized antibody comprising culturing a host cell comprising recombinant vectors comprising the nucleic acid sequence set forth in SEQ ID NO: 53 and the nucleic acid sequence set forth in any one of SEQ ID NOs: 10, 12, or 14, under conditions appropriate for expression of a humanized antibody, wherein humanized antibody chains are expressed and a humanized antibody is produced. In certain embodiments, the method further involves isolating the humanized antibody. In certain embodiments, the method further involves conjugating the antibody with a cytotoxic agent. In some embodiments, the host cell is a CHO cell.

In another aspect, this disclosure features a method for diagnosing an αvβ6-mediated disorder in a human subject. The method comprises contacting a cell/tissue (obtained from the relevant organ/tissue for the disease being diagnosed) from the subject with an isolated antibody or an antigen-binding fragment thereof described herein. An increased level of expression of αvβ6 in the cell/tissue (as measured by, e.g., detecting the formation of a complex between the antibody or the antigen-binding fragment thereof and the cell or tissue) relative to a human subject not having the αvβ6-mediated disorder is indicative that the subject has the αvβ6-mediated disorder. In some embodiments, the αvβ6-mediated disorder is acute tissue injury (e.g., of lung, kidney, or liver), fibrosis (e.g., lung, liver, or kidney), or cancer (e.g., a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, or an endometrial cancer).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is an alignment of six humanized heavy chain variable region amino acid sequences with the heavy chain variable region amino acid sequence of the 1A8 antibody. The CDRs (according to Kabat) are underlined.

FIG. 2 is an alignment of three humanized light chain variable region amino acid sequences with the light chain variable region amino acid sequence of the 1A8 antibody. The CDRs (according to Kabat) are underlined.

DETAILED DESCRIPTION

Figure 3:
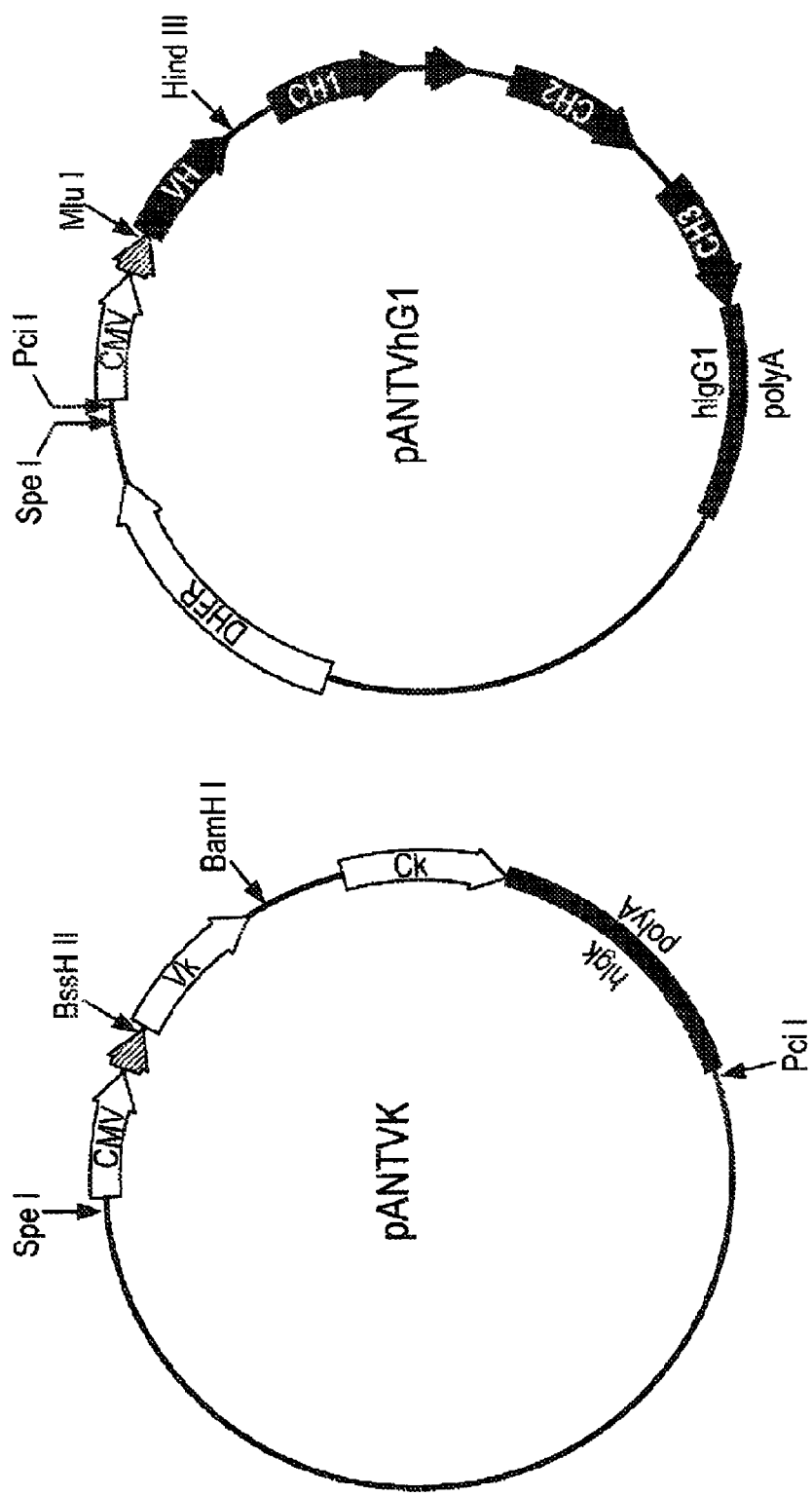
FIG. 3 is a schematic representation of plasmid maps for light chain expression vector pANTVκ and heavy chain expression vector pANTVhG1. Both VH and Vκ vectors contain genomic DNA fragments incorporating introns and poly A sequences. Expression of both chains is driven by a CMV promoter and selection (on the heavy chain vector) is via a DHFR mini gene.

This disclosure features antibodies and antigen-binding fragments that specifically bind the αvβ6 integrin. The β$_6$ subunit of the αvβ6 integrin binds to the latency associated peptide (LAP), the N-terminal 278 amino acids of the latent precursor form of TGF-β, through interaction with an RGD motif. The antibodies and antigen-binding fragments thereof described herein block the interaction between the β$_6$ subunit and the latency associated peptide (LAP). Thus, these antibodies and antigen-binding fragments are useful in inhibiting the activation of the cytokine TGF-β (and inhibiting interactions of β$_6$ with its other ligands) and are useful in treatment of αvβ6-associated disorders such as fibrosis, disorders associated with epithelial injury, acute lung injury, acute kidney injury, and cancers. In addition, the antibody or the antigen-binding fragment thereof can be used to treat or prevent a viral or pathogenic infection wherein the viral or pathogenic infection proceeds, at least in part, due to an interaction between a viral RGD-containing protein and αvβ6.

β6

The amino acid sequence of the human β$_6$ protein (Genbank Accession No. A26609.1) is shown below:

(SEQ ID NO: 29)
MGIELLCLFFLFLGRNDSRTRWLCLGGAETCEDCLLIGPQCAWCAQENF

THPSGVGERCDTPANLLAKGCQLNFIENPVSQVEILKNKPLSVGRQKNS

SDIVQIAPQSLILKLRPGGAQTLQVHVRQTEDYPVDLYYLMDLSASMDD

DLNTIKELGSGLSKEMSKLTSNFRLGFGSFVEKPVSPFVKTTPEEIANP

CSSIPYFCLPTFGFKHILPLTNDAERFNEIVKNQKISANIDTPEGGFDA

IMQAAVCKEKIGWRNDSLHLLVFVSDADSHFGMDSKLAGIVIPNDGLCH

LDSKNEYSMSTVLEYPTIGQLIDKLVQNNVLLIFAVTQEQVHLYENYAK

LIPGATVGLLQKDSGNILQLIISAYEELRSEVELEVLGDTEGLNLSFTA

ICNNGTLFQHQKKCSHMKVGDTASFSVTVNIPHCERRSRHIIIKPVGLG

DALELLVSPECNCDCQKEVEVNSSKCHHGNGSFQCGVCACHPGHMGPRC

ECGEDMLSTDSCKEAPDHPSCSGRGDCYCGQCICHLSPYGNIYGPYCQC

DNFSCVRHKGLLCGGNGDCDCGECVCRSGWTGEYCNCTTSTDSCVSEDG

VLCSGRGDCVCGKCVCTNPGASGPTCERCPTCGDPCNSKRSCIECHLSA

AGQAGEECVDKCKLAGATISEEEDFSKDGSVSCSLQGENECLITFLITT

DNEGKTIIHSINEKDCPKPPNIPMIMLGVSLATLLIGVVLLCIWKLLVS

FHDRKEVAKFEAERSKAKWQTGTNPLYRGSTSTFKNVTYKHREKQKVDL

STDC

The amino acid sequence of the murine β$_6$ protein (Genbank® Accession No. NP_001153036.1) is shown below:

(SEQ ID NO: 31)
MGIELVCLFLLLLGRNDHVQGGCAWGGAESCSDCLLTGPHCAWCSQENFT

HLSGAGERCDTPANLLAKGCQLPFIENPVSRIEVLQNKPLSVGRQKNSSD

IVQIAPQSLVLKLRPGREQTLQVQVRQTEDYPVDLYYLMDLSASMDDDLN

TIKELGSRLAKEMSKLTSNFRLGFGSFVEKPVSPFMKTTPEEITNPCSSI

PYFCLPTFGFKHILPLTDDAERFNEIVRKQKISANIDTPEGGFDAIMQAA

VCKEKIGWRNDSLHLLVFVSDADSHFGMDSKLAGIVIPNDGLCHLDHRNE

YSMSTVLEYPTIGQLIDKLVQNNVLLIFAVTQEQVHLYENYAKLIPGATV

GLLQKDSGNILQLIISAYEELRSEVELEVLGDTEGLNLSFTALCNNGVLF

PHQKKCSHMKVGDTASFNVTVSVSNCEKRSRNLIIKPVGLGDTLEILVSA

ECDCDCQREIETNSSKCHNGNGSFQCGVCTCNPGHMGPHCECGEDMVSTD

SCKESPGHPSCSGRGDCYCGQCICHLSPYGSIYGPYCQCDNFSCLRHKGL

LCGDNGDCDCGECVCRDGWTGEYCNCTTNRDSCTSEDGVLCSGRGDCVCG

KCVCRNPGASGPTCERCPTCGDPCNSKRSCIECYLSADGQAQEECADKCK

AIGATISEEDFSKDTSVSCSLQGENECLITFLITTDNEGKTIIHNINEKD

CPKPPNIPMIMLGVSLAILLIGVVLLCIWKLLVSFHDRKEVAKFEAERSK

AKWQTGTNPLYRGSTSTFKNVTYKHREKHKAGLSSDG

The human and murine β6 proteins share about 91% sequence identity.

Anti-αvβ6 Antibodies

This disclosure includes antibodies and antigen-binding fragments that specifically bind to αvβ6. The antibodies disclosed herein are derived from the murine 1A8 antibody produced by the hybridoma deposited at the ATCC on Aug. 16, 2001, with the accession number PTA-3647. Example 1 discloses six exemplary heavy chain variable regions, VH1, VH2, VH3, VH4, VH5, and VH6 having the amino acid sequences set forth in SEQ ID NOs: 1, 3, 5, 7, 50, and 52, respectively, and three exemplary light chain variable region, VL1, VL2, and VL3, having the amino acid sequences set forth in SEQ ID NOs: 9, 11, and 13, respectively. Each of the VH chains can pair with any of the VL chains: i.e., VH1 can pair with VL1, VL2, or VL3; VH2 can pair with VL1, VL2, or VL3; VH3 can pair with VL1, VL2, or VL3; VH5 can pair with VL1, VL2, or VL3; and VH6 can pair with VL1, VL2, or VL3. Thus, the heavy chain variable region and light chain variable regions disclosed in Example 1 can form 18 different VH-VL pairs.

The amino acid sequences of the complementarity determining regions (CDRs) 1, 2, and 3 as well as the framework regions (FRs) 1, 2, 3, 4 of the six heavy chain variable regions and the three light chain variable regions of the exemplary antibodies described in Example 1 are provided below. The CDRs are based upon the Kabat numbering system.

| Domain | SEQ ID NO | Sequence |
|---|---|---|
| VH CDR1 | 15 | DYTMH |
| VH CDR2 | 16 | VIDTYYGKTNYNQKFEG |
| VH CDR3 | 17 | GGFRRGDRPSLRYAMDS |
| VL CDR1 | 18 | RASQSVSISTYSYIH |
| VL CDR2 | 19 | YASNLES |
| VL CDR3 | 20 | QHSWEIPYT |
| VH1 FR1 | 21 | QVQFVQSGPELKKPGASVKVSCKGSSYTFT |
| VH1 FR2 | 22 | WVKLAHAKTLEWIG |
| VH1 FR3 | 23 | RATMTVDKSSSTAYMELARLRSEDSAVYYCAR |
| VH1 FR4 | 24 | WGQGTSVTVSS |
| VH2 FR1 | 25 | QVQLVQSGAEVKKPGASVKVSCKGSSYTFT |
| VH2 FR2 | 26 | WVKLASAKTLEWIG |
| VH2 FR3 | 27 | RATMTVDKSSSTAYMELSSLRSEDTAVYYCAR |
| VH2 FR4 | 28 | WGQGTLVTVSS |
| VH3 FR1 | 25 | QVQLVQSGAEVKKPGASVKVSCKGSSYTFT |
| VH3 FR2 | 30 | WVRLASAKTLEWIG |
| VH3 FR3 | 27 | RATMTVDKSSSTAYMELSSLRSEDTAVYYCAR |
| VH3 FR4 | 28 | WGQGTLVTVSS |
| VH4 FR1 | 25 | QVQLVQSGAEVKKPGASVKVSCKGSSYTFT |
| VH4 FR2 | 30 | WVRLASAKTLEWIG |
| VH4 FR3 | 35 | RATITVDKSSSTAYMELSSLRSEDTAVYYCAR |
| VH4 FR4 | 28 | WGQGTLVTVSS |
| VH5 FR1 | 54 | QVQFVQSGPELKKPGASVKLSCKGSSYTFT |
| VH5 FR2 | 22 | WVKLAHAKTLEWIG |
| VH5 FR3 | 55 | RATMTVDKSSSTAYMELARLTSEDSAVYYCAR |
| VH5 FR4 | 24 | WGQGTSVTVSS |
| VH6 FR1 | 54 | QVQFVQSGPELKKPGASVKLSCKGSSYTFT |
| VH6 FR2 | 22 | WVKLAHAKTLEWIG |
| VH6 FR3 | 56 | KATMTVDKSSSTAYMDLARLTSEDSAVYYCAR |
| VH6 FR4 | 24 | WGQGTSVTVSS |
| VL1 FR1 | 37 | DIVLTQSPDSLAVSLGERATINC |
| VL1 FR2 | 38 | WFQQKPGQPPKLLIK |
| VL1 FR3 | 39 | GVPDRFSGSGSGTDFTLNIHPVEEEDVGIYYC |
| VL1 FR4 | 40 | FGGGTKVEIK |
| VL2 FR1 | 37 | DIVLTQSPDSLAVSLGERATINC |
| VL2 FR2 | 38 | WFQQKPGQPPKLLIK |
| VL2 FR3 | 43 | GVPDRFSGSGSGTDFTLKISRVEEEDVGIYYC |
| VL2 FR4 | 40 | FGGGTKVEIK |
| VL3 FR1 | 45 | DIVMTQSPDSLAVSLGERATINC |
| VL3 FR2 | 38 | WFQQKPGQPPKLLIK |
| VL3 FR3 | 47 | GVPDRFSGSGSGTDFTLKISRVEAEDVGIYYC |
| VL3 FR4 | 40 | FGGGTKVEIK |

The anti-αvβ6 antibodies of this disclosure can also comprise "alternate CDRs." By "alternate" CDRs are meant CDRs (CDR1, CDR2, and CDR3) defined according to any one of the Chothia, from AbYsis, enhanced Chothia/AbM CDR, or the contact definitions. These alternate CDRs can be obtained, e.g., by using the AbYsis database (www.bioinf.org.uk/abysis/sequence_input/key_annotation/key_annotation.cgi). The amino acid sequences of "alternate" CDRs 1, 2, and 3 of the heavy chain variable region and the light chain variable region of the anti-αvβ6 antibodies of this disclosure are compared with the CDRs defined according to Kabat in the Table below.

| Domain | Kabat | Chothia from AbYsis | Enhanced Chothia/AbM | Contact |
|---|---|---|---|---|
| VH CDR1 | DYTMH (SEQ ID NO: 15) | SYTFTDY (SEQ ID NO: 57) | SYTFTDYTMH (SEQ ID NO: 59) | TDYTMH (SEQ ID NO: 61) |
| VH CDR2 | VIDTYYGKTNYNQKFEG (SEQ ID NO: 16) | DTYYGK (SEQ ID NO: 58) | VIDTYYGKTN (SEQ ID NO: 60) | WIGVIDTYYGKTN (SEQ ID NO: 62) |

-continued

| Domain | Kabat | Chothia from AbYsis | Enhanced Chothia/ AbM | Contact |
|---|---|---|---|---|
| VH CDR3 | GGFRRGDRPSLRYAMDS (SEQ ID NO: 17) | GGFRRGDRPSLRYAMDS (SEQ ID NO: 17) | GGFRRGDRPSLRYAMDS (SEQ ID NO: 17) | ARGGFRRGDRPSLRYAMDS (SEQ ID NO: 63) |
| VL CDR1 | RASQSVSISTYSYIH (SEQ ID NO: 18) | RASQSVSISTYSYIH (SEQ ID NO: 18) | RASQSVSISTYSYIH (SEQ ID NO: 18) | SISTYSYIHWF (SEQ ID NO: 64) |
| VL CDR2 | YASNLES (SEQ ID NO: 19) | YASNLES (SEQ ID NO: 19) | YASNLES (SEQ ID NO: 19) | LLIKYASNLE (SEQ ID NO: 65) |
| VL CDR3 | QHSWEIPYT (SEQ ID NO: 20) | QHSWEIPYT (SEQ ID NO: 20) | QHSWEIPYT (SEQ ID NO: 20) | QHSWEIPY (SEQ ID NO: 66) |

The anti-αvβ6 antibodies of this disclosure can comprise or consist of the heavy chain and light chain CDR 1, CDR2, and CDR3 according to any of the Kabat definition, the Chothia from Abysis definition, the enhanced Chothia/AbM CDR definition, or the contact definitions. The anti-αvβ6 antibodies of this disclosure can comprise or consist of the heavy chain CDR 1, CDR2, and CDR3 and/or light chain CDR 1, CDR2, and CDR3 according to any of the Kabat definition, the Chothia from Abysis definition, the enhanced Chothia/AbM CDR definition, or the contact definitions with 1, 2 or 3 substitutions within one or more of the CDRs (i.e., 1, 2, 3, 4, 5 or 6).

This disclosure also includes antibodies that specifically bind αvβ6 that have heavy chain variable regions that are: 93%, 94%, 95%, 96%, 97%, 98%, or 99% identical to the amino acid sequences set forth in SEQ ID NO: 1; 87%, 88%, 89%, 90%, 91%, 92%, 93%, 94%, 95%, 96%, 97%, 98%, or 99% identical to the amino acid sequences set forth in SEQ ID NO: 3; 86%, 87%, 88%, 89%, 90%, 91%, 92%, 93%, 94%, 95%, 96%, 97%, 98%, or 99% identical to the amino acid sequences set forth in SEQ ID NO: 5; 85%, 86%, 87%, 88%, 89%, 90%, 91%, 92%, 93%, 94%, 95%, 96%, 97%, 98%, or 99% identical to the amino acid sequences set forth in SEQ ID NO: 7; 95%, 96%, 97%, 98%, or 99% identical to SEQ ID NO: 50; or 96.5%, 97%, 98%, or 99% identical to SEQ ID NO: 52. In certain embodiments, these antibodies or antigen binding fragments inhibit αvβ6 binding to LAP of TGF-β, inhibit αvβ6 binding to RGD-motif containing ligands of αvβ6, inhibit TGF-β signaling, and/or inhibit TGF-β activation. In some embodiments, these antibodies further include a light chain variable region that is: 95%, 96%, 97%, 98%, or 99% identical to the amino acid sequences set forth in SEQ ID NO:9; 92%, 93%, 94%, 95%, 96%, 97%, 98%, or 99% identical to the amino acid sequences set forth in SEQ ID NO:11; or 91%, 92%, 93%, 94%, 95%, 96%, 97%, 98%, or 99% identical to the amino acid sequences set forth in SEQ ID NO:13. In certain embodiments, these antibodies or antigen binding fragments inhibit αvβ6 binding to LAP of TGF-β, inhibit αvβ6 binding to RGD-motif containing ligands of αvβ6, inhibit TGF-β signaling, and/or inhibit TGF-β activation.

This disclosure also includes antibodies that specifically bind αvβ6 that have four or fewer (e.g., four, three or fewer, three, two or fewer, two, or one) amino acid substitutions in one, two, three, or all four of the framework regions, and/or four or fewer (e.g., four, three or fewer, three, two or fewer, two, or one) amino acid substitutions in one, two, or all three CDRs, of the heavy chain variable region comprising the amino acid sequences set forth in SEQ ID NOs:1, 3, 5, 7, 50, or 52. The application also includes antibodies that have four or fewer (e.g., four, three or fewer, three, two or fewer, two, or one) amino acid substitutions in one, two, three, or all four of the framework regions, and/or four or fewer (e.g., four, three or fewer, three, two or fewer, two, or one) amino acid substitutions in one, two, or all three CDRs, of the light chain variable regions comprising the amino acid sequences set forth in SEQ ID NOs: 9, 11, or 13. In certain embodiments, the humanized antibodies of this disclosure include antibodies that specifically bind αvβ6 that have four or fewer (e.g., four, three or fewer, three, two or fewer, two, or one) amino acid substitutions in one, two, three, or four of the framework regions, and/or four or fewer (e.g., four, three or fewer, three, two or fewer, two, or one) amino acid substitutions in one, two, or three CDRs, of the heavy chain variable region comprising the amino acid sequences set forth in SEQ ID NOs:1, 3, 5, 7, 50, or 52, and four or fewer (e.g., four, three or fewer, three, two or fewer, two, or one) amino acid substitutions in one, two, three, or four of the framework regions, and/or four or fewer (e.g., four, three or fewer, three, two or fewer, two, or one) amino acid substitutions in one, two, or three CDRs, of the light chain variable regions comprising the amino acid sequences set forth in SEQ ID NOs: 9, 11, or 13. In some embodiments, the amino acid substitutions are conservative amino acid substitutions.

In certain embodiments the VH and or VL region can be linked to a constant region (e.g., a wild-type human Fc region or an Fc region that includes one or more alterations). In certain embodiments, the constant region comprises a CH1 domain and a hinge region. In some embodiments, the constant region comprises a CH3 domain. In some embodiments, the antibody has a constant region derived from a human kappa or lambda sequence. In a specific embodiment, the constant region comprises a human subgroup kappa 2 sequence. The constant region can be a human Fc region, e.g., a wild-type Fc region, or an Fc region that includes one or more amino acid substitutions. The constant region can have substitutions that modify the properties of the antibody (e.g., increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237 (based on Kabat numbering). Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) Mol. Immunol. 30:105-08). See also, e.g., U.S. 2005-0037000.

In certain embodiments the antibodies or antigen binding fragments thereof can be linked to a cytotoxic agent. In some embodiments, the cytotoxic agent is selected from the group consisting of a radionuclide, a biotoxin, an enzymatically active toxin, a cytostatic agent, a prodrug, an immunologically active ligand, a cytokines, an alkylating agent, an antimetabolilte, an anti-proliferative agent, a tubulin binding agent, a hormone, and a hormone antagonist. Exemplary cytotoxic agents include $^{90}$Y, $^{131}$I, Monomethyl Auristatin E (MMAE), mertansine (DM1), DM4, diphtheria toxin, *Pseudomonas* exotoxin (PE38), and A chain of ricin. In a specific embodiment, the cytotoxic agent is a maytansinoid. In certain embodiments, the antibody has an isotype selected from the group consisting of IgG1, IgG2, IgG3, and IgG4.

In certain embodiments the antibodies or antigen binding fragments thereof can be conjugated to one or more agents that are useful for treating or preventing the condition the antibody or antigen binding fragment thereof is being used to treat or prevent. These agents can be, e.g., miRNAs, miRNA mimics, siRNAs, anti-miRs, antisense nucleic acids, ribozymes, small molecule compounds, and other chemical moieties. Such antibodies or antigen binding fragments can be used e.g., to deliver the bound agent(s) to a cell or tissue of interest that expresses αvβ6. In certain embodiments, the antibodies or antigen binding fragments thereof can be conjugated to a drug that has systemic toxicity and use the conjugated antibody or antigen-binding fragment to selectively deliver the drug to αvβ6 expressing cells thereby decreasing or preventing the toxicity of the conjugated drug.

Antibodies can be selected for use based on improved potency, higher affinity or avidity for αvβ6, and/or reduced immunogenicity than previously known αvβ6 antibodies. Methods of determining potency, affinity or avidity, and immunogenicity of antibodies are within the skill of the ordinary artisan.

Methods of Obtaining Anti-αvβ6 Antibodies

Antibodies, such as those described above, can be made, for example, by preparing and expressing synthetic genes that encode the recited amino acid sequences. Methods of generating variants (e.g., comprising amino acid substitutions) of any of the anti-αvβ6 antibodies are well known in the art. These methods include, but are not limited to, preparation by site-directed (or oligonucleotide-mediated) mutagenesis, PCR mutagenesis, and cassette mutagenesis of a prepared DNA molecule encoding the antibody or any portion thereof (e.g., a framework region, a CDR, a constant region). Site-directed mutagenesis is well known in the art (see, e.g., Carter et al., Nucleic Acids Res., 13:4431-4443 (1985) and Kunkel et al., Proc. Natl. Acad. Sci. USA, 82:488 (1987)). PCR mutagenesis is also suitable for making amino acid sequence variants of the starting polypeptide. See Higuchi, in PCR Protocols, pp. 177-183 (Academic Press, 1990); and Vallette et al., Nuc. Acids Res. 17:723-733 (1989). Another method for preparing sequence variants, cassette mutagenesis, is based on the technique described by Wells et al., Gene, 34:315-323 (1985).

Affinity Maturation

In one embodiment, an anti-αvβ6 antibody or antigen-binding fragment thereof described herein is modified, e.g., by mutagenesis, to provide a pool of modified antibodies. The modified antibodies are then evaluated to identify one or more antibodies having altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

Calculations of "sequence identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.*, 22:259-306. Removal of any carbohydrate moieties present on the antibodies may be accomplished chemically or enzymatically as described in the art (Hakimuddin et al. (1987) *Arch. Biochem. Biophys.*, 259:52; Edge et al. (1981) *Anal. Biochem.*, 118:131; and Thotakura et al. (1987) *Meth. Enzymol.*, 138:350). See, e.g., U.S. Pat. No. 5,869,046 for a modification that increases in vivo half life by providing a salvage receptor binding epitope.

In one embodiment, an antibody has CDR sequences (e.g., a Chothia or Kabat CDR) that differ from those of SEQ ID NOs: 15, 16, 17, 18, 19, and 20. CDR sequences that differ from those of the humanized 1A8 antibodies described herein include amino acid changes, such as substitutions of 1, 2, 3, or 4 amino acids if a CDR is 5-7 amino acids in length, or substitutions of 1, 2, 3, 4, 5, 6, or 7 of amino acids in the sequence of a CDR if a CDR is 10 amino acids or greater in length. The amino acid that is substituted can have similar charge, hydrophobicity, or stereochemical characteristics. In some embodiments, the amino acid substitution(s) is a conservative substitution. In other embodiments, the amino acid substitution(s) is a non-conservative substitution. Such substitutions are within the ordinary skill of an artisan. The antibody or antibody fragments thereof that contain the substituted CDRs can be screened to identify antibodies having one or more of the features described herein (e.g., specifically binding to β6, inhibiting the binding of αvβ6 to recombinant LAP; inhibition of adhesion of β6-transfected cells to LAP; ability to inhibit activation of TGF-β).

Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al., *J. Immun.*, 147:2657-62 (1991); Morgan et al., *Immunology*, 86:319-24 (1995)), or changing the species from which the constant region is derived.

The anti-αvβ6 antibodies can be in the form of full length antibodies, or in the form of low molecular weight forms (e.g., biologically active antibody fragments or minibodies) of the anti-αvβ6 antibodies, e.g., Fab, Fab', F(ab')$_2$, Fv, Fd, dAb, scFv, and sc(Fv)2. Other anti-αvβ6 antibodies encompassed by this disclosure include single domain antibody (sdAb) containing a single variable chain such as, VH or VL, or a biologically active fragment thereof. See, e.g., Moller et al., *J. Biol. Chem.*, 285(49): 38348-38361 (2010); Harmsen et al., *Appl. Microbiol. Biotechnol.*, 77(1):13-22 (2007); U.S. 2005/0079574 and Davies et al. (1996) *Protein Eng.*, 9(6):531-7. Like a whole antibody, a sdAb is able to bind selectively to a specific antigen. With a molecular weight of only 12-15 kDa, sdAbs are much smaller than common antibodies and even smaller than Fab fragments and single-chain variable fragments.

Provided herein are compositions comprising a mixture of an anti-αvβ6 antibody or antigen-binding fragment thereof and one or more acidic variants thereof, e.g., wherein the amount of acidic variant(s) is less than about 80%, 70%, 60%, 60%, 50%, 40%, 30%, 30%, 20%, 10%, 5% or 1%. Also provided are compositions comprising an anti-αvβ6 antibody or antigen-binding fragment thereof comprising at least one deamidation site, wherein the pH of the composition is from about 5.0 to about 6.5, such that, e.g., at least about 90% of the anti-αvβ6 antibodies are not deamidated (i.e., less than about 10% of the antibodies are deamidated). In certain embodiments, less than about 5%, 3%, 2% or 1% of the antibodies are deamidated. The pH may be from 5.0 to 6.0, such as 5.5 or 6.0. In certain embodiments, the pH of the composition is 5.5, 5.6, 5.7, 5.8, 5.9, 6.0, 6.1, 6.2, 6.3, 6.4 or 6.5.

An "acidic variant" is a variant of a polypeptide of interest which is more acidic (e.g. as determined by cation exchange chromatography) than the polypeptide of interest. An example of an acidic variant is a deamidated variant.

A "deamidated" variant of a polypeptide molecule is a polypeptide wherein one or more asparagine residue(s) of the original polypeptide have been converted to aspartate, i.e. the neutral amide side chain has been converted to a residue with an overall acidic character. The term "mixture" as used herein in reference to a composition comprising an anti-αvβ6 antibody or antigen-binding fragment thereof, means the presence of both the desired anti-αvβ6 antibody or antigen-binding fragment thereof and one or more acidic variants thereof. The acidic variants may comprise predominantly deamidated anti-αvβ6 antibody, with minor amounts of other acidic variant(s).

In certain embodiments, the binding affinity ($K_D$), on-rate ($K_D$ on) and/or off-rate ($K_D$ off) of the antibody that was mutated to eliminate deamidation is similar to that of the wild-type antibody, e.g., having a difference of less than about 5 fold, 2 fold, 1 fold (100%), 50%, 30%, 20%, 10%, 5%, 3%, 2% or 1%.

In certain embodiments, an anti-αvβ6 antibody or antigen-binding fragment thereof or low molecular weight antibodies thereof specifically binds to αvβ6, inhibits the binding of αvβ6 to recombinant LAP, inhibits adhesion of β6-transfected cells to LAP, have the ability in bioassays to inhibit activation of TGF-β; and/or reduces the severity of symptoms when administered to human patients having one or more of, or animal models of: fibrosis (e.g., lung fibrosis, kidney fibrosis, liver fibrosis), acute lung injury, acute kidney injury, pancreatic cancer, lung cancer, breast cancer, colorectal cancer, head and neck cancer, esophageal cancer, skin cancer, prostate cancer, cervical cancer, ovarian cancer, kidney cancer, and endometrial cancer. In one embodiment, the anti-αvβ6 antibody or antigen-binding fragment thereof or low molecular weight antibodies thereof inhibit disease development in an idiopathic pulmonary fibrosis model (Degryse et al., *Am J Med Sci.* 341(6):444-9 (2011)). These features of an anti-αvβ6 antibody or antigen-binding fragment thereof or low molecular weight antibodies thereof can be measured according to methods known in the art.

Antibody Fragments

Antibody fragments (e.g., Fab, Fab', F(ab')2, Facb, and Fv) of αvβ6-binding antibodies may be prepared by proteolytic digestion of intact αvβ6 antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., *J. Immunol.*, 152:2968-2976 (1994); Better, M. and Horwitz, A. H., *Methods in Enzymology*, 178:476-496 (1989); Pluckthun, A. and Skerra, A., *Methods in Enzymology*, 178:476-496 (1989); Lamoyi, E., *Methods in Enzymology*, 121:652-663 (1989); Rousseaux, J. et al., *Methods in Enzymology*, (1989) 121:663-669 (1989); and Bird, R. E. et al., *TIBTECH*, 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab)2 fragments (Carter et al., *Bio/Technology*, 10:163-167 (1992)). According to another approach, F(ab')2 fragments can be isolated directly from recombinant host cell culture. Fab and F(ab') 2 fragment with increased in vivo half-life comprising a salvage receptor binding epitope residues are described in U.S. Pat. No. 5,869,046.

Minibodies

Minibodies of anti-αvβ6 antibodies include diabodies, single chain (scFv), and single-chain (Fv)2 (sc(Fv)2).

A "diabody" is a bivalent minibody constructed by gene fusion (see, e.g., Holliger, P. et al., *Proc. Natl. Acad. Sci. U.S.A*, 90:6444-6448 (1993); EP 404,097; WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.

An scFv is a single-chain polypeptide antibody obtained by linking the VH and VL with a linker (see e.g., Huston et al., *Proc. Natl. Acad. Sci. U.S.A*, 85:5879-5883 (1988); and Pluckthun, "The Pharmacology of Monoclonal Antibodies" Vol. 113, Ed Resenburg and Moore, Springer Verlag, New York, pp. 269-315, (1994)). The order of VHs and VLs to be linked is not particularly limited, and they may be arranged in any order. Examples of arrangements include: [VH] linker [VL]; or [VL] linker [VH]. The H chain V region and L chain V region in an scFv may be derived from any anti-αvβ6 antibody or antigen-binding fragment thereof described herein.

An sc(Fv)2 is a minibody in which two VHs and two VLs are linked by a linker to form a single chain (Hudson, et al., *J. Immunol. Methods*, (1999) 231: 177-189 (1999)). An sc(Fv)2 can be prepared, for example, by connecting scFvs with a linker. The sc(Fv)2 of the present invention include antibodies preferably in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order. Examples of arrangements are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

Normally, three linkers are required when four antibody variable regions are linked; the linkers used may be identical or different. There is no particular limitation on the linkers that link the VH and VL regions of the minibodies. In some embodiments, the linker is a peptide linker. Any arbitrary single-chain peptide comprising about three to 25 residues (e.g., 5, 6, 7, 8, 9, 10, 11, 12, 13, 14, 15, 16, 17, 18) can be used as a linker. Examples of such peptide linkers include: Ser; Gly Ser; Gly Gly Ser; Ser Gly Gly; Gly Gly Gly Ser (SEQ ID NO:32); Ser Gly Gly Gly (SEQ ID NO:33); Gly Gly Gly Gly Ser (SEQ ID NO:34); Ser Gly Gly Gly Gly (SEQ ID NO:36); Gly Gly Gly Gly Gly Ser (SEQ ID NO:41); Ser Gly Gly Gly Gly Gly (SEQ ID NO:42); Gly Gly Gly Gly Gly Ser (SEQ ID NO:44); Ser Gly Gly Gly Gly Gly Gly (SEQ ID NO:46); (Gly Gly Gly Gly Ser (SEQ ID NO:34)$_n$, wherein n is an integer of one or more; and (Ser Gly Gly Gly Gly (SEQ ID NO:36)$_n$, wherein n is an integer of one or more.

In certain embodiments, the linker is a synthetic compound linker (chemical cross-linking agent). Examples of cross-linking agents that are available on the market include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

The amino acid sequence of the VH or VL in the minibodies may include modifications such as substitutions, deletions, additions, and/or insertions. For example, the modification may be in one or more of the CDRs of the anti-αvβ6 antibody or antigen-binding fragment thereof. In certain embodiments, the modification involves one, two, or three amino acid substitutions in one or more CDRs and/or framework regions of the VH and/or VL domain of the anti-αvβ6 minibody. Such substitutions are made to improve the binding, functional activity and/or reduce immunogenicity of the anti-αvβ6 minibody. In certain embodiments, the substitutions are conservative amino acid substitutions. In other embodiments, one, two, or three amino acids of the CDRs of the anti-αvβ6 antibody or antigen-binding fragment thereof may be deleted or added as long as there is αvβ6 binding and/or functional activity when VH and VL are associated.

Bispecific Antibodies

Bispecific antibodies are antibodies that have binding specificities for at least two different epitopes. Exemplary bispecific antibodies may bind to two different epitopes of the αvβ6 protein. Other such antibodies may combine a αvβ6 binding site with a binding site for another protein (e.g., αvβ1, αvβ3, αvβ5, αvβ8, tumor specific antigens (e.g., alphafetoprotein (AFP), carcinoembryonic antigen (CEA), CA-125, MUC-1, Epithelial tumor antigen (ETA), tyrosinase, Melanoma-associated antigen (MAGE)-1, MAGE-3, BAGE-1, GAGE-1, GnTV, KM-HN-1, KK-LC-1, LAGE-1, NA88-A, NY-ESO-1, SAGE, Sp17, SSX-2, TAG-1, TRAG-3, TRP2, XAGE-1b, HPV 16, HPV E6, HPV E7, TAG-72, L6-antigen, CD19, CD22, CD37, CD52, EGF receptor, HER 2 receptor, Lewis Y), T-cell antigens (e.g., CD2, CD3, CD5, CD6, CD7, TCR)). Bispecific antibodies can be prepared as full length antibodies or low molecular weight forms thereof (e.g., F(ab')$_2$ bispecific antibodies, sc(Fv)2 bispecific antibodies, diabody bispecific antibodies).

Traditional production of full length bispecific antibodies is based on the co-expression of two immunoglobulin heavy chain-light chain pairs, where the two chains have different specificities (Millstein et al., Nature, 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

Multivalent Antibodies

A multivalent antibody may be internalized (and/or catabolized) faster than a bivalent antibody by a cell expressing an antigen to which the antibodies bind. The antibodies describe herein can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. An exemplary dimerization domain comprises (or consists of) an Fc region or a hinge region. A multivalent antibody can comprise (or consist of) three to about eight (e.g., four) antigen binding sites. The multivalent antibody optionally comprises at least one polypeptide chain (e.g., at least two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is a polypeptide chain of an Fc region, X1 and X2 represent an amino acid or peptide spacer, and n is 0 or 1.

Conjugated Antibodies

The antibodies disclosed herein may be conjugated antibodies which are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, fluorescent substances, luminescent substances, haptens, enzymes, metal chelates, and drugs.

In one embodiment, to improve the cytotoxic actions of anti-$\alpha v \beta 6$ antibodies (and antigen-binding fragments thereof) and consequently their therapeutic effectiveness, the antibodies are conjugated with highly toxic substances, including radioisotopes and cytotoxic agents. These conjugates can deliver a toxic load selectively to the target site (i.e., cells expressing the antigen recognized by the antibody) while cells that are not recognized by the antibody are spared. In order to minimize toxicity, conjugates are generally engineered based on molecules with a short serum half-life (e.g., use of antibody fragments, murine sequences, and/or IgG3 or IgG4 isotypes). Exemplary radioisotopes include: $^{90}$Y, $^{125}$I, $^{131}$I, $^{123}$I, $^{111}$I, $^{105}$Rh, $^{153}$Sm, $^{67}$Cu, $^{67}$Ga, $^{166}$Ho, $^{177}$Lu, $^{186}$Re, and $^{188}$Re. Cytotoxic agents that can be used include cytotoxic drugs which are used for cancer therapy. As used herein, "a cytotoxic agent" means any agent that is detrimental to the growth and proliferation of cells and may act to reduce, inhibit, or destroy a cell or malignancy. Exemplary cytotoxic agents include, but are not limited to, radionuclides, biotoxins, enzymatically active toxins, cytostatic or cytotoxic therapeutic agents (e.g., alkylating agents, antimetabolites, anti-proliferative agents, tubulin binding agents, hormones and hormone antagonists), prodrugs, immunologically active ligands and biological response modifiers such as cytokines. Any cytotoxin that acts to retard or slow the growth of immunoreactive cells or malignant cells is within the scope of the present invention. Exemplary cytostatics include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. In one embodiment, the cytotoxic agent that is conjugated to an antibody or antigen-binding fragment described herein is a maytansinoid. Maytansinoids are known in the art to include maytansine, maytansinol, C-3 esters of maytansinol, and other maytansinol analogues and derivatives (see, e.g., U.S. Pat. Nos. 5,208,020 and 6,441,163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., J. Med. Chem., 21, 31-37 (1978). Methods for generating maytansinol and analogues and derivatives thereof are described in, for example, U.S.

Pat. No. 4,151,042. In certain embodiments, the maytansinoids comprise a linking moiety that contains a reactive chemical group (e.g., C-3 esters of maytansinol and its analogs where the linking moiety contains a disulfide bond and the attachment moiety comprises a N-succinimidyl or N-sulfosuccinimidyl ester). In certain embodiments, the maytansinoid conjugated with the antibodies or antigen-binding described herein is $N^{2'}$-deacetyl-$N^{2'}$-(-3-mercapto-1-oxopropyl)-maytansine (DM1) or $N^{2'}$-deacetyl-$N^{2'}$-(4-mercapto-4-methyl-1-oxopentyl)-maytansine (DM4). In certain other embodiments, cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of these families include, for example, adriamycin, carminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. In other embodiments, the cytotoxic agents include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e g aminogluthetimide can also be conjugated with the antibodies or antigen-binding fragments thereof described herein. In certain embodiments, the cytotoxic agent comprises a member or derivative of the enediyne family of anti-tumor antibiotics, including calicheamicin, esperamicins, or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins, and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs. In further embodiments, the antibodies or antigen-binding fragments thereof can also be associated with a biotoxin such as ricin subunit A, abrin, diptheria toxin, botulinum, cyanginosins, saxitoxin, shigatoxin, tetanus, tetrodotoxin, trichothecene, verrucologen, or a toxic enzyme. Such biotoxins can be made using genetic engineering techniques that allow for direct expression of the antibody-toxin construct. One skilled in the art could readily form such constructs using conventional techniques. Methods of conjugating cytotoxic agents are well known in the art (see, e.g., U.S. Pat. No. 8,021,661).

In certain embodiments, an anti-αvβ6 antibody or antigen-binding fragment thereof are modified with a moiety that improves its stabilization and/or retention in circulation, e.g., in blood, serum, or other tissues, e.g., by at least 1.5, 2, 5, 10, or 50 fold. For example, the anti-αvβ6 antibody or antigen-binding fragment thereof can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the anti-αvβ6 antibody or antigen-binding fragment thereof can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) (see, e.g., Chapman et al., Nature Biotechnology, 17: 780-783 (1999), or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides. The efficacy of a therapeutic antibody can be improved by increasing its serum persistence, thereby allowing higher circulating levels, less frequent administration, and reduced doses. The half-life of an IgG depends on its pH-dependent binding to the neonatal receptor FcRn. FcRn, which is expressed on the surface of endothelial cells, binds the IgG in a pH-dependent manner and protects it from degradation. Some antibodies that selectively bind the FcRn at pH 6.0, but not pH 7.4, exhibit a higher half-life in a variety of animal models. In certain embodiments, the antibodies of the present disclosure have one or more mutations at the interface between the CH2 and CH3 domains, such as T250Q/M428L and M252Y/S254T/T256E+H433K/N434F (the numbering is according to the EU index), which increase the binding affinity to FcRn and the half-life of IgG1 in vivo. In other embodiments, the antibodies herein have a modified Fc region comprising at least one modification relative to a wild-type human Fc region, where the modification is selected from the group consisting of 434S, 252Y/428L, 252Y/434S, and 428L/434S, and the numbering is according to the EU index.

The antibodies or antigen-binding fragments thereof can also be conjugated to siRNAs, miRNAs, or anti-miRs to deliver the siRNA, miRNA, or anti-miR to cells expressing αvβ6 (see, e.g., Song et al., *Nat. Biotechnol.,* 23(6):709-17 (2005); Schneider et al., *Molecular Therapy Nucleic Acids,* 1:e46 (2012)). The siRNAs, miRNAs, or anti-miRs can target TGF-β or components of the TGF-β signaling pathway. In some embodiments, the siRNAs, miRNAs, or anti-miRs can target genes involved in the disease being treated (e.g., fibrosis, acute lung injury, acute kidney injury, cancer). For example, to treat fibrotic diseases, one or more of the following can be targeted to αvβ6-expressing cells using αvβ6 antibodies or antigen-binding fragments thereof conjugated to: anti-miRs to microRNAs such as: miR-142-3p, miR-155, miR-192, miR-199a/b, miR-208, miR-21, miR-215, miR-216, miR-217, miR-23a, miR-27a, miR-27b, miR-32, miR-338, miR-34a, miR-377, miR-382; or conjugated to microRNAs such as: let-7d, miR-107, miR-132, miR-133, miR-141, miR-15b, miR-16, miR-150, miR-18a, miR-19a/b, miR-194, miR-200a/b, miR-204, miR-211, miR-26a/b, miR-29a/b/c, miR-30c, miR-335, miR-449a/b, and miR-590. In a specific embodiment, anti-miR-21 conjugated to αvβ6 antibodies or antigen-binding fragments thereof can be used to treat kidney fibrosis or cancer (e.g., hepatocellular carcinoma); and αvβ6 antibodies or antigen-binding fragments thereof conjugated to anti-miR-10b can be used to treat cancers such as glioblastoma.

The antibodies or antigen-binding fragments thereof can also be conjugated to small molecules and other chemical moieties.

The above-described conjugated antibodies can be prepared by performing chemical modifications on the antibodies or the lower molecular weight forms thereof described herein. Methods for modifying antibodies are well known in the art (e.g., U.S. Pat. No. 5,057,313 and U.S. Pat. No. 5,156,840).

Methods of Producing Antibodies

The αvβ6 antibodies (or antibody binding fragments thereof) of this disclosure may be produced in bacterial or eukaryotic cells. Some antibodies, e.g., Fab's, can be produced in bacterial cells, e.g., *E. coli* cells. Antibodies can also be produced in eukaryotic cells such as transformed cell lines (e.g., CHO, 293E, COS). In addition, antibodies (e.g., scFv's) can be expressed in a yeast cell such as *Pichia* (see, e.g., Powers et al., *J Immunol Methods*. 251:123-35 (2001)), *Hanseula*, or *Saccharomyces*. To produce the antibody of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., *Science*, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.*, 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, 293, 293T, and NIH3T3 cells, the expression vector includes a promoter necessary for expression in these cells, for example, an SV40 promoter (Mulligan et al., *Nature*, 277:108 (1979)), MMLV-LTR promoter, EF1α promoter (Mizushima et al., *Nucleic Acids Res.*, 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of an anti-αvβ6 antibody is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. Animals are also provided comprising one or more of the nucleic acids described herein.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Characterization of the Antibodies

The αvβ6-binding properties of the antibodies described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

The binding interaction of a protein of interest (an anti-αvβ$_6$ antibody) and a target (e.g., αvβ6) can be analyzed using the OCTET® systems. In this method, one of several variations of instruments (e.g., OCTET® QK$^e$ and QK), made by the FortéBio company are used to determine protein interactions, binding specificity, and epitope mapping. The OCTET® systems provide an easy way to monitor real-time binding by measuring the changes in polarized light that travels down a custom tip and then back to a sensor.

The binding interaction of a protein of interest (an anti-αvβ$_6$ antibody) and a target (e.g., αvβ6) can be analyzed using Surface Plasmon Resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $K_{on}$ and $K_{off}$, for the binding of a biomolecule to a target.

Epitopes can also be directly mapped by assessing the ability of different antibodies to compete with each other for binding to human αvβ$_6$ or β$_6$ using BIACORE chromatographic techniques (Pharmacia BIAtechnology Handbook, "Epitope Mapping", Section 6.3.2, (May 1994); see also Johne et al. (1993) *J. Immunol. Methods*, 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in *Antibodies: A Laboratory Manual*, ed. by Harlow and Lane, Cold Spring Harbor press (1988)).

Antibodies with Altered Effector Function

The interaction of antibodies and antibody-antigen complexes with cells of the immune system triggers a variety of responses, referred to herein as effector functions. Immune-mediated effector functions include two major mechanisms: antibody-dependent cell-mediated cytotoxicity (ADCC) and complement-dependent cytotoxicity (CDC). Both of them are mediated by the constant region of the immunoglobulin protein. The antibody Fc domain is, therefore, the portion that defines interactions with immune effector mechanisms.

IgG antibodies activate effector pathways of the immune system by binding to members of the family of cell surface Fcγ receptors and to C1q of the complement system. Ligation of effector proteins by clustered antibodies triggers a variety of responses, including release of inflammatory cytokines, regulation of antigen production, endocytosis, and cell killing. In some clinical applications these responses are crucial for the efficacy of a monoclonal antibody. In others they provoke unwanted side effects such as inflammation and the elimination of antigen-bearing cells. Accordingly, the present invention further relates to αvβ6-binding proteins, including antibodies, with altered, e.g., increased or reduced effector functions.

Effector function of an anti-αvβ6 antibody of the present invention may be determined using one of many known assays. The anti-αvβ6 antibody's effector function may be increased or reduced relative to a second anti-αvβ6 antibody. In some embodiments, the second anti-αvβ6 antibody may be any antibody that binds αvβ6 specifically. In other embodiments, the second αvβ6-specific antibody may be any of the antibodies of the invention, such as the antibodies described in Example 1. In other embodiments, where the anti-αvβ6 antibody of interest has been modified to increase or reduce effector function, the second anti-αvβ6 antibody may be the unmodified or parental version of the antibody.

Effector functions include antibody-dependent cell-mediated cytotoxicity (ADCC), whereby antibodies bind Fc receptors on cytotoxic T cells, natural killer (NK) cells, or macrophages leading to cell death, and complement-dependent cytotoxicity (CDC), which is cell death induced via activation of the complement cascade (reviewed in Daeron, *Annu. Rev. Immunol.*, 15:203-234 (1997); Ward and Ghetie, *Therapeutic Immunol.*, 2:77-94 (1995); and Ravetch and Kinet, *Annu. Rev. Immunol.* 9:457-492 (1991)). Such effector functions generally require the Fc region to be combined with a binding domain (e.g. an antibody variable domain) and can be assessed using standard assays that are known in the art (see, e.g., WO 05/018572, WO 05/003175, and U.S. Pat. No. 6,242,195).

Effector functions can be avoided by using antibody fragments lacking the Fc domain such as Fab, Fab'2, or single chain Fv. An alternative is to use the IgG4 subtype antibody, which binds to FcγRI but which binds poorly to C1q and FcγRII and RIII. The IgG2 subtype also has reduced binding to Fc receptors, but retains significant binding to the H131 allotype of FcγRIIa and to C1q. Thus, additional changes in the Fc sequence are required to eliminate binding to all the Fc receptors and to C1q.

Several antibody effector functions, including ADCC, are mediated by Fc receptors (FcRs), which bind the Fc region of an antibody. The affinity of an antibody for a particular FcR, and hence the effector activity mediated by the antibody, may be modulated by altering the amino acid sequence and/or post-translational modifications of the Fc and/or constant region of the antibody.

FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Both FcγRII and FcγRIII have two types: FcγRIIA (CD32) and FcγRIIB (CD32); and FcγRIIIA (CD16a) and FcγRIIIB (CD16b). Because each FcγR subclass is encoded by two or three genes, and alternative RNA splicing leads to multiple transcripts, a broad diversity in FcγR isoforms exists. For example, FcγRII (CD32) includes the isoforms IIa, IIb1, IIb2 IIb3, and IIc.

The binding site on human and murine antibodies for FcγR has been previously mapped to the so-called "lower hinge region" consisting of residues 233-239 (EU index numbering as in Kabat et al., Sequences of Proteins of Immunological Interest, 5th Ed. Public Health Service, National Institutes of Health, Bethesda, Md. (1991), Woof et al., *Molec. Immunol.* 23:319-330 (1986); Duncan et al., *Nature* 332:563 (1988); Canfield and Morrison, *J. Exp. Med.* 173:1483-1491 (1991); Chappel et al., *Proc. Natl. Acad. Sci USA* 88:9036-9040 (1991)). Of residues 233-239, P238 and 5239 are among those cited as possibly being involved in binding. Other previously cited areas possibly involved in binding to FcγR are: G316-K338 (human IgG) for human FcγRI (Woof et al., *Mol. Immunol.*, 23:319-330 (1986)); K274-R301 (human IgG1) for human FcγRIII (Sarmay et al., *Molec. Immunol.* 21:43-51 (1984)); and Y407-R416 (human IgG) for human FcγRIII (Gergely et al., *Biochem. Soc. Trans.* 12:739-743 (1984) and Shields et al., *J Biol Chem* 276: 6591-6604 (2001), Lazar G A et al., *Proc Natl Acad Sci* 103: 4005-4010 (2006). These and other stretches or regions of amino acid residues involved in FcR binding may be evident to the skilled artisan from an examination of the crystal structures of Ig-FcR complexes (see, e.g., Sondermann et al. 2000 *Nature* 406(6793):267-73 and Sondermann et al. 2002 *Biochem Soc Trans.* 30(4):481-6). Accordingly, the anti-αvβ6 antibodies of the present invention include modifications of one or more of the aforementioned residues (to increase or decrease effector function as needed).

Another approach for altering monoclonal antibody effector function include mutating amino acids on the surface of the monoclonal antibody that are involved in effector binding interactions (Lund, J., et al. (1991) *J. Immunol.* 147(8): 2657-62; Shields, R. L. et al. (2001) *J. Biol. Chem.* 276(9): 6591-604).

Methods of increasing effector function of antibodies are well known in the art (see, e.g., Kelley et al., *Methods Mol. Biol.*, 901:277-93 (2012); Natsume et al., *Drug Des Devel Ther.*, 3:7-16 (2009); U.S. Pat. No. 8,188,231, U.S. Pat. No. 7,960,512). In one embodiment, the αvβ6 antibodies have one, two, three, four, five, six, seven, or more amino acid substitutions at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein the numbering of the residues in the Fc region is that of the EU index as in Kabat. In certain embodiments, the αvβ6 antibodies have one, two, three, four, five, six, seven, or more of the amino acid substitutions selected from the group consisting of: D221K, D221Y, K222E, K222Y, T223E, T223K, H224E, H224Y, T225E, T225K, T225W, P227E, P227G, P227K, P227Y, P228E, P228G, P228K, P228Y, P230A, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234K, L234M, L234N, L234P, L234Q, L234R, L234S, L234T, L234V, L234W, L234Y, L235A, L235D, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239E, S239F, S239G, S239H, S239I, S239K, S239L, S239M, S239N, S239P, S239Q, S239R, S239T, S239V, S239W, S239Y, V240A, V240I, V240M, V240T, F241D, F241E, F241L, F241R, F241S, F241W, F241Y, F243E, F243H, F243L, F243Q, F243R, F243W, F243Y, P244H, P245A, K246D, K246E, K246H, K246Y, P247G, P247V, D249H, D249Q, D249Y, R255E, R255Y, E258H, E258S, E258Y, T260D, T260E, T260H, T260Y, V262A, V262E, V262F, V262I, V262T, V263A, V263I, V263M, V263T, V264A, V264D, V264E, V264F, V264G, V264H, V264I, V264K, V264L, V264M, V264N, V264P, V264Q, V264R, V264S, V264T, V264W, V264Y, D265F, D265G, D265H, D265I, D265K, D265L, D265M, D265N, D265P, D265Q, D265R, D265S, D265T, D265V, D265W, D265Y, V266A, V266I, V266M, V266T, S267D, S267E, S267F, S267H, S267I, S267K, S267L, S267M, S267N, S267P, S267Q, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, D280G, D280K, D280L, D280P, D280W, G281D, G281E, G281K, G281N, G281P, G281Q, G281Y, V282E, V282G, V282K, V282P, V282Y, E283G, E283H, E283K, E283L, E283P, E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296H, Y296I, Y296K, Y296L, Y296M, Y296N, Y296Q, Y296R, Y296S, Y296T, Y296V, N297D, N297E, N297F, N297G, N297H, N297I, N297K, N297L, N297M, N297P, N297Q, N297R, N297S, N297T, N297V, N297W, N297Y, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328E, L328F, L328G, L328H, L328I, L328K, L328M, L328N, L328P, L328Q, L328R, L328S, L328T, L328V, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330M, A330N, A330P, A330R, A330S, A330T, A330V, A330W, A330Y, P331D, P331F, P331H, P331I, P331L, P331M, P331Q, P331R, P331T, P331V, P331W, P331Y, I332A, I332D, I332E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334L, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat. In a particular embodiment, the αvβ6 antibodies comprise one, two, or three of the following mutations: S239D, S239D/I332E, S239D/I332E/A330L, S239D/I332E/G236A, S298A, A330L I332E, E333A, and K334A.

The presence of oligosaccharides-specifically, the N-linked oligosaccharide at asparigine-297 in the CH2 domain of IgG1—is important for binding to FcγR as well as C1q. Reducing the fucose content of antibodies improves effector function (see, e.g., U.S. Pat. No. 8,163,551). In certain embodiments the αvβ6 antibodies have reduced fucosylation and amino acid substitutions that increase effector function (e.g., one, two, or three of the following mutations: S298A; E333A; and K334A). Effector function can also be achieved by preparing and expressing the anti-αvβ6 antibodies described herein in the presence of alpha-mannosidase I inhibitors (e.g., kifunensine) at a concentration of the inhibitor of about 60-200 ng/mL (e.g., 60 ng/mL, 75 ng/mL, 100 ng/mL, 150 ng/ml). Antibodies expressed in the presence of alpha-mannosidase I inhibitors contain mainly oligomannose-type glycans and generally demonstrate increased ADCC activity and affinity for FcγRIIIA, but reduced C1q binding.

Anti-αvβ6 antibodies of the present disclosure with increased effector function include antibodies with increased binding affinity for one or more Fc receptors (FcRs) relative to a parent or non-variant anti-αvβ6 antibody. Accordingly, anti-αvβ6 antibodies with increased FcR binding affinity includes anti-αvβ6 antibodies that exhibit a 1.5-fold, 2-fold, 2.5-fold, 3-fold, 4-fold, or 5-fold or higher increase in binding affinity to one or more Fc receptors compared to a parent or non-variant anti-αvβ6 antibody. In some embodiments, an anti-αvβ6 antibody with increased effector function binds to an FcR with about 10-fold greater affinity relative to a parent or non-variant antibody. In other embodiments, an anti-αvβ36 antibody with increased effector function binds to an FcR with about 15-fold greater affinity or with about 20-fold greater affinity relative to a parent or non-variant antibody. The FcR receptor may be one or more of FcγRI (CD64), FcγRII (CD32), and FcγRIII, and isoforms thereof, and FcεR, FcμR, FcδR, and/or an FcαR. In particular embodiments, an anti-αvβ6 antibody with increased effector function exhibits a 1.5-fold, 2-fold, 2.5-fold, 3-fold, 4-fold, or 5-fold or higher increase in binding affinity to FcγRIIa.

To reduce effector function, one can use combinations of different subtype sequence segments (e.g., IgG2 and IgG4 combinations) to give a greater reduction in binding to Fcγ receptors than either subtype alone (Armour et al., *Eur. J. Immunol.*, 29:2613-1624 (1999); *Mol. Immunol.*, 40:585-593 (2003)). In addition, sites of N-linked glycosylation can be removed as a means of reducing effector function. A large number of Fc variants having altered and/or reduced affinities for some or all Fc receptor subtypes (and thus for effector functions) are known in the art. See, e.g., US 2007/0224188; US 2007/0148171; US 2007/0048300; US 2007/0041966; US 2007/0009523; US 2007/0036799; US 2006/0275283; US 2006/0235208; US 2006/0193856; US 2006/0160996; US 2006/0134105; US 2006/0024298; US 2005/0244403; US 2005/0233382; US 2005/0215768; US 2005/0118174; US 2005/0054832; US 2004/0228856; US 2004/132101; US 2003/158389; see also U.S. Pat. Nos. 7,183,387; 6,737,056; 6,538,124; 6,528,624; 6,194,551; 5,624,821; 5,648,260. In certain embodiments amino acids at positions 232, 234, 235, 236, 237, 239, 264, 265, 267, 269, 270, 299, 325, 328, 329, and 330 (numbered according to Kabat) are substituted to reduce effector function. Non-limiting examples of substitutions that reduce effector function include one or more of: K322A; L234A/L235A; G236T; G236R; G236Q; H268A; H268Q; V309L; A330S; P331S; V234A/G237A/P238S/H268A/V309L/A330S/P331S; E233P/L234V/L235A/G236Q+A327G/A330S/P331S; and L235E+E318A/K320A/K322A.

Anti-αvβ6 antibodies of the present invention with reduced effector function include antibodies with reduced binding affinity for one or more Fc receptors (FcRs) relative to a parent or non-variant anti-αvβ6 antibody. Accordingly, anti-αvβ6 antibodies with reduced FcR binding affinity includes anti-αvβ6 antibodies that exhibit a 1.5-fold, 2-fold, 2.5-fold, 3-fold, 4-fold, or 5-fold or higher decrease in binding affinity to one or more Fc receptors compared to a parent or non-variant anti-αvβ6 antibody. In some embodiments, an anti-αvβ6 antibody with reduced effector function binds to an FcR with about 10-fold less affinity relative to a parent or non-variant antibody. In other embodiments, an anti-αvβ6 antibody with reduced effector function binds to an FcR with about 15-fold less affinity or with about 20-fold less affinity relative to a parent or non-variant antibody. The FcR receptor may be one or more of FcγRI (CD64), FcγRII (CD32), and FcγRIII, and isoforms thereof, and FcεR, FcμR, FcδR, and/or an FcαR. In particular embodiments, an anti-αvβ6 antibody with reduced effector function exhibits a 1.5-fold, 2-fold, 2.5-fold, 3-fold, 4-fold, or 5-fold or higher decrease in binding affinity to FcγRIIa.

In CDC, the antibody-antigen complex binds complement, resulting in the activation of the complement cascade and generation of the membrane attack complex. Activation of the classical complement pathway is initiated by the binding of the first component of the complement system (C1q) to antibodies (of the appropriate subclass) which are bound to their cognate antigen; thus the activation of the complement cascade is regulated in part by the binding affinity of the immunoglobulin to C1q protein. To activate the complement cascade, it is necessary for C1q to bind to at least two molecules of IgG1, IgG2, or IgG3, but only one molecule of IgM, attached to the antigenic target (Ward and Ghetie, *Therapeutic Immunology* 2:77-94 (1995) p. 80). To assess complement activation, a CDC assay, e.g. as described in Gazzano-Santoro et al., *J. Immunol. Methods*, 202:163 (1996), may be performed.

Various residues of the IgG molecule are involved in binding to C1q including the Glu318, Lys320 and Lys322 residues on the CH2 domain, amino acid residue 331 located on a turn in close proximity to the same beta strand, the Lys235 and Gly237 residues located in the lower hinge region, and residues 231 to 238 located in the N-terminal region of the CH2 domain (see e.g., Xu et al., *J. Immunol.* 150:152A (Abstract) (1993), WO94/29351; Tao et al, *J. Exp. Med.*, 178:661-667 (1993); Brekke et al., *Eur. J. Immunol.*, 24:2542-47 (1994); Burton et al; *Nature*, 288:338-344 (1980); Duncan and Winter, *Nature* 332:738-40 (1988); Idusogie et al *J Immunol* 164: 4178-4184 (2000; U.S. Pat. No. 5,648,260, and U.S. Pat. No. 5,624,821).

Anti-αvβ6 antibodies with improved C1q binding can comprise an amino acid substitution at one, two, three, or four of amino acid positions 326, 327, 333 and 334 of the human IgG Fc region, where the numbering of the residues in the IgG Fc region is that of the EU index as in Kabat. In one embodiment, the anti-αvβ6 antibodies include the following amino acid substitutions: K326W/E333S, which are known to increase binding of an IgG1 antibody to C1q (Steurer W. et al., *J Immunol.*, 155(3):1165-74 (1995)).

Anti-αvβ6 antibodies with reduced C1q binding can comprise an amino acid substitution at one, two, three, or four of amino acid positions 270, 322, 329 and 331 of the human IgG Fc region, where the numbering of the residues in the IgG Fc region is that of the EU index as in Kabat. As an example in IgG1, two mutations in the COOH terminal region of the CH2 domain of human IgG1—K322A and P329A—do not activate the CDC pathway and were shown to result in more than a 100 fold decrease in C1q binding (U.S. Pat. No. 6,242,195).

Accordingly, in certain embodiments, an anti-αvβ6 antibody of the present invention exhibits increased or reduced binding to a complement protein relative to a second anti-αvβ6 antibody. In certain embodiments, an anti-αvβ6 antibody of the invention exhibits increased or reduced binding to C1q by a factor of about 1.5-fold or more, about 2-fold or more, about 3-fold or more, about 4-fold or more, about 5-fold or more, about 6-fold or more, about 7-fold or more, about 8-fold or more, about 9-fold or more, about 10-fold or more, or about 15-fold or more, relative to a second anti-αvβ6 antibody.

Thus, in certain embodiments of the invention, one or more of these residues may be modified, substituted, or removed or one or more amino acid residues may be inserted so as to increase or decrease CDC activity of the anti-αvβ6 antibodies provided herein.

In certain other embodiments, the present invention provides an anti-αvβ6 antibody that exhibits reduced binding to one or more FcR receptors but that maintains its ability to bind complement (e.g., to a similar or, in some embodiments, to a lesser extent than a native, non-variant, or parent anti-αvβ₆ antibody). Accordingly, an anti-αvβ6 antibody of the present invention may bind and activate complement while exhibiting reduced binding to an FcR, such as, for example, FcγRIIa (e.g., FcγRIIa expressed on platelets). Such an antibody with reduced or no binding to FcγRIIa (such as FcγRIIa expressed on platelets, for example) but that can bind C1q and activate the complement cascade to at least some degree will reduce the risk of thromboembolic events while maintaining perhaps desirable effector functions. In alternative embodiments, an anti-αvβ6 antibody of the present invention exhibits reduced binding to one or more FcRs but maintains its ability to bind one or more other FcRs. See, for example, US 2007-0009523, 2006-0194290, 2005-0233382, 2004-0228856, and 2004-0191244, which describe various amino acid modifications that generate antibodies with reduced binding to FcRI, FcRII, and/or FcRIII, as well as amino acid substitutions that result in increased binding to one FcR but decreased binding to another FcR.

Accordingly, effector functions involving the constant region of an anti-αvβ6 antibody may be modulated by altering properties of the constant region, and the Fc region in particular. In certain embodiments, the anti-αvβ6 antibody having increased or decreased effector function is compared with a second antibody with effector function and which may be a non-variant, native, or parent antibody comprising a native constant or Fc region that mediates effector function.

A native sequence Fc or constant region comprises an amino acid sequence identical to the amino acid sequence of a Fc or constant chain region found in nature. Preferably, a control molecule used to assess relative effector function comprises the same type/subtype Fc region as does the test or variant antibody. A variant or altered Fc or constant region comprises an amino acid sequence which differs from that of a native sequence heavy chain region by virtue of at least one amino acid modification (such as, for example, post-translational modification, amino acid substitution, insertion, or deletion). Accordingly, the variant constant region may contain one or more amino acid substitutions, deletions, or insertions that results in altered post-translational modifications, including, for example, an altered glycosylation pattern. A parent antibody or Fc region is, for example, a variant having normal effector function used to construct a constant region (i.e., Fc) having altered, e.g., increased effector function.

Antibodies with altered (e.g., increased) effector function(s) may be generated by engineering or producing antibodies with variant constant, Fc, or heavy chain regions. Recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g. glycosylation patterns, may be achieved by manipulating the host cell and cell culture and expression conditions by which the antibody is produced.

Certain embodiments of the present invention relate to an anti-αvβ6 antibody comprising one or more heavy chain CDR sequences selected from VH CDR1 of SEQ ID NO:15, VH CDR2 of SEQ ID NO:16, and VH CDR3 of SEQ ID NO:17, wherein the antibody further comprises a variant Fc region that confers increased or reduced effector function compared to a native or parental Fc region. In further embodiments, the anti-αvβ6 antibody comprises at least two of the CDRs, and in other embodiments the antibody comprises all three of the heavy chain CDR sequences.

Other embodiments of the present invention relate to an anti-αvβ6 antibody comprising one or more light chain CDR sequences selected from VL CDR1 of SEQ ID NO:18, VL CDR2 of SEQ ID NO:19, and VL CDR3 of SEQ ID NO:20 the antibody further comprising a variant Fc region that confers increased or reduced effector function compared to a native or parental Fc region. In further embodiments, the anti-αvβ6 antibody comprises at least two of the light chain CDRs, and in other embodiments the antibody comprises all three of the light chain CDR sequences.

In further embodiments of the present invention, the anti-αvβ6 antibody with increased or reduced effector function comprises all three light chain CDR sequences (CDRs 1, 2, and 3) of SEQ ID NO:9 and comprises all three heavy chain CDR sequences (CDRs 1, 2, and 3) of SEQ ID NO:1. In certain embodiments, the anti-αvβ6 antibody with increased or reduced effector function comprises: three or fewer, two or fewer, or one amino acid substitution in one, two, or three CDRs of SEQ ID NO:9 and three or fewer, two or fewer, or one amino acid substitution in one, two, or three CDRs of SEQ ID NO:1.

In other embodiments, the invention relates to an anti-αvβ6 antibody comprising a VL sequence selected from the group consisting of: SEQ ID NOs:9, 11, and 13, the antibody further comprising a variant Fc region that confers reduced effector function compared to a native or parental Fc region. In yet other embodiments, the invention relates to an anti-αvβ6 antibody comprising a VH sequence selected from the group consisting of SEQ ID NOs: 1, 3, 5, and 7, the antibody further comprising a variant Fc region that confers reduced effector function compared to a native or parental Fc region.

Anti-αvβ6 Antibodies with Altered Glycosylation

Glycan removal produces a structural change that should greatly reduce binding to all members of the Fc receptor family across species. In glycosylated antibodies, including anti-αvβ6 antibodies, the glycans (oligosaccharides) attached to the conserved N-linked site in the CH2 domains of the Fc dimer are enclosed between the CH2 domains, with the sugar residues making contact with specific amino acid residues on the opposing CH2 domain. Different glycosylation patterns are associated with different biological properties of antibodies (Jefferis and Lund, 1997, *Chem. Immunol.*, 65: 111-128; Wright and Morrison, 1997, *Trends Biotechnol.*, 15: 26-32). Certain specific glycoforms confer potentially advantageous biological properties. Loss of the glycans changes spacing between the domains and increases their mobility relative to each other and is expected to have an inhibitory effect on the binding of all members of the Fc receptor family. For example, in vitro studies with various glycosylated antibodies have demonstrated that removal of the CH2 glycans alters the Fc structure such that antibody binding to Fc receptors and the complement protein C1Q are greatly reduced. Another known approach to reducing effector functions is to inhibit production of or remove the N-linked glycans at position 297 (EU numbering) in the CH2 domain of the Fc (Nose et al., 1983 *PNAS* 80: 6632; Leatherbarrow et al., 1985 *Mol. Immunol.* 22: 407; Tao et al., 1989 *J. Immunol.* 143: 2595; Lund et al., 1990 *Mol. Immunol.* 27: 1145; Dorai et al., 1991 *Hybridoma* 10:211; Hand et al., 1992 *Cancer Immunol. Immunother.* 35:165; Leader et al., 1991 *Immunology* 72: 481; Pound et al., 1993 *Mol. Immunol.* 30:233; Boyd et al., 1995 *Mol. Immunol.* 32: 1311). It is also known that different glycoforms can profoundly affect the properties of a therapeutic, including pharmacokinetics, pharmacodynamics, receptor-interaction and tissue-specific targeting (Graddis et al., 2002, *Curr Pharm Biotechnol.* 3: 285-297). In particular, for antibodies, the oligosaccharide structure can affect properties relevant to protease resistance, the serum half-life of the antibody mediated by the FcRn receptor, phagocytosis and antibody feedback, in addition to effector functions of the antibody (e.g., binding to the complement complex C1, which induces CDC, and binding to FcγR receptors, which are responsible for modulating the ADCC pathway) (Nose and Wigzell, 1983; Leatherbarrow and Dwek, 1983; Leatherbarrow et al., 1985; Walker et al., 1989; Carter et al., 1992, *PNAS,* 89: 4285-4289).

Accordingly, another means of modulating effector function of antibodies includes altering glycosylation of the antibody constant region. Altered glycosylation includes, for example, a decrease or increase in the number of glycosylated residues, a change in the pattern or location of glycosylated residues, as well as a change in sugar structure(s). The oligosaccharides found on human IgGs affects their degree of effector function (Raju, T. S. *BioProcess International* April 2003. 44-53); the microheterogeneity of human IgG oligosaccharides can affect biological functions such as CDC and ADCC, binding to various Fc receptors, and binding to C1q protein (Wright A. & Morrison SL. TIBTECH 1997, 15 26-32; Shields et al. *J Biol Chem.* 2001 276(9):6591-604; Shields et al. *J Biol Chem.* 2002; 277(30): 26733-40; Shinkawa et al. *J Biol Chem.* 2003 278(5):3466-73; Umana et al. *Nat Biotechnol.* 1999 February; 17(2): 176-80). For example, the ability of IgG to bind C1q and activate the complement cascade may depend on the presence, absence or modification of the carbohydrate moiety positioned between the two CH2 domains (which is normally anchored at Asn297) (Ward and Ghetie, *Therapeutic Immunology* 2:77-94 (1995).

Glycosylation sites in an Fc-containing polypeptide, for example an antibody such as an IgG antibody, may be identified by standard techniques. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline. Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see NetNGlyc services for predicting N-linked glycosylation sites and NetOGlyc services for predicting O-linked glycosylation sites).

In vivo studies have confirmed the reduction in the effector function of aglycosyl antibodies. For example, an aglycosyl anti-CD8 antibody is incapable of depleting CD8-bearing cells in mice (Isaacs, 1992 *J. Immunol.* 148: 3062) and an aglycosyl anti-CD3 antibody does not induce cytokine release syndrome in mice or humans (Boyd, 1995 supra; Friend, 1999 *Transplantation* 68:1632).

Importantly, while removal of the glycans in the CH2 domain appears to have a significant effect on effector function, other functional and physical properties of the antibody remains unaltered. Specifically, it has been shown that removal of the glycans had little to no effect on serum half-life and binding to antigen (Nose, 1983 supra; Tao, 1989 supra; Dorai, 1991 supra; Hand, 1992 supra; Hobbs, 1992 *Mol. Immunol.* 29:949).

Although there is in vivo validation of the aglycosyl approach, there are reports of residual effector function with aglycosyl mAbs (see, e.g., Pound, J. D. et al. (1993) *Mol. Immunol.* 30(3): 233-41; Dorai, H. et al. (1991) *Hybridoma* 10(2): 211-7). Armour et al. show residual binding to FcγRIIa and FcγRIIb proteins (*Eur. J. Immunol.* (1999) 29: 2613-1624; *Mol. Immunol.* 40 (2003) 585-593). Thus a further decrease in effector function, particularly complement activation, may be important to guarantee complete ablation of activity in some instances. For that reason, aglycosyl forms of IgG2 and IgG4 and a G1/G4 hybrid are envisioned as being useful in methods and antibody compositions of the invention having reduced effector functions.

The anti-αvβ6 antibodies of the present invention may be modified or altered to elicit reduced effector function(s) (compared to a second αvβ6-specific antibody) while optionally retaining the other valuable attributes of the Fc portion.

Accordingly, in certain embodiments, the present invention relates to aglycosyl anti-αvβ6 antibodies with decreased effector function, which are characterized by a modification at the conserved N-linked site in the CH2 domains of the Fc portion of the antibody. A modification of the conserved N-linked site in the CH2 domains of the Fc dimer can lead to aglycosyl anti-αvβ6 antibodies. Examples of such modifications include mutation of the conserved N-linked site in the CH2 domains of the Fc dimer, removal of glycans attached to the N-linked site in the CH2 domains, and prevention of glycosylation. For example, an aglycosyl anti-αvβ6 antibody may be created by changing the canonical N-linked Asn site in the heavy chain CH2 domain to a Gln residue (see, for example, WO 05/03175 and US 2006-0193856).

In one embodiment of present invention, the modification comprises a mutation at the heavy chain glycosylation site to prevent glycosylation at the site. Thus, in one embodiment of this invention, the aglycosyl anti-αvβ6 antibodies are prepared by mutation of the heavy chain glycosylation site, i.e., mutation of N298Q (N297 using Kabat EU numbering) and expressed in an appropriate host cell. For example, this mutation may be accomplished by following the manufacturer's recommended protocol for unique site mutagenesis kit from Amersham-Pharmacia Biotech® (Piscataway, N.J., USA).

The mutated antibody can be stably expressed in a host cell (e. g. NSO or CHO cell) and then purified. As one example, purification can be carried out using Protein A and gel filtration chromatography. It will be apparent to those of skill in the art that additional methods of expression and purification may also be used.

In another embodiment of the present invention, the aglycosyl anti-αvβ6 antibodies have decreased effector function, wherein the modification at the conserved N-linked site in the CH2 domains of the Fc portion of said antibody or antibody derivative comprises the removal of the CH2 domain glycans, i.e., deglycosylation. These aglycosyl anti-αvβ6 antibodies may be generated by conventional methods and then deglycosylated enzymatically. Methods for enzymatic deglycosylation of antibodies are well known to those of skill in the art (Williams, 1973; Winkelhake & Nicolson, 1976 *J. Biol Chem.* 251:1074-80.).

In another embodiment of this invention, deglycosylation may be achieved by growing host cells which produce the antibodies in culture medium comprising a glycosylation inhibitor such as tunicamycin (Nose & Wigzell, 1983). That is, the modification is the reduction or prevention of glycosylation at the conserved N-linked site in the CH2 domains of the Fc portion of said antibody.

In other embodiments of this invention, recombinant X polypeptides (or cells or cell membranes containing such polypeptides) may be used as an antigen to generate an anti-αvβ6 antibody or antibody derivatives, which may then be deglycosylated.

In alternative embodiments, agyclosyl anti-αvβ6 antibodies or anti-αvβ6 antibodies with reduced glycosylation may be produced by the method described in Taylor et al. (WO 05/18572 and US 2007-0048300). For example, in one embodiment, an anti-αvβ6 aglycosyl antibody may be produced by altering a first amino acid residue (e.g., by substitution, insertion, deletion, or by chemical modification), wherein the altered first amino acid residue inhibits the glycosylation of a second residue by either steric hindrance or charge or both. In certain embodiments, the first amino acid residue is modified by amino acid substitution. In further embodiments, the amino acid substitution is selected from the group consisting of Gly, Ala, Val, Leu, Ile, Phe, Asn, Gln, Trp, Pro, Ser, Thr, Tyr, Cys, Met, Asp, Glu, Lys, Arg, and His. In other embodiments, the amino acid substitution is a non-traditional amino acid residue. The second amino acid residue may be near or within a glycosylation motif, for example, an N-linked glycosylation motif that contains the amino acid sequence NXT or NXS. In one exemplary embodiment, the first amino acid residue is amino acid 299 and the second amino acid residue is amino acid 297, according to the Kabat numbering. For example, the first amino acid substitution may be T299A, T299N, T299G, T299Y, T299C, T299H, T299E, T299D, T299K, T299R, T299G, T299I, T299L, T299M, T299F, T299P, T299W, and T299V, according to the Kabat numbering. In particular embodiments, the amino acid substitution is T299C.

Effector function may also be reduced by modifying an antibody of the present invention such that the antibody contains a blocking moiety. Exemplary blocking moieties include moieties of sufficient steric bulk and/or charge such that reduced glycosylation occurs, for example, by blocking the ability of a glycosidase to glycosylate the polypeptide. The blocking moiety may additionally or alternatively reduce effector function, for example, by inhibiting the ability of the Fc region to bind a receptor or complement protein. In some embodiments, the present invention relates to an αvβ6-binding protein, e.g., an anti-αvβ6 antibody, comprising a variant Fc region, the variant Fc region comprising a first amino acid residue and an N-glycosylation site, the first amino acid residue modified with side chain chemistry to achieve increased steric bulk or increased electrostatic charge compared to the unmodified first amino acid residue, thereby reducing the level of or otherwise altering glycosylation at the N-glycosylation site. In certain of these embodiments, the variant Fc region confers reduced effector function compared to a control, non-variant Fc region. In further embodiments, the side chain with increased steric bulk is a side chain of an amino acid residue selected from the group consisting of Phe, Trp, His, Glu, Gln, Arg, Lys, Met and Tyr. In yet further embodiments, the side chain chemistry with increased electrostatic charge is a side chain of an amino acid residue selected from the group consisting of Asp, Glu, Lys, Arg, and His.

Accordingly, in one embodiment, glycosylation and Fc binding can be modulated by substituting T299 with a charged side chain chemistry such as D, E, K, or R. The resulting antibody will have reduced glycosylation as well as reduced Fc binding affinity to an Fc receptor due to unfavorable electrostatic interactions.

In another embodiment, a T299C variant antibody, which is both aglycosylated and capable of forming a cysteine adduct, may exhibit less effector function (e.g., FcγRI binding) compared to its aglycosylated antibody counterpart (see, e.g., WO 05/18572). Accordingly, alteration of a first amino acid proximal to a glycosylation motif can inhibit the glycosylation of the antibody at a second amino acid residue; when the first amino acid is a cysteine residue, the antibody may exhibit even further reduced effector function. In addition, inhibition of glycosylation of an antibody of the IgG4 subtype may have a more profound affect on FcγRI binding compared to the effects of agycosylation in the other subtypes.

In additional embodiments, the present invention relates to anti-αvβ6 antibodies with altered glycosylation that exhibit reduced binding to one or more FcR receptors and that optionally also exhibit increased or normal binding to one or more Fc receptors and/or complement—e.g., antibodies with altered glycosylation that at least maintain the same or similar binding affinity to one or more Fc receptors and/or complement as a native, control anti-αvβ6 antibody). For example, anti-αvβ6 antibodies with predominantly Man$_5$GlcNAc$_2$N-glycan as the glycan structure present (e.g., wherein Man$_5$GlcNAc$_2$N-glycan structure is present at a level that is at least about 5 mole percent more than the next predominant glycan structure of the Ig composition) may exhibit altered effector function compared to an anti-αvβ6 antibody population wherein Man$_5$GlcNAc$_2$N-glycan structure is not predominant Antibodies with predominantly this glycan structure exhibit decreased binding to FcγRIIa and FcγRIIb, increased binding to FcγRIIIa and FcγRIIIb, and increased binding to C1q subunit of the C1 complex (see US 2006-0257399). This glycan structure, when it is the predominant glycan structure, confers increased ADCC, increased CDC, increased serum half-life, increased antibody production of B cells, and decreased phagocytosis by macrophages.

In general, the glycosylation structures on a glycoprotein will vary depending upon the expression host and culturing conditions (Raju, T S. BioProcess *International* April 2003. 44-53). Such differences can lead to changes in both effector function and pharmacokinetics (Israel et al. Immunology. 1996; 89(4):573-578; Newkirk et al. P. Clin. Exp. 1996; 106(2):259-64). For example, galactosylation can vary with cell culture conditions, which may render some immunoglobulin compositions immunogenic depending on their specific galactose pattern (Patel et al., 1992. *Biochem* 1 285: 839-845). The oligosaccharide structures of glycoproteins produced by non-human mammalian cells tend to be more closely related to those of human glycoproteins. Further, protein expression host systems may be engineered or selected to express a predominant Ig glycoform or alternatively may naturally produce glycoproteins having predominant glycan structures. Examples of engineered protein expression host systems producing a glycoprotein having a predominant glycoform include gene knockouts/mutations (Shields et al., 2002, *JBC,* 277: 26733-26740); genetic engineering in (Umana et al., 1999, *Nature Biotech.,* 17: 176-180) or a combination of both. Alternatively, certain cells naturally express a predominant glycoform—for example, chickens, humans and cows (Raju et al., 2000, *Glycobiology,* 10: 477-486). Thus, the expression of an anti-αvβ6 antibody or antibody composition having altered glycosylation (e.g., predominantly one specific glycan structure) can be obtained by one skilled in the art by selecting at least one of many expression host systems. Protein expression host systems that may be used to produce anti-αvβ6 antibodies of the present invention include animal, plant, insect, bacterial cells and the like. For example, US 2007-0065909, 2007-0020725, and 2005-0170464 describe producing aglycosylated immunoglobulin molecules in bacterial cells. As a further example, Wright and Morrison produced antibodies in a CHO cell line deficient in glycosylation (1994 *J Exp Med* 180: 1087-1096) and showed that antibodies produced in this cell line were incapable of complement-mediated cytolysis. Other examples of expression host systems found in the art for production of glycoproteins include: CHO cells: Raju WO 99/22764 and Presta WO 03/35835; hybridoma cells: Trebak et al., 1999, *J. Immunol. Methods,* 230: 59-70; insect cells: Hsu et al., 1997, *JBC,* 272:9062-970, and plant cells: Gerngross et al., WO 04/74499. To the extent that a given cell or extract has resulted in the glycosylation of a given motif, art recognized techniques for determining if the motif has been glycosylated are available, for example, using gel electrophoresis and/or mass spectroscopy.

Additional methods for altering glycosylation sites of antibodies are described, e.g., in U.S. Pat. No. 6,350,861 and U.S. Pat. No. 5,714,350, WO 05/18572 and WO 05/03175; these methods can be used to produce anti-αvβ6 antibodies of the present invention with altered, reduced, or no glycosylation.

The aglycosyl anti-αvβ6 antibodies with reduced effector function may be antibodies that comprise modifications or that may be conjugated to comprise a functional moiety. Such moieties include a blocking moiety (e.g., a PEG moiety, cysteine adducts, etc.), a detectable moiety (e.g., fluorescent moieties, radioisotopic moieties, radiopaque moieties, etc., including diagnostic moieties), a therapeutic moiety (e.g., cytotoxic agents, anti-inflammatory agents, immunomodulatory agents, anti-infective agents, anti-cancer agents, anti-neurodegenerative agents, radionuclides, etc.), and/or a binding moiety or bait (e.g., that allows the antibody to be pre-targeted to a tumor and then to bind a second molecule, composed of the complementary binding moiety or prey and a detectable moiety or therapeutic moiety, as described above).

Indications

The anti-αvβ6 antibodies or antigen-binding fragments thereof described herein can be used in the diagnosis and treatment, including prevention, of αvβ6-mediated diseases. The antibodies or antigen-binding fragments thereof can be conjugated to an agent (e.g., cytotoxic agent, siRNA, miRNA, anti-miR, small molecule, or other chemical moiety) that is useful to treat or prevent the disease being treated or prevented with the anti-αvβ6 antibodies or antigen-binding fragments thereof. In some embodiments, the antibodies or antigen-binding fragments thereof described herein can be used as anti-fibrotics. In other embodiments, the antibodies or antigen-binding fragments thereof described herein can be used to protect against epithelial and/or endothelial cell injury. In certain embodiments, the antibodies or antigen-binding fragments thereof described herein can be used to reduce or prevent alveolar epithelial injury. In yet other embodiments, the antibodies or antigen-binding fragments thereof described herein can be used to treat cancer. In further embodiments, the antibodies or antigen-binding fragments thereof described herein can be used to block interaction of the αvβ6 receptor with RGD-containing ligands, e.g., proteins on the surface of viruses, thereby reducing or preventing viral infection.

The antibodies or antigen-binding fragments thereof of this disclosure can be used to diagnose, treat, or prevent fibrosis (e.g., lung fibrosis (e.g., idiopathic pulmonary fibrosis (IPF); usual interstitial pneumonia (UIP)), kidney fibrosis, or liver fibrosis), acute lung injury, acute kidney injury, acute liver injury, Alport's Syndrome, scleroderma, sarcoidosis, amyloidosis, histiocytosis X, idiopathic nephrotic syndrome, idiopathic membranoproliferative glomerulonephritis, idiopathic restrictive cardiomyopathy, and cancer (e.g., pancreatic, lung, breast, colorectal, head and neck, esophageal, skin, prostate, cervical, ovarian, kidney, or endometrial cancer) among other diseases and disorders, by blocking the activation of TGF-β, or by blocking the binding of αvβ6 to any of its other ligands, such as, fibronectin, vitronectin, and tenascin.

In some embodiments, the antibodies or antigen-binding fragments thereof described herein can be used to treat lung diseases associated with injury/fibrosis such as, but not limited to, idiopathic pulmonary fibrosis, radiation induced fibrosis, flu induced fibrosis, coagulation induced fibrosis, vascular injury induced fibrosis, lung disease with usual interstitial pneumonia, chronic obstructive pulmonary disease (COPD), scleroderma, bleomycin induced fibrosis, asthma (e.g., chronic asthma), silicosis, asbestos induced fibrosis, acute lung injury and acute respiratory distress, (including bacterial pneumonia induced, trauma induced, viral pneumonia induced, ventilator induced, non-pulmonary sepsis induced and aspiration induced). The antibodies described herein can also be used to treat chronic nephropathies associated with injury/fibrosis such as, but not limited to, lupus, diabetes, scleroderma, glomerular nephritis, focal segmental glomerular sclerosis, IgA nephropathy, hypertension, allograft and Alport's disease. The antibodies can also be used to treat gut fibrosis, scleroderma, and radiation-induced fibrosis. The antibodies can also be used to treat liver fibrosis such as, but not limited to, biliary duct injury induced fibrosis. The antibodies described herein can also be used to treat kidney fibrosis disease, such as in a human subject with diabetes or focal segmental glomerular sclerosis (FSGS). In certain embodiments, the antibodies described herein can also be used to treat acute exacerbations of idiopathic pulmonary fibrosis. Other indications which the antibodies described herein can be used to treat include head and neck fibrosis, radiation induced fibrosis, corneal scarring, LASIX, corneal transplant, trabeculectomy, hypertrophic scarring, burn induced fibrosis, surgical fibrosis, sarcoidosis, psoriasis, and spinal cord injury/fibrosis.

The antibodies or antigen-binding fragments thereof described herein are also useful in treating cancer or cancer metastasis (including tumor growth and invasion), particularly epithelial cancers. A subset of epithelial cancers includes squamous cell carcinoma, e.g., head and neck (including oral, laryngeal, pharyngeal, esophageal), breast, lung, prostate, cervical, colon, pancreatic, skin (basal cell carcinomas) and ovarian cancers. αvβ6 is highly expressed in many epithelial cancers, especially on the leading edge of the tumors.

The present disclosure includes methods of treating or preventing metastatic cancers by identifying pre-invasive lesions or carcinomas in patients, and treating the patient to eliminate the pre-invasive lesion before it has the opportunity to evolve into an invasive form. Such methods comprise, for example, (a) obtaining a tissue sample that is suspected of containing a cancer or a pre-invasive lesion, and a tissue sample that does not contain a cancer or pre-invasive lesion (preferably from the same tissue or organ as that suspected of containing a cancer or pre-invasive lesion); (b) contacting the tissue samples with one or more αvβ6-binding ligands, such as one or more αvβ6-binding antibodies or antigen-binding fragments thereof, under conditions favoring the binding of the one or more αvβ6-binding antibodies or antigen-binding fragments thereof to αvβ6 integrins in the tissue wherever present; and (c) detecting the level or pattern of binding of the αvβ6-binding ligand(s) to the tissue, wherein an increase in the localized binding of the αvβ6-binding ligand in the myoepithelium surrounding a hyperplasia (e.g., a tumor) relative to the binding in the hyperplasia itself (or cells thereof), or an increase in the level of binding of the αvβ6-binding ligand in the tissue sample containing the cancerous or pre-invasive lesion relative to the binding in the non-cancerous tissue sample (or cells thereof), is indicative of carcinoma that is more likely to become invasive and potentially metastasize. In other related embodiments, the invention contemplates methods of reducing or preventing the progression of a pre-metastatic or pre-invasive tumor to a metastatic or invasive tumor in a patient, comprising administering to the patient a therapeutically effective amount of one or more ligands that bind to one or more subunits of integrin αvβ6 on one or more cells in the pre-metastatic or pre-invasive tumor, wherein the binding of the ligand to the integrin results in the reduction or prevention of invasion of cells of the pre-metastatic or pre-invasive cancer into tissue areas surrounding the primary tumor. In other embodiments, the methods of the invention are suitable for eliminating residual tumor cells, e.g., of residual metastatic cells, following removal, treatment or eradication of a tumor by a different approach. For example, such methods can be used to eliminate residual tumor cells or metastatic cells that may remain in the patient following surgical excision of a tumor, or tumor eradication by methods such as irradiation, chemotherapy and the like. In such therapeutic regimens, the methods of the invention may comprise administering the αvβ6-binding antibodies or antigen-binding fragments thereof, to a patient prior to, during, and/or following surgical, radiological and/or chemotherapeutic ablation of the tumor.

The efficacy of the antibodies of the invention can be assessed in various animal models. Mouse models for lung fibrosis include bleomycin-(Pittet et al., *J. Clin. Invest.*, 107(12):1537-1544 (2001); and Munger et al., *Cell*, 96:319-328 (1999)) and irradiation-inducible lung fibrosis (Franko et al., *Rad. Res.*, 140:347-355 (1994)). Mouse models for kidney fibrosis include COL4A3−/− mice (see, e.g., Cosgrove et al., *Amer. J. Path.*, 157:1649-1659 (2000), mice with adriamycin-induced injury (Wang et al., *Kidney International*, 58: 1797-1804 (2000); Deman et al., *Nephrol Dial Transplant*, 16: 147-150 (2001)), db/db mice (Ziyadeh et al., *Proc. Natl. Acad. Sci. USA*, 97:8015-8020 (2000)), and mice with unilateral ureteral obstruction (Fogo et al., *Lab Investigation*, 81: 189A (2001); and Fogo et al., *Journal of the American Society of Nephrology*, 12:819 A (2001)). αvβ6 antibodies described herein can be assessed for their ability to inhibit tumor growth, progression, and metastasis in standard in vivo tumor growth and metastasis models. See, e.g., Rockwell et al., *J. Natl. Cancer Inst.*, 49:735 (1972); Guy et al., *Mol. Cell Biol.*, 12:954 (1992); Wyckoff et al., *Cancer Res.*, 60:2504 (2000); and Oft et al., *Curr. Biol.*, 8:1243 (1998).

The efficacy of treatments may be measured by a number of available diagnostic tools, including physical examination, blood tests, proteinuria measurements, creatinine levels and creatinine clearance, pulmonary function tests, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

Pharmaceutical Compositions

An anti-αvβ6 antibody or antigen-binding fragment thereof described herein can be formulated as a pharmaceutical composition for administration to a subject, e.g., to treat a disorder described herein. The anti-αvβ6 antibody or antigen-binding fragment thereof may be conjugated (e.g., to a cytotoxic agent, siRNA, miRNA, anti-miR, small molecule, or other chemical moiety). Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) *J. Pharm. Sci.* 66:1-19).

Pharmaceutical formulation is a well-established art, and is further described, e.g., in Gennaro (ed.), *Remington: The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients American Pharmaceutical Association*, 3$^{rd}$ ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, an anti-αvβ6 antibody described herein is formulated with excipient materials, such as sodium citrate, sodium dibasic phosphate heptahydrate, sodium monobasic phosphate, Tween-80, and a stabilizer. It can be provided, for example, in a buffered solution at a suitable concentration and can be stored at 2-8° C. In some other embodiments, the pH of the composition is between about 5.5 and 7.5 (e.g., 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5).

The pharmaceutical compositions can also include agents that reduce aggregation of the αvβ6 antibody or antigen-binding fragment thereof when formulated. Examples of aggregation reducing agents include one or more amino acids selected from the group consisting of methionine, arginine, lysine, aspartic acid, glycine, and glutamic acid. These amino acids may be added to the formulation to a concentration of about 0.5 mM to about 145 mM (e.g., 0.5 mM, 1 mM, 2 mM, 5 mM, 10 mM, 25 mM, 50 mM, 100 mM). The pharmaceutical compositions can also include a sugar (e.g., sucrose, trehalose, mannitol, sorbitol, or xylitol) and/or a tonicity modifier (e.g., sodium chloride, mannitol, or sorbitol) and/or a surfactant (e.g., polysorbate-20 or polysorbate-80).

Such compositions can be administered by a parenteral mode (e.g., intravenous, subcutaneous, intraperitoneal, or intramuscular injection). In one embodiment, the anti-αvβ6 antibody or antigen-binding fragment thereof compositions are administered by inhalation. In one embodiment, the anti-αvβ6 antibody or antigen-binding fragment thereof compositions are administered subcutaneously. In one embodiment, the anti-αvβ6 antibody or antigen-binding fragment thereof compositions are administered intravenously. The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the anti-αvβ6 antibody or antigen-binding fragment thereof may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York (1978).

In one embodiment, the pharmaceutical formulation comprises an anti-αvβ6 antibody or antigen-binding fragment thereof at a concentration of about 0.5 mg/mL to 500 mg/mL (e.g., 0.5 mg/mL, 1 mg/mL, 5 mg/mL, 10 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 250 mg/mL, 300 mg/mL, 350 mg/mL, 400 mg/mL, 450 mg/mL, 500 mg/mL), formulated with a pharmaceutically acceptable carrier. In some embodiments, the anti-αvβ6 antibody or antigen-binding fragment thereof is formulated in sterile distilled water or phosphate buffered saline. The pH of the pharmaceutical formulation may be between 5.5 and 7.5 (e.g., 5.5, 5.6, 5.7, 5.8, 5.9, 6.0, 6.1, 6.2 6.3, 6.4 6.5, 6.6 6.7, 6.8, 6.9 7.0, 7.1, 7.3, 7.4, 7.5).

Administration

The anti-αvβ6 antibody or antigen-binding fragment thereof can be administered to a subject, e.g., a subject in need thereof, for example, a human subject, by a variety of methods. For many applications, the route of administration is one of: intravenous injection or infusion (IV), subcutaneous injection (SC), intraperitoneally (IP), inhalation, or intramuscular injection. It is also possible to use intra-articular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration can be oral.

The route and/or mode of administration of the antibody or antigen-binding fragment thereof can also be tailored for the individual case, e.g., by monitoring the subject, e.g., using tomographic imaging, e.g., to visualize a tumor.

The antibody or antigen-binding fragment thereof can be administered as a fixed dose, or in a mg/kg dose. The dose can also be chosen to reduce or avoid production of antibodies against the anti-αvβ6 antibody. Dosage regimens are adjusted to provide the desired response, e.g., a therapeutic response or a combinatorial therapeutic effect. Generally, doses of the anti-αvβ6 antibody or antigen binding fragment thereof (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used. In certain embodiments, a subject in need of treatment with an anti-αvβ6 antibody or antigen binding fragment thereof is administered the antibody at a dose of 1 mg/kg to 30 mg/kg. In some embodiments, a subject in need of treatment with an anti-αvβ6 antibody or antigen-binding fragment thereof is administered the antibody at a dose of 1 mg/kg, 2 mg/kg, 4 mg/kg, 5 mg/kg, 7 mg/kg 10 mg/kg, 12 mg/kg, 15 mg/kg, 20 mg/kg, 25 mg/kg, 28 mg/kg, 30 mg/kg, 35 mg/kg, 40 mg/kg, or 50 mg/kg. In certain embodiments, a subject in need of treatment with a toxin-conjugated anti-αvβ6 antibody or antigen binding fragment thereof is administered the toxin-conjugated antibody or antigen binding fragment thereof at a dose of 0.1 mg/kg to 30 mg/kg. In some embodiments, a subject in need of treatment with a toxin-conjugated anti-αvβ6 antibody or antigen-binding fragment thereof is administered the toxin-conjugated antibody or antigen binding fragment thereof at a dose of 0.1 mg/kg, 0.2 mg/kg, 0.3 mg/kg, 0.4 mg/kg, 0.5 mg/kg, 0.6 mg/kg, 0.7 mg/kg, 0.75 mg/kg, 0.8 mg/kg, 0.9 mg/kg, 1 mg/kg, 2 mg/kg, 4 mg/kg, 5 mg/kg, 7 mg/kg 10 mg/kg, 12 mg/kg, 15 mg/kg, 20 mg/kg, 25 mg/kg, 28 mg/kg, 30 mg/kg, 35 mg/kg, 40 mg/kg, or 50 mg/kg. In a specific embodiment, the antibodies or antigen-binding fragments thereof are administered subcutaneously at a dose of 1 mg/kg to 3 mg/kg. In another embodiment, the antibodies or antigen-binding fragments thereof are administered intravenously at a dose of 4 mg/kg to 30 mg/kg. In certain embodiments, the toxin-conjugated versions of the antibodies or antigen-binding fragments thereof are administered intravenously at a dose of 0.1 mg/kg to 30 mg/kg.

A composition may comprise about 1 mg/mL to 100 µg/ml or about 10 mg/mL to 100 µg/ml or about 50 to 250 mg/mL or about 100 to 150 µg/ml or about 100 to 250 µg/ml of anti-αvβ6 antibody or an antigen-binding fragment thereof. In certain embodiments, the anti-αvβ6 antibody or antigen-binding fragment thereof in a composition is predominantly in monomeric form, e.g., at least about 90%, 92%, 94%, 96%, 98%, 98.5% or 99% in monomeric form. Certain anti-αvβ6 antibody or antigen-binding fragment thereof compositions may comprise less than about 5, 4, 3, 2, 1, 0.5, 0.3 or 0.1% aggregates, as detected, e.g., by UV at A280 nm. Certain anti-αvβ6 antibody or antigen-binding fragment thereof compositions comprise less than about 5, 4, 3, 2, 1, 0.5, 0.3, 0.2 or 0.1% fragments, as detected, e.g., by UV at A280 nm.

Dosage unit form or "fixed dose" as used herein refers to physically discrete units suited as unitary dosages for the subjects to be treated; each unit contains a predetermined quantity of anti-αvβ6 antibody calculated to produce the desired therapeutic effect in association with the required pharmaceutical carrier and optionally in association with the other agent. Single or multiple dosages may be given. Alternatively, or in addition, the antibody may be administered via continuous infusion.

An anti-αvβ6 antibody or antigen-binding fragment thereof dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

If a subject is at risk for developing a disorder described herein, the antibody can be administered before the full onset of the disorder, e.g., as a preventative measure. The duration of such preventative treatment can be a single dosage of the antibody or the treatment may continue (e.g., multiple dosages). For example, a subject at risk for the disorder or who has a predisposition for the disorder may be treated with the antibody for days, weeks, months, or even years so as to prevent the disorder from occurring or fulminating.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

In certain embodiments, the anti-αvβ6 antibody or antigen-binding fragment thereof is administered subcutaneously at a concentration of about 1 mg/mL to about 500 mg/mL (e.g., 1 mg/mL, 2 mg/mL, 3 mg/mL, 4 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 400 mg/mL, 450 mg/mL). In one embodiment, the anti-αvβ6 antibody or antigen-binding fragment thereof is administered subcutaneously at a concentration of 50 mg/mL. In another embodiment, the anti-αvβ6 antibody or antigen-binding fragment thereof is administered intravenously at a concentration of about 1 mg/mL to about 500 mg/mL. In a particular embodiment, the anti-αvβ6 antibody or antigen-binding fragment thereof is administered intravenously at a concentration of 50 mg/mL.

The anti-αvβ6 antibody or antigen-binding fragment thereof can be administered to a patient in need thereof (e.g., a patient with a fibrotic disorder) in combination with an antagonist (e.g., antibodies, polypeptide antagonists, and/or small molecule antagonists) of one or more: other integrin receptors (e.g., α1β1, α4β1, αvβ8, αvβ5, αvβ1, αvβ3, etc.); cytokines (e.g., TGF-β, IL-4, IL-13, IL-17); chemokines (e.g., CCL2, CXCL8, CXCL12); growth factors (e.g., Connective tissue growth factor (CTGF), Platelet-derived growth factor (PDGF), Vascular endothelial growth factor (VEGF), Fibroblast growth factor (FGF), Insulin-like growth factor-1 (IGF-1)), and/or small secreted signaling proteins (e.g., Wnt proteins, endothelin-1). In certain embodiments, the anti-αvβ6 antibody or antigen-binding fragment thereof is conjugated to a miRNA, siRNA, anti-miR, small molecule, cytotoxic agent, or other chemical moiety.

Devices and Kits for Therapy

Pharmaceutical compositions that include the anti-αvβ6 antibody or antigen-binding fragment thereof can be administered with a medical device. The device can be designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include anti-αvβ6 antibody or antigen-binding fragment thereof, and can be configured to deliver one or more unit doses of the antibody. The device can be further configured to administer a second agent, e.g., a chemo therapeutic agent, either as a single pharmaceutical composition that also includes the anti-αvβ6 antibody or antigen-binding fragment thereof or as two separate pharmaceutical compositions.

The pharmaceutical composition may be administered with a syringe. The pharmaceutical composition can also be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

An anti-αvβ6 antibody or antigen-binding fragment thereof can be provided in a kit. In one embodiment, the kit includes (a) a container that contains a composition that includes anti-αvβ6 antibody, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein (e.g., an antagonist (e.g., antibodies, polypeptide antagonists, and/or small molecule antagonists) of one or more: other integrin receptors (e.g., α1β1, α4β1, αvβ8, αvβ5, αvβ1, etc.); cytokines (e.g., TGF-β, IL-4, IL-13, IL-17); chemokines (e.g., CCL2, CXCL8, CXCL12); growth factors (e.g., Connective tissue growth factor (CTGF), Platelet-derived growth factor (PDGF), Vascular endothelial growth factor (VEGF), Fibroblast growth factor (FGF), Insulin-like growth factor-1 (IGF-1)), LPA1 (lysophosphatidic acid receptor), LOX (lysyloxidase), LOXL2 (lysyloxidase 2), small secreted signaling proteins (e.g., Wnt proteins, endothelin-1) a steroid, a cytotoxic compound, a radioisotope, a prodrug-activating enzyme, colchicine, oxygen, an antioxidant (e.g., N-acetylcysteine), a metal chelator (e.g., terathiomolybdate), IFN-β, IFN-γ, alpha-antitrypsin). For example, the kit includes a first container that contains a composition that includes the anti-αvβ6 antibody, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-αvβ6 antibody or antigen-binding fragment thereof, e.g., in a suitable dose, dosage form, or mode of administration (e.g., a dose, dosage form, or mode of administration described herein), to treat a subject who has had or who is at risk for an immunological disorder described herein. The information can be provided in a variety of formats, include printed text, computer readable material, video recording, or audio recording, or information that provides a link or address to substantive material, e.g., on the internet.

In addition to the antibody, the composition in the kit can include other ingredients, such as a solvent or buffer, a stabilizer, or a preservative. The antibody can be provided in any form, e.g., liquid, dried or lyophilized form, preferably substantially pure and/or sterile. When the agents are provided in a liquid solution, the liquid solution preferably is an aqueous solution. In certain embodiments, the antibody or antigen binding fragment thereof in the liquid solution is at a concentration of about 25 mg/mL to about 250 mg/mL (e.g., 40 mg/mL, 50 mg/mL, 60 mg/mL, 75 mg/mL, 85 mg/mL, 100 mg/mL, 125 mg/mL, 150 mg/mL, 200 mg/mL). When the antibody or antigen binding fragment is provided as a lyophilized product, the antibody or antigen binding fragment is at about 75 mg/vial to about 200 mg/vial (e.g., 100 mg/vial, 108.5 mg/vial, 125 mg/vial, 150 mg/vial). The lyophilized powder is generally reconstituted by the addition of a suitable solvent. The solvent, e.g., sterile water or buffer (e.g., PBS), can optionally be provided in the kit. In certain embodiments, the lyophilized product is at 108.5 mg/vial and reconstituted to a liquid solution at a concentration of 75 mg/mL.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-αvβ6 antibody or antigen-binding fragment thereof and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Diagnostic Uses

Anti-αvβ6 antibodies or antigen-binding fragments thereof can be used in a diagnostic method for detecting the presence of αvβ6 in vivo (e.g., in vivo imaging in a subject). For example, anti-αvβ6 antibodies can be administered to a subject to detect αvβ6 within the subject. For example, the antibody can be labeled, e.g., with an MRI detectable label or a radiolabel. The subject can be evaluated using a means for detecting the detectable label. For example, the subject can be scanned to evaluate localization of the antibody within the subject. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{33}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, can also be employed. The protein ligand can be labeled with such reagents using known techniques. For example, see Wensel and Meares (1983) *Radioimmunoimaging and Radioimmunotherapy*, Elsevier, New York for techniques relating to the radiolabeling of antibodies and Colcher et al. (1986) *Meth. Enzymol.* 121: 802-816.

The subject can be "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP0 502 814 A. Generally, the differences related to relaxation time constants T1 and T2 of water protons in different environments are used to generate an image. However, these differences can be insufficient to provide sharp high resolution images.

The differences in these relaxation time constants can be enhanced by contrast agents. Examples of such contrast agents include a number of magnetic agents, paramagnetic agents (which primarily alter T1) and ferromagnetic or superparamagnetic agents (which primarily alter T2 response). Chelates (e.g., EDTA, DTPA and NTA chelates) can be used to attach (and reduce toxicity) of some paramagnetic substances (e.g., $Fe^{3+}$, $Mn^{2+}$, $Gd^{3+}$). Other agents can be in the form of particles, e.g., less than 10 μm to about 10 nm in diameter). Particles can have ferromagnetic, anti-ferromagnetic or superparamagnetic properties. Particles can include, e.g., magnetite ($Fe_3O_4$), γ-$Fe_2O_3$, ferrites, and other magnetic mineral compounds of transition elements. Magnetic particles may include one or more magnetic crystals with and without nonmagnetic material. The nonmagnetic material can include synthetic or natural polymers (such as sepharose, dextran, dextrin, starch and the like).

The anti-αvβ6 antibodies or antigen-binding fragments thereof can also be labeled with an indicating group containing the NMR-active $^{19}$F atom, or a plurality of such atoms inasmuch as (i) substantially all of naturally abundant fluorine atoms are the $^{19}$F isotope and, thus, substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American*, 246:78-88 to locate and image αvβ6 distribution.

In another aspect, the disclosure provides a method for detecting the presence of αvβ6 in a sample in vitro (e.g., a biological sample, such as serum, plasma, tissue, biopsy). This method can be used to diagnose a disorder, e.g., fibrosis (e.g., lung fibrosis or kidney fibrosis) or cancer (e.g., pancreatic, lung, breast, colorectal, head and neck, esophageal, skin, cervical, prostate, ovarian, kidney, or endometrial). The method includes: (i) contacting the sample or a control sample with the anti-αvβ6 antibody; and (ii) evaluating the sample for the presence of αvβ6, e.g., by detecting formation of a complex between the anti-αvβ6 antibody and αvβ6, or by detecting the presence of the antibody or αvβ6. For example, the antibody can be immobilized, e.g., on a support, and retention of the antigen on the support is detected, and/or vice versa. The antibody used may be labeled e.g., with a fluorophore. A control sample can be included. The positive control can be a sample known to have the disease or disorder being assessed, and a negative control can be a sample from a subject who does not have the disease or disorder being assessed. A statistically significant change in the formation of the complex in the sample relative to the control sample can be indicative of the presence of αvβ6 in the sample. Generally, an anti-αvβ6 antibody can be used in applications that include fluorescence polarization, microscopy, ELISA, centrifugation, chromatography, and cell sorting (e.g., fluorescence activated cell sorting). In certain embodiments, the anti-αvβ6 antibody is a humanized 1A8 antibody or an antigen-binding fragment thereof. The tissue sample can be, e.g., skin biopsies from human patients with cancer, e.g., pancreatic, lung, breast, colorectal, head and neck, esophageal, skin, cervical, prostate, ovarian, kidney, or endometrial.

Cells from certain tumors that are metastatic express significantly enhanced levels of integrin αvβ6 when compared to cells that are less metastatic or non-metastatic. In addition, certain forms of in situ carcinoma, e.g., ductal carcinoma in situ (DCIS) or lobular carcinoma in situ (LCIS) of the breast, the myoepithelium surrounding the tumor expresses significantly enhanced levels of integrin αvβ6 relative to the tumor cells of the carcinoma and relative to normal breast tissue. Thus, the invention provides a method useful in diagnosing the metastatic potential of a tumor cell, including tumors from carcinomas such as an adenocarcinoma. In more particular embodiments, the carcinoma is a breast carcinoma, an endometrial carcinoma, a pancreatic carcinoma, a colorectal carcinoma, a lung carcinoma, an ovarian carcinoma, a cervical carcinoma, a prostatic carcinoma, a liver carcinoma, an esophageal carcinoma, a head and neck carcinoma, a stomach carcinoma or a splenic carcinoma. More particularly, the carcinoma is a breast carcinoma (including but not limited to an in situ breast carcinoma, such as ductal carcinoma in situ (DCIS) or lobular carcinoma in situ (LCIS)), an endometrial carcinoma, a pancreatic carcinoma, a colorectal carcinoma, a cervical carcinoma, or a lung carcinoma.

Methods according to this aspect of the invention involve assaying the level of expression of αvβ6 in the tumor cells or in the myoepithelium in a tissue sample, and comparing these expression levels with a control αvβ6 expression level (e.g., in normal cells, non-metastatic cells, or normal tissue, preferably obtained from the same animal, such as a human patient), wherein an increase in the expression of αvβ6 in a tumor or in the cells thereof is indicative of a higher invasive and/or metastatic potential of that tumor or cells thereof, or wherein an increase in the expression of αvβ6 in the myoepithelium surrounding a tumor or epithelial cell cluster in a tissue section is indicative of the presence of an in situ carcinoma, e.g., DCIS or LCIS, that is more likely to become invasive and potentially form metastases.

Where a diagnosis of a cancer has already been made according to conventional methods, the present invention is useful as a prognostic indicator, whereby tumor cells exhibiting increased levels of expression of αvβ6 will be predicted to be more likely to become invasive and to metastasize from the primary tumor site to a distal, metastatic site. Similarly, where a suspected diagnosis of an in situ carcinoma has been made according to conventional methods (e.g., mammographic detection of calcified nodules in the breast), the present invention is useful as a confirmatory indicator, whereby biopsied tissue from the area of calcification exhibiting increased levels of expression of αvβ6 in the myoepithelium indicates the presence of an in situ carcinoma, e.g., DCIS or LCIS that will become invasive and may respond to αvβ6 antibody treatment. Based on such prognostic and diagnostic outcomes, the treating physician can then adjust the treatment regimen accordingly, thereby providing for earlier detection of a pre-metastatic or pre-cancerous condition and thus a more favorable clinical outcome for the patient.

By "assaying the levels of expression of αvβ6" is intended qualitatively or quantitatively measuring or estimating the levels of αvβ6 in a first biological sample (e.g., a tumor sample, a tissue biopsy or aspirate, etc.) either directly (e.g., by determining or estimating absolute amount of $αvβ_6$ in the sample) or relatively (e.g., by comparing the level of expression of $αvβ_6$ in a first biological sample to that in a second biological sample). Preferably, the level of αvβ6 in the first biological sample is measured or estimated and compared to that in a standard taken from a second biological sample obtained from an individual not having a cancer or pre-cancerous lesion. As will be appreciated by one of ordinary skill in the art, once a standard αvβ6 expression level is known for a given non-cancerous tissue, it can be used repeatedly as a standard for comparison.

By "biological sample" is intended any biological sample obtained from an individual (such as a patient), cell line, tissue culture, or other source which may contain cells or cellular products such as extracellular matrix. Such biological samples include mammalian body tissues and cells, including leukocyte, ovary, prostate, heart, placenta, pancreas, liver, spleen, lung, breast, head and neck tissues (e.g., oral, pharyngeal, lingual and laryngeal tissues), endometrium, colon (or colorectal), cervix, stomach and umbilical tissues which may express αvβ6. Methods for obtaining tissue biopsies and body fluids from mammals are well known in the art. Exemplary mammals include monkeys, apes, cats, dogs, cows, pigs, horses, rabbits and humans. In one embodiment, the mammal is a human.

Assaying αvβ6 expression levels in a biological sample can occur using any art-known method. Preferred for assaying αvβ6 expression levels in a biological sample are immunological techniques. For example, αvβ6 expression in tissues can be studied with classical immunohistological methods. In these, the specific recognition is provided by a primary ligand, e.g., an antibody (polyclonal or monoclonal), that binds to αvβ6. This primary ligand can be labeled, e.g., with a fluorescent, chemiluminescent, phosphorescent, enzymatic or radioisotopic label. Alternatively, these methods of the invention can use a secondary detection system in which a second ligand that recognizes and binds to the αvβ6-binding ligand, e.g., a so-called "secondary" antibody which recognizes and binds to a first αvβ6-binding antibody, is detectably labeled as described above. As a result, an immunohistological staining of tissue section for pathological examination is obtained. Alternatively, tissues and cell samples can also be extracted, e.g., with urea and neutral detergent, for the liberation of αvβ6 protein for Western-blot or dot/slot assay (Jalkanen, M., et al., *J. Cell. Biol.*, 101: 976-985 (1985); Jalkanen, M., et al., *J. Cell. Biol.*, 105: 3087-3096 (1987)) for direct quantitation, relative to a standard tissue or cell sample known to have lower levels of expression of αvβ6.

As noted above, the methods of the present invention are useful for detecting metastatic cancers in mammals, for determining the metastatic potential of a tumor cell (i.e., predicting the likelihood that a given tumor cell will metastasize from the primary tumor site to a distal metastatic site), and for determining the likelihood that a noninvasive or in situ carcinoma will progress to an invasive or metastatic carcinoma. In particular the methods of the invention are useful in detecting invasive and/or metastatic cancers of epithelial tissues (i.e., invasive and/or metastatic carcinomas), including of the breast, ovary, prostate, liver, lung, pancreas, colon (or colorectal), head and neck tissues (e.g., oral, pharyngeal, lingual and laryngeal tissues), endometrium, cervix, stomach and spleen. Particularly suitable to detection by the methods of the present invention are invasive and/or metastatic adenocarcinomas, including but not limited to breast carcinomas, pancreatic carcinomas, colorectal carcinomas, cervical carcinomas, lung carcinomas, and in situ carcinomas, such as certain ductal carcinoma in situ (DCIS) or lobular carcinoma in situ (LCIS) of the breast, that are of increased likelihood to progress to an invasive and/or metastatic phenotype. Early identification and treatment of such carcinomas is associated with a better long-term prognosis for patients. For example, it has been reported that if left untreated, a significant proportion of DCIS tumors become invasive and can lead to metastatic cancers which have a much poorer prognosis (see Sakorafas, G. H., and Tsiotou, A. G. H., *Cancer Treatment Rev.*, 26:103-125 (2000)).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Humanized 1A8 Heavy and Light Chains

Structural models of the V regions of the mouse anti-αvβ6 antibody 1A8 were produced using Swiss PDB and analyzed in order to identify important "constraining" amino acids in the V regions that were likely to be essential for the binding properties of the antibody. Residues contained within the CDRs (using Kabat definition) together with a number of framework residues were considered to be important. Both the VH and Vκ sequences of 1A8 contain typical framework residues and the CDR 1, 2 and 3 motifs are comparable to many murine antibodies.

A set of sequence segments that could be used to create 1A8 Composite Human Antibody™ variants was selected and analyzed using iTope™ technology for in silico analysis of peptide binding to human MHC class II alleles (Perry et al., *Drugs R D*, 9(6):385-396 (2008)), and using the TCED™ of known antibody sequence-related T cell epitopes (Bryson et al., *Biodrugs*, 24(1):1-8 (2010)). Sequence segments that were identified as significant non-human germline binders to human MHC class II or that scored significant hits against the TCED™ were discarded. This resulted in a reduced set of segments, and combinations of these were again analyzed, as above, to ensure that the junctions between segments did not contain potential T cell epitopes. Selected segments were then combined to produce the six heavy and the three light chain V region sequences shown below.

1A8 VH1 Heavy Chain Amino Acid Sequence
(SEQ ID NO: 1)
QVQFVQSGPELKKPGASVKVSCKGSSYTFTDYTMHWVKLAHAKTLEWIG

VIDTYYGKTNYNQKFEGRATMTVDKSSSTAYMELARLRSEDSAVYYCAR

GGFRRGDRPSLRYAMDSWGQGTSVTVSS

1A8 VH1 Heavy Chain Nucleotide Sequence
(SEQ ID NO: 2)
CAGGTGCAGTTCGTGCAGTCCGGCCCCGAGCTGAAGAAGCCCGGCGCCT

CCGTGAAGGTGTCCTGCAAGGGCTCCTCCTACACCTTCACCGACTACAC

CATGCACTGGGTGAAGCTGGCCCACGCCAAGACCCTGGAGTGGATCGGC

GTGATCGACACCTACTACGGCAAGACCAACTACAACCAGAAGTTCGAGG

GCCGCGCCACCATGACCGTGGACAAGTCCTCCTCCACCGCCTACATGGA

GCTGGCCCGCCTGCGCTCCGAGGACTCCGCCGTGTACTACTGCGCCCGC

GGCGGCTTCCGCCGCGGCGACCGCCCCTCCCTGCGCTACGCCATGGACT

CCTGGGGCCAGGGCACCTCCGTGACCGTGTCCTCC

1A8 VH2 Heavy Chain Amino Acid Sequence
(SEQ ID NO: 3)
QVQLVQSGAEVKKPGASVKVSCKGSSYTFTDYTMHWVKLASAKTLEWI

GVIDTYYGKTNYNQKFEGRATMTVDKSSSTAYMELSSLRSEDTAVYYC

ARGGFRRGDRPSLRYAMDSWGQGTLVTVSS

1A8 VH2 Heavy Chain Nucleotide Sequence
(SEQ ID NO: 4)
CAGGTGCAGCTGGTGCAGTCCGGCGCCGAGGTGAAGAAGCCCGGCGCC

TCCGTGAAGGTGTCCTGCAAGGGCTCCTCCTACACCTTCACCGACTAC

ACCATGCACTGGGTGAAGCTGGCCTCCGCCAAGACCCTGGAGTGGATC

GGCGTGATCGACACCTACTACGGCAAGACCAACTACAACCAGAAGTTC

GAGGGCCGCGCCACCATGACCGTGGACAAGTCCTCCTCCACCGCCTAC

ATGGAGCTGTCCTCCCTGCGCTCCGAGGACACCGCCGTGTACTACTGC

GCCCGCGGCGGCTTCCGCCGCGGCGACCGCCCCTCCCTGCGCTACGCC

ATGGACTCCTGGGGCCAGGGCACCCTGGTGACCGTGTCCTCC

1A8 VH3 Heavy Chain Amino Acid Sequence
(SEQ ID NO: 5)
QVQLVQSGAEVKKPGASVKVSCKGSSYTFTDYTMHWVRLASAKTLEWI

GVIDTYYGKTNYNQKFEGRATMTVDKSSSTAYMELSSLRSEDTAVYYC

ARGGFRRGDRPSLRYAMDSWGQGTLVTVSS

1A8 VH3 Heavy Chain Nucleotide Sequence
(SEQ ID NO: 6)
CAGGTGCAGCTGGTGCAGTCCGGCGCCGAGGTGAAGAAGCCCGGCGCC

TCCGTGAAGGTGTCCTGCAAGGGCTCCTCCTACACCTTCACCGACTAC

ACCATGCACTGGGTGCGCCTGGCCTCCGCCAAGACCCTGGAGTGGATC

GGCGTGATCGACACCTACTACGGCAAGACCAACTACAACCAGAAGTTC

GAGGGCCGCGCCACCATGACCGTGGACAAGTCCTCCTCCACCGCCTAC

ATGGAGCTGTCCTCCCTGCGCTCCGAGGACACCGCCGTGTACTACTGC

GCCCGCGGCGGCTTCCGCCGCGGCGACCGCCCCTCCCTGCGCTACGCC

ATGGACTCCTGGGGCCAGGGCACCCTGGTGACCGTGTCCTCC

1A8 VH4 Heavy Chain Amino Acid Sequence
(SEQ ID NO: 7)
QVQLVQSGAEVKKPGASVKVSCKGSSYTFTDYTMHWVRLASAKTLEWI

GVIDTYYGKTNYNQKFEGRATITVDKSSSTAYMELSSLRSEDTAVYYC

ARGGFRRGDRPSLRYAMDSWGQGTLVTVSS

1A8 VH4 Heavy Chain Nucleotide Sequence
(SEQ ID NO: 8)
CAGGTGCAGCTGGTGCAGTCCGGCGCCGAGGTGAAGAAGCCCGGCGCC

TCCGTGAAGGTGTCCTGCAAGGGCTCCTCCTACACCTTCACCGACTAC

ACCATGCACTGGGTGCGCCTGGCCTCCGCCAAGACCCTGGAGTGGATC

GGCGTGATCGACACCTACTACGGCAAGACCAACTACAACCAGAAGTTC

GAGGGCCGCGCCACCATCACCGTGGACAAGTCCTCCTCCACCGCCTAC

ATGGAGCTGTCCTCCCTGCGCTCCGAGGACACCGCCGTGTACTACTGC

GCCCGCGGCGGCTTCCGCCGCGGCGACCGCCCCTCCCTGCGCTACGCC

ATGGACTCCTGGGGCCAGGGCACCCTGGTGACCGTGTCCTCC

1A8 VH5 Heavy Chain Amino Acid Sequence
(SEQ ID NO: 50)
QVQFVQSGPELKKPGASVKLSCKGSSYTFTDYTMHWVKLAHAKTLEWI

GVIDTYYGKTNYNQKFEGRATMTVDKSSTAYMETARLRSEDSAVYYC

ARGGFRRGDRPSLRYAMDSWGQGTSVTVSS

1A8 VH5 Heavy Chain Nucleotide Sequence
(SEQ ID NO: 51)
CAGGTGCAGTTCGTGCAGTCCGGCCCCGAGCTGAAGAAGCCCGGCGCC TCCGTGAAGcTGTCCTGCAAGGGCTCCTCCTACACCTTCACCGACTAC

ACCATGCACTGGGTGAAGCTGGCCCACGCCAAGACCCTGGAGTGGATC

GGCGTGATCGACACCTACTACGGCAAGACCAACTACAACCAGAAGTTC

GAGGGCCGCGCCACCATGACCGTGGACAAGTCCTCCTCCACCGCCTAC

ATGGAGacGGCCCGCCTGCGCTCCGAGGACTCCGCCGTGTACTACTGC

GCCCGCGGCGGCTTCCGCCGCGGCGACCGCCCCTCCCTGCGCTACGCC

ATGGACTCCTGGGGCCAGGGCACCTCCGTGACCGTGTCCTCC

1A8 VH6 Heavy Chain Amino Acid Sequence
(SEQ ID NO: 52)
QVQFVQSGPELKKPGASVKLSCKGSSYTFTDYTMHWVKLAHAKTLEWI

GVIDTYYGKTNYNQKFEKRATMTVDKSSTAYDETARLRSEDSAVYYC

ARGGFRRGDRPSLRYAMDSWGQGTSVTVSS

1A8 VH6 Heavy Chain Nucleotide Sequence
(SEQ ID NO: 53)
CAGGTGCAGTTCGTGCAGTCCGGCCCCGAGCTGAAGAAGCCCGGCGCC TCCGTGAAGcTGTCCTGCAAGGGCTCCTCCTACACCTTCACCGACTAC

ACCATGCACTGGGTGAAGCTGGCCCACGCCAAGACCCTGGAGTGGATC

GGCGTGATCGACACCTACTACGGCAAGACCAACTACAACCAGAAGTTC

GAGaaaCGCGCCACCATGACCGTGGACAAGTCCTCCTCCACCGCCTAC gacGAGacGGCCCGCCTGCGCTCCGAGGACTCCGCCGTGTACTACTGC

GCCCGCGGCGGCTTCCGCCGCGGCGACCGCCCCTCCCTGCGCTACGCC

ATGGACTCCTGGGGCCAGGGCACCTCCGTGACCGTGTCCTCC

1A8 Vκ1 Light Chain Amino Acid Sequence
(SEQ ID NO: 9)
DIVLTQSPDSLAVSLGERATINCRASQSVSISTYSYIHWFQQKPGQPP

KLLIKYASNLESGVPDRFSGSGSGTDFTLNIHPVEEEDVGIYYCQHSW

EIPYTFGGGTKVEIK

1A8 Vκ1 Light Chain Nucleotide Sequence
(SEQ ID NO: 10)
GACATCGTGCTGACCCAGTCCCCCGACTCCCTGGCCGTGTCCCTGGGC

GAGAGAGCCACCATCAACTGCCGCGCCTCCCAGTCCGTGTCCATCTCC

ACCTACTCCTACATCCACTGGTTCCAGCAGAAGCCCGGCCAGCCCCCC

AAGCTGCTGATCAAGTACGCCTCCAACCTGGAGTCCGGCGTGCCCGAC

CGCTTCTCCGGCTCCGGCTCCGGCACCGACTTCACCCTGAACATCCAC

CCCGTGGAGGAGGAGGACGTGGGCATCTACTACTGCCAGCACTCCTGG

GAGATCCCCTACACCTTCGGCGGCGGCACCAAGGTGGAGATCAAG

1A8 Vκ2 Light Chain Amino Acid Sequence
(SEQ ID NO: 11)
DIVLTQSPDSLAVSLGERATINCRASQSVSISTYSYIHWFQQKPGQPP

KLLIKYASNLESGVPDRFSGSGSGTDFTLKISRVEEEDVGIYYCQHSW

EIPYTFGGGTKVEIK

1A8 Vκ2 Light Chain Nucleotide Sequence
(SEQ ID NO: 12)
GACATCGTGCTGACCCAGTCCCCCGACTCCCTGGCCGTGTCCCTGGGC

GAGAGAGCCACCATCAACTGCCGCGCCTCCCAGTCCGTGTCCATCTCC

ACCTACTCCTACATCCACTGGTTCCAGCAGAAGCCCGGCCAGCCCCCC

AAGCTGCTGATCAAGTACGCCTCCAACCTGGAGTCCGGCGTGCCCGAC

CGCTTCTCCGGCTCCGGCTCCGGCACCGACTTCACCCTGAAGATCTCC

CGCGTGGAGGAGGAGGACGTGGGCATCTACTACTGCCAGCACTCCTGG

GAGATCCCCTACACCTTCGGCGGCGGCACCAAGGTGGAGATCAAG

1A8 Vκ3 Light Chain Amino Acid Sequence
(SEQ ID NO: 13)
DIVMTQSPDSLAVSLGERATINCRASQ SVSISTYSYIHWFQQKPGQP

PKLLIKYASNLESGVPDRFSGSGSGTDFTLKISRVEAEDVGIYYCQHS

WEIPYTFGGGTKVEIK

1A8 Vκ3 Light Chain Nucleotide Sequence
(SEQ ID NO: 14)
GACATCGTGATGACCCAGTCCCCCGACTCCCTGGCCGTGTCCCTGGGC

GAGAGAGCCACCATCAACTGCCGCGCCTCCCAGTCCGTGTCCATCTCC

ACCTACTCCTACATCCACTGGTTCCAGCAGAAGCCCGGCCAGCCCCCC

AAGCTGCTGATCAAGTACGCCTCCAACCTGGAGTCCGGCGTGCCCGAC

CGCTTCTCCGGCTCCGGCTCCGGCACCGACTTCACCCTGAAGATCTCC

CGCGTGGAGGCCGAGGACGTGGGCATCTACTACTGCCAGCACTCCTGG

GAGATCCCCTACACCTTCGGCGGCGGCACCAAGGTGGAGATCAAG

Alignments of the six VH amino acid sequences and the three VL amino acid sequences with the counterpart murine 1A8 antibody VH and VL sequences are shown in FIG. 1 and FIG. 2, respectively.

The following antibodies were tested for binding to β6 in binding assays using NIH3T3 cells transfected with β6: VH1/VK1, VH1/VK3, VH2/VK2, VH2/VK3, VH3/VK1, VH3/VK3, VH4/VK1, VH4/VK2, and VH4/VK3. FACS analysis was performed according to Weinreb et al., *J. Biol. Chem.*, 279(17):17875-17887 (2004). The secondary antibody used was mouse anti-human IgG. All of the tested antibodies were found to bind the NIH3T3 cells transfected with β6.

Example 2: Construction of Humanized 1A8 Antibodies

Variant composite human antibody VH (VH1 to 4) and Vκ (Vκ 1 to 3) region genes for anti-integrin αvβ6 were synthesized using a series of overlapping oligonucleotides that were annealed, ligated and PCR amplified to give full length synthetic V regions. The assembled variants were then cloned directly into the pANT expression vector system for IgG1 heavy chain and kappa light chain (FIG. 3). The VH region was cloned using MluI and HindIII sites, and the Vκ region was cloned using BssHII and BamHI restriction sites. All constructs were confirmed by sequencing.

Example 3: Expression and Purification of Antibodies

All combinations of the four primary composite IgG1 VH (VH1-4) and Vκ variants (Vκ1 to Vκ3) (i.e. a total of 12 pairings) were stably transfected into NS0 cells via electroporation. The stable transfections were selected using 200 nM methotrexate (Sigma Cat. No. M8407), methotrexate-resistant colonies for each construct were tested for IgG expression levels using an IgG1 ELISA, and the best expressing lines were selected, expanded and frozen under liquid nitrogen. Successful transfection and stable clone selection was achieved for all 12 composite human antibodies.

Figure 4:
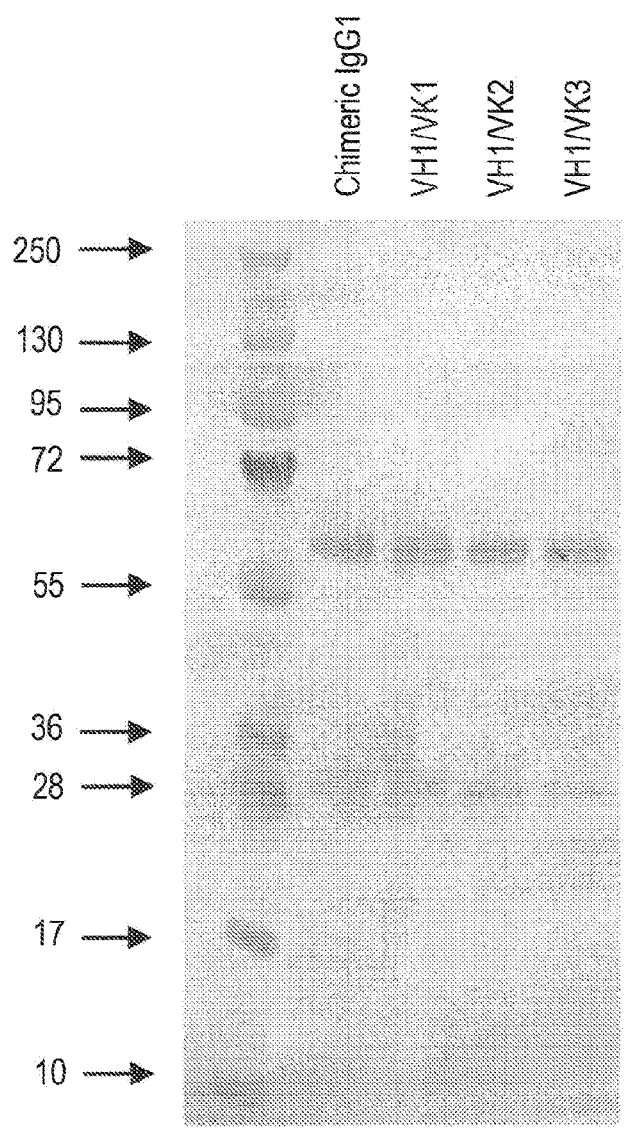
FIG. 4 is a representation of a Coomassie Blue-stained SDS-PAGE gel of selected protein A-purified humanized 1A8 antibodies. 1 μg of each sample was loaded on a NuPage 4-12% Bis-Tris gel (Invitrogen Cat. No. NP0322BOX) and run at 200 V for 35 min. Size marker is prestained protein standard Fermentas PageRuler Plus (Cat. No. SM1811).

Eleven of the composite variants of 1A8 were purified from cell culture supernatants on a Protein A sepharose column (GE Healthcare Cat. No. 110034-93), buffer exchanged into PBS pH 7.4 and quantified by $OD_{280\ nm}$ using an extinction coefficient ($Ec_{(0.1\%)}$=1.45) based on the predicted amino acid sequences. Chimeric antibody and three selected candidate composite variants were analyzed by reducing SDS-PAGE. Bands corresponding to the predicted sizes of the VH and Vκ chains were observed (FIG. 4).

Example 4: Binding of Humanized 1A8 Antibodies to NIH3T3β6 Cells

Figure 5:
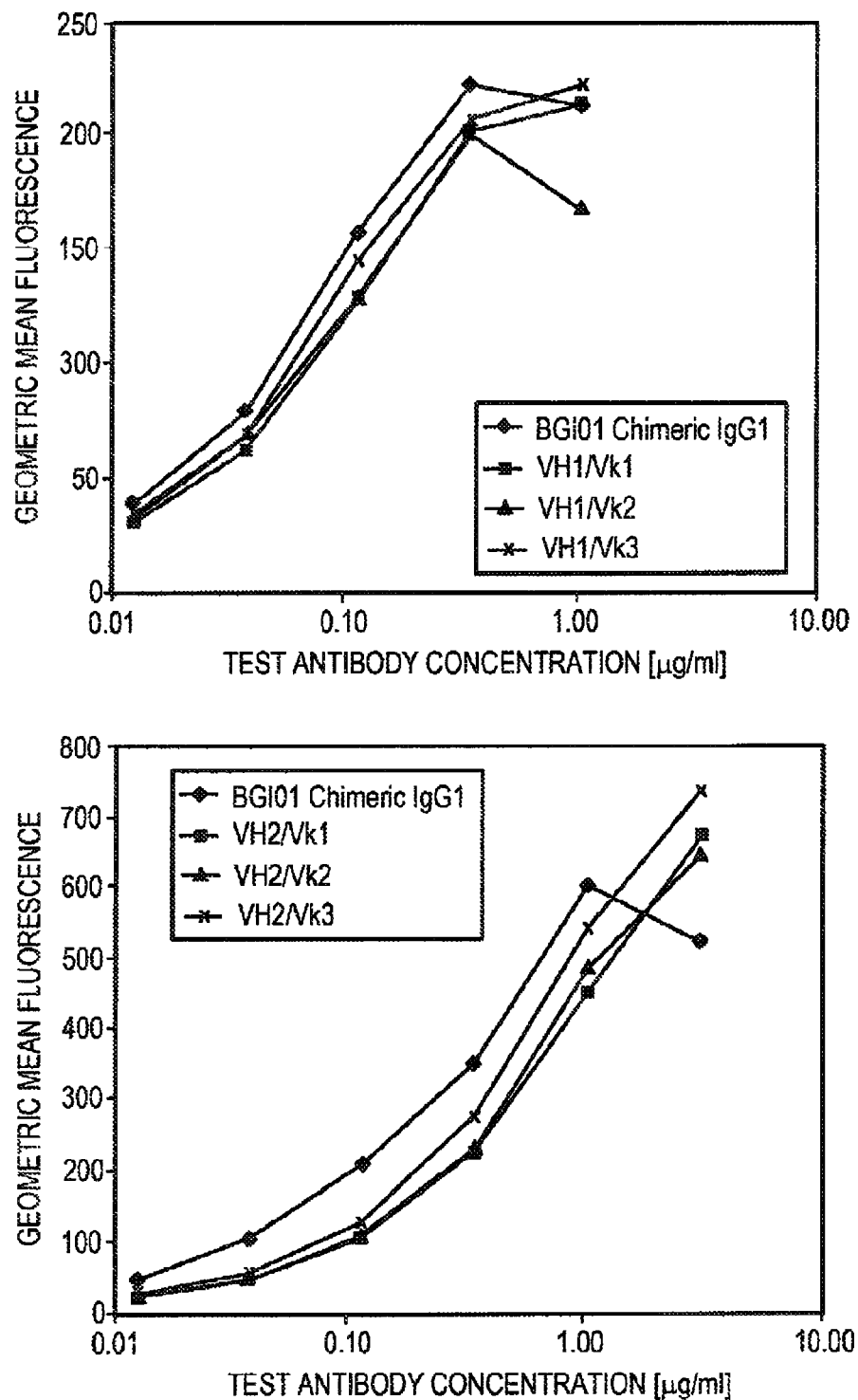
FIG. 5 consists of a series of graphs of FACS binding of chimeric 1A8 (BG101 Chimeric IgG1) and 1A8 Composite Human Antibody variants. A dilution series of antibody was tested for binding to NIH3Tβ6 cells using detection with PE labeled goat anti-human IgG (Sigma Cat. No. P8047).
Figure 5:
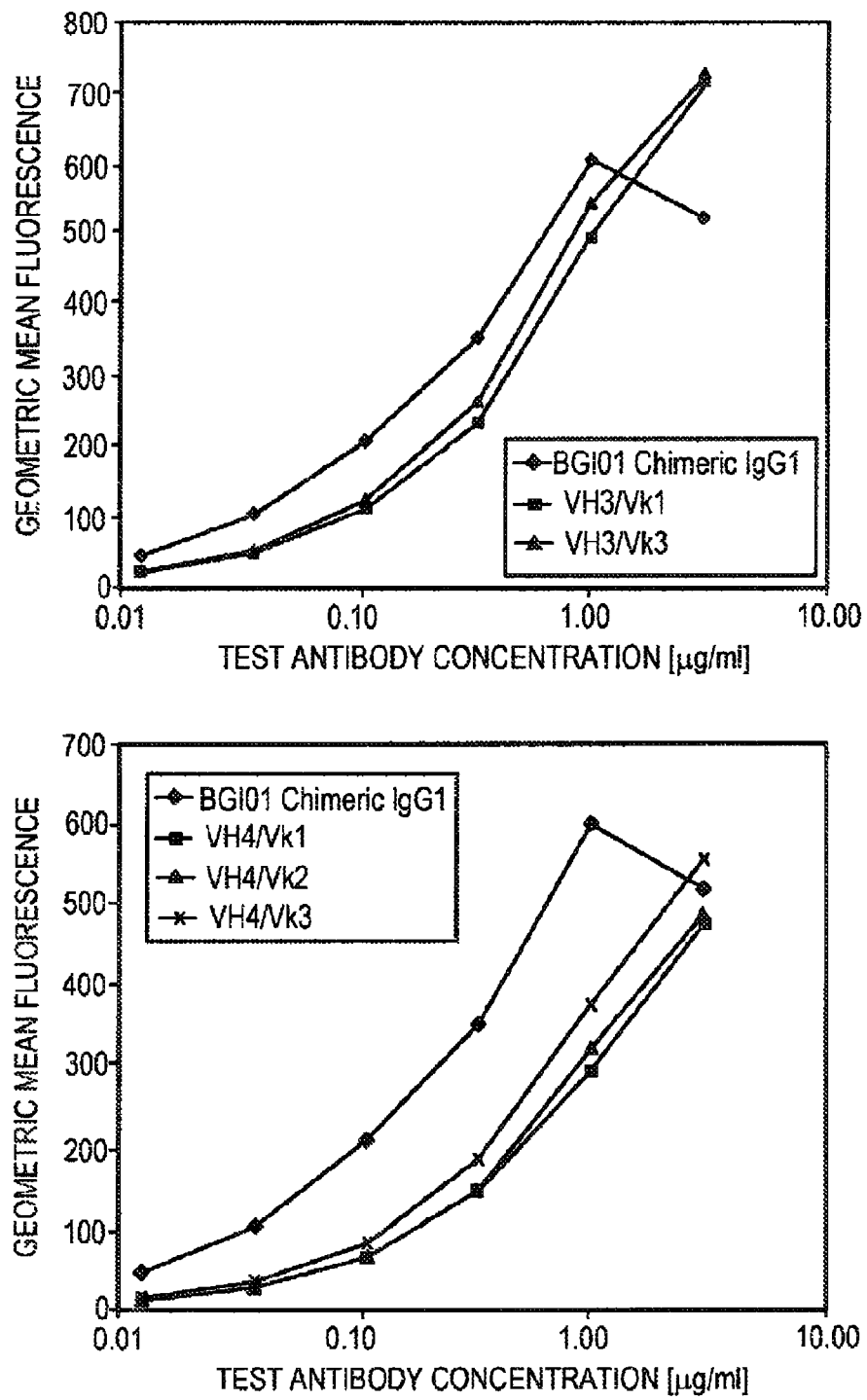

The binding of purified chimeric antibody and each of the composite variants of 1A8 to integrin αvβ6 was assessed by FACS using NIH3T3β6 cells. A dilution series of chimeric (cAb) or humanized antibody was mixed with $3\times10^5$ NIH3T3β6 cells per dilution in FACS buffer. After incubating on ice for 1 hour, cells were washed and incubated with PE labeled goat anti-human IgG (Sigma Cat. No. P8047). After incubating on ice for 45 min, cells were washed, resuspended in 300 μl FACS buffer and analyzed on a Beckton Dickinson FACScalibur. The geometric mean fluorescence intensity was plotted against antibody concentration (FIG. 5). These data were used to calculate EC50 values for each antibody and these values were normalized to the EC50 of chimeric antibody that was included in each FACS assay (Table 1).

TABLE 1

| V Region IDs | EC50 relative to chimeric antibody |
|---|---|
| VH1/Vκ1 | 1.13 |
| VH1/Vκ2 | 1.07 |
| VH1/Vκ3 | 1.04 |
| VH2/Vκ1 | 3.00 |
| VH2/Vκ2 | 2.40 |
| VH2/Vκ3 | 2.46 |
| VH3/Vκ1 | 2.86 |
| VH3/Vκ2 | Not tested |
| VH3/Vκ3 | 2.41 |
| VH4/Vκ1 | 3.57 |
| VH4/Vκ2 | 3.24 |
| VH4/Vκ3 | 2.96 |

All 11 Composite 1A8 humanized antibodies tested showed selective binding to NIH3T3β6 cells and the EC50s for binding were compared to that for the chimeric 1A8, which has the original mouse 1A8 V region sequences (and therefore is expected to have the same binding efficiency as the mouse 1A8 antibody). The relative EC50 data for FACS analysis (Table 1) showed that the 11 composite antibodies bound in the range of relative EC50s of 1.04 to 3.57 with antibodies including the VH1 sequence (VH1/VK1, VH1/VK2 and VH1/VK3) showing superior binding compared with VH2-VH4 containing antibodies.

Example 5: Inhibition of αvβ6 Binding to LAP Using 1A8 Humanized Antibodies

The ability of purified chimeric antibody and each of the composite variants of 1A8 to inhibit αvβ6 binding to LAP was assessed by a solid-phase LAP binding assay (Weinreb et al). A dilution series of chimeric or humanized antibody was mixed with biotinylated αvβ6. After incubating for 1 hour, the mixture was transferred to a LAP coated plate. After 1 hr incubation and washing, the binding of the biotinylated αvβ6 was detected with streptavidin-HRP (Sigma cat. no. 55512) and TMB solution (Invitrogen Cat#002023). The reaction was stopped with 3M HCl, absorbance read at 450 nm on a Dynex Technologies MRX TC II plate reader and the binding curves plotted.

Figure 6:
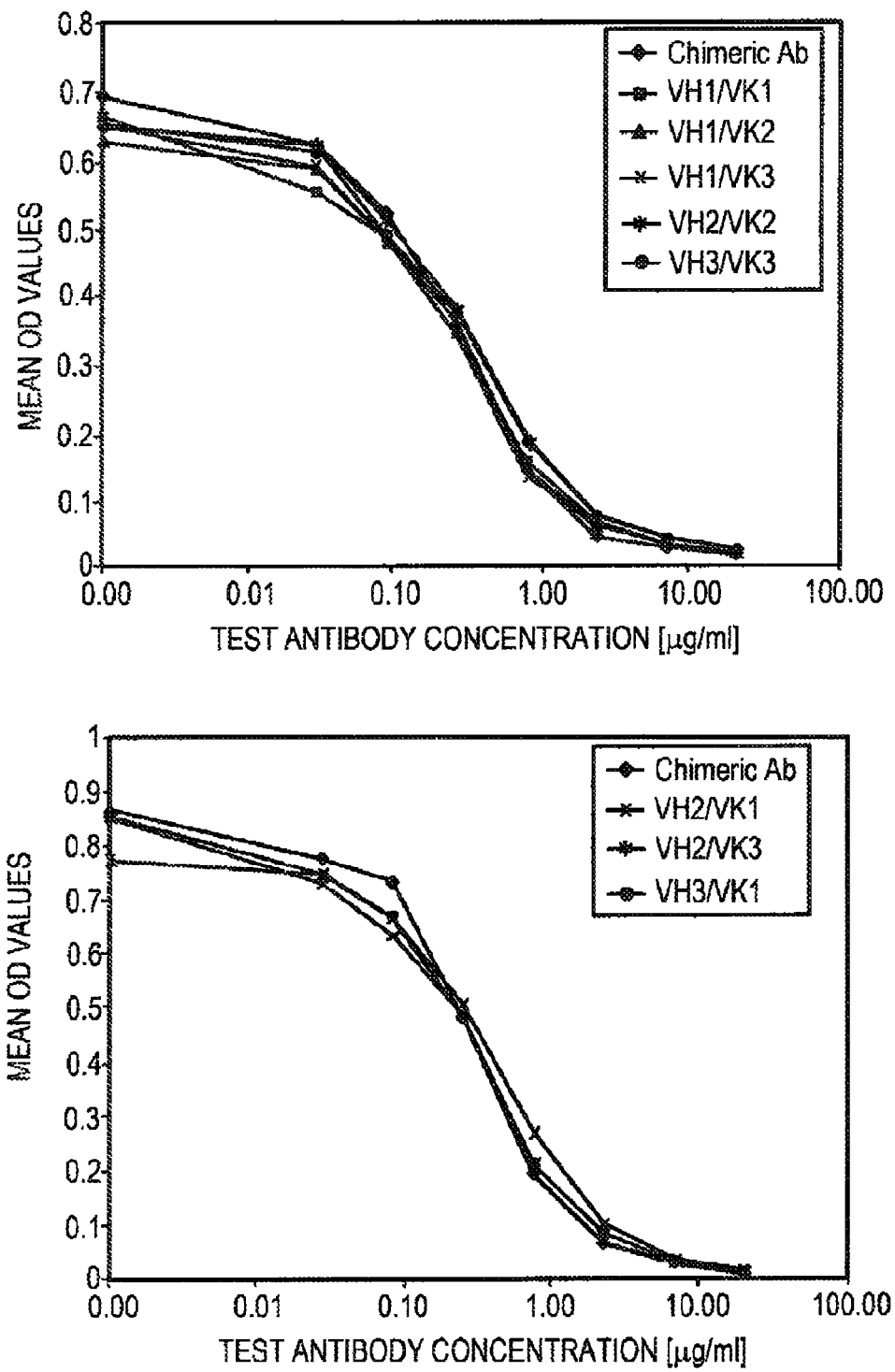
FIG. 6 consists of a series of graphs showing inhibition of αvβ6 binding to LAP using chimeric 1A8 (Chimeric Ab) and 1A8 Composite Human Antibody variants. Binding of biotin labeled αvβ$_6$ to LAP was detected using streptavidin-HRP and TMB solution.
Figure 6:
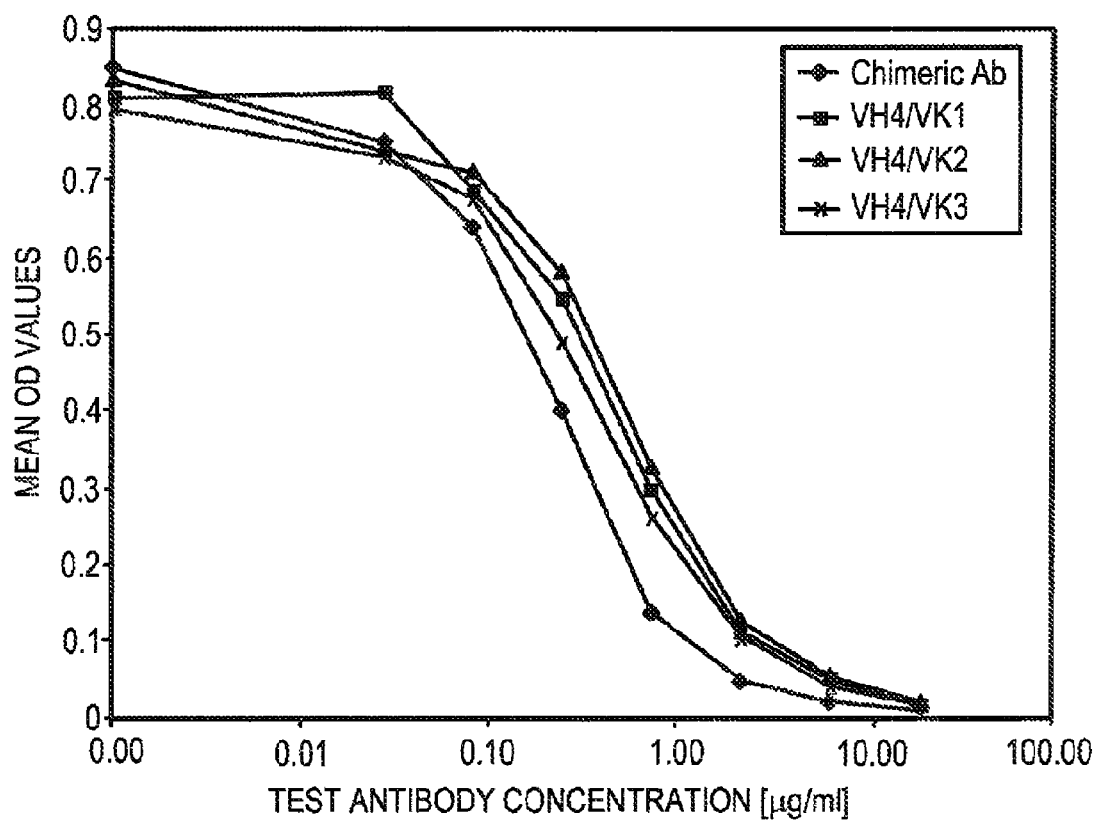
Figure 7A:
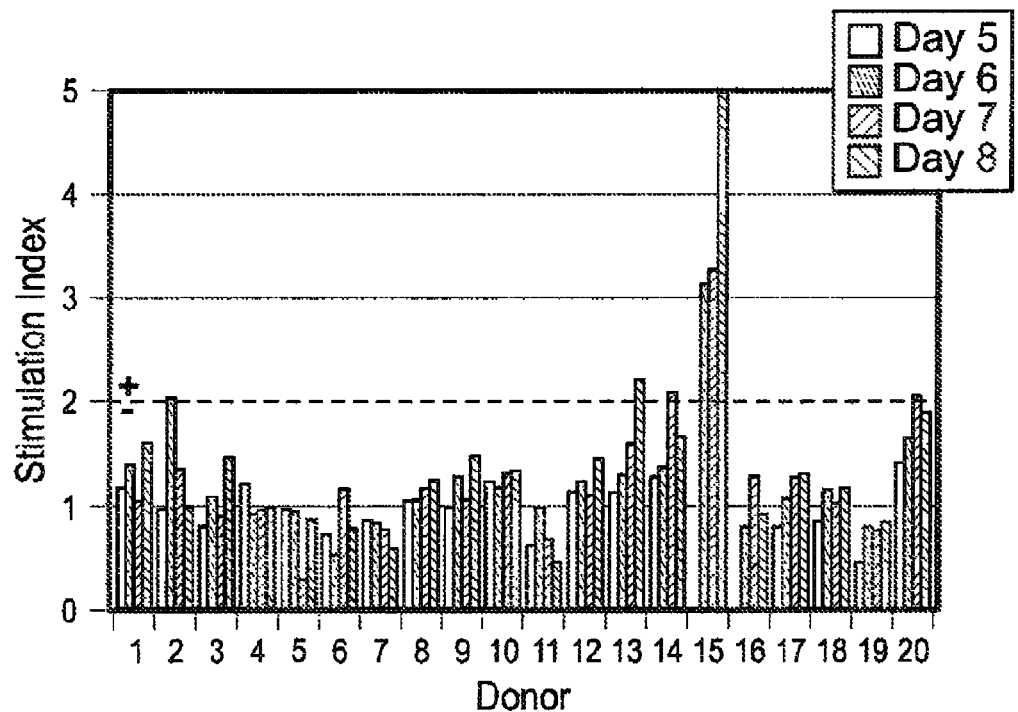
FIG. 7 consists of a series of bar graphs depicting healthy donor T cell proliferation responses to test antibodies. PBMC from bulk cultures were sampled and assessed for proliferation on days 5, 6, 7, and 8 after incubation with the test antibodies: (a) chimeric antibody, (b) VH1/VK1, (c) VH1/VK2, (d) VH1/VK3 and (e) humanized A33. Proliferation responses with an SI≥2.0 (p<0.05), indicated by the dotted line that were significant (p<0.05) using an unpaired, two sample student's t test were considered positive.
Figure 7B:
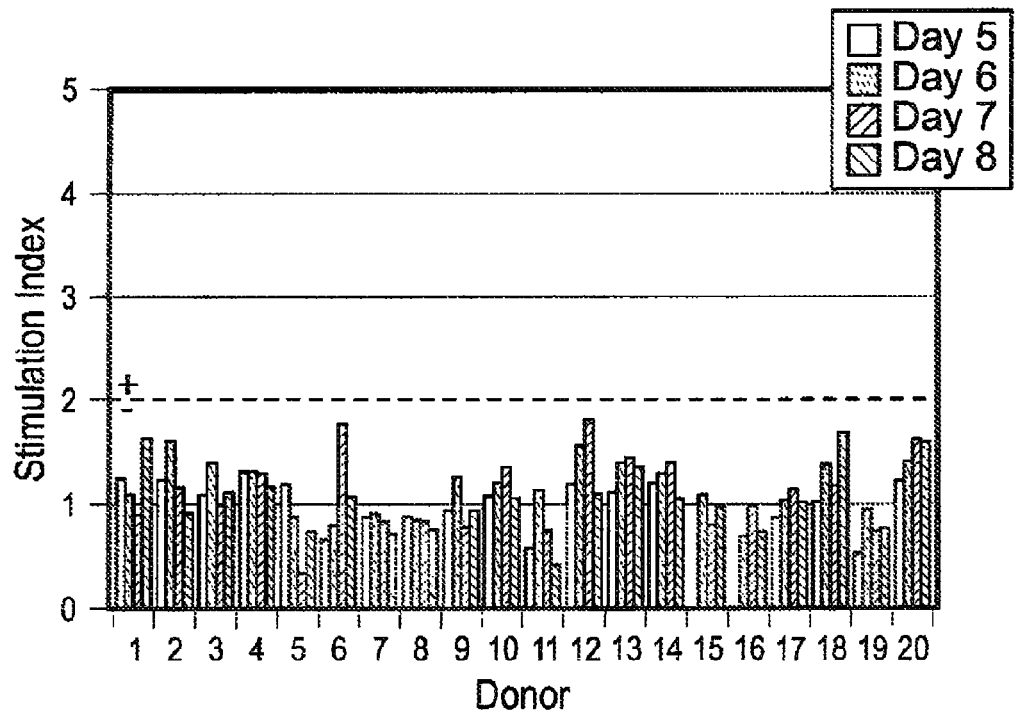
Figure 7C:
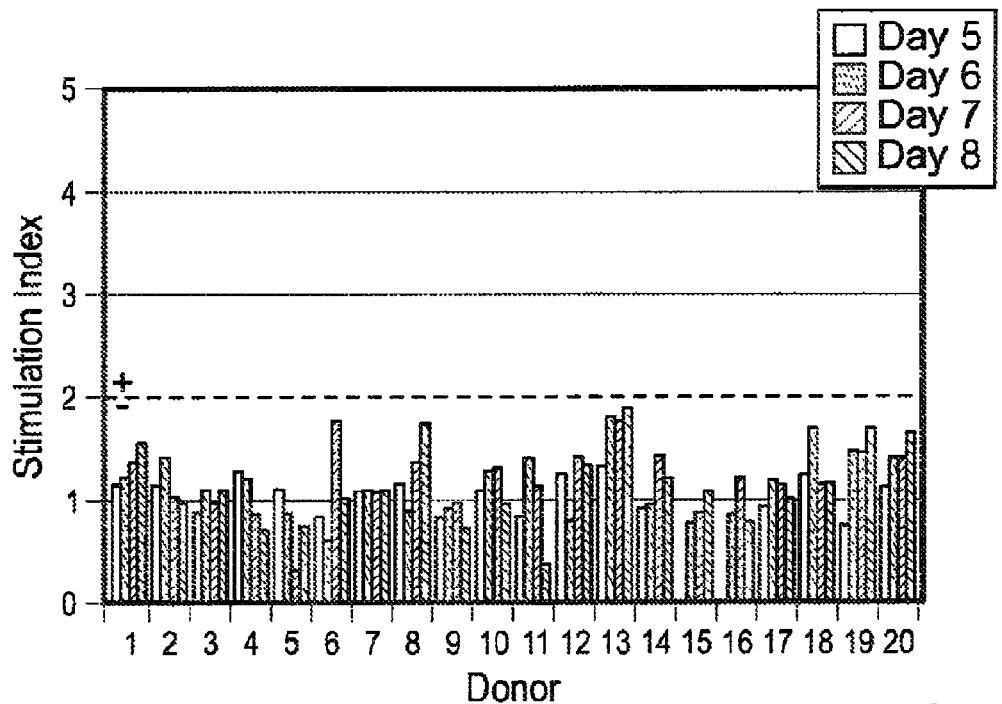
Figure 7D:
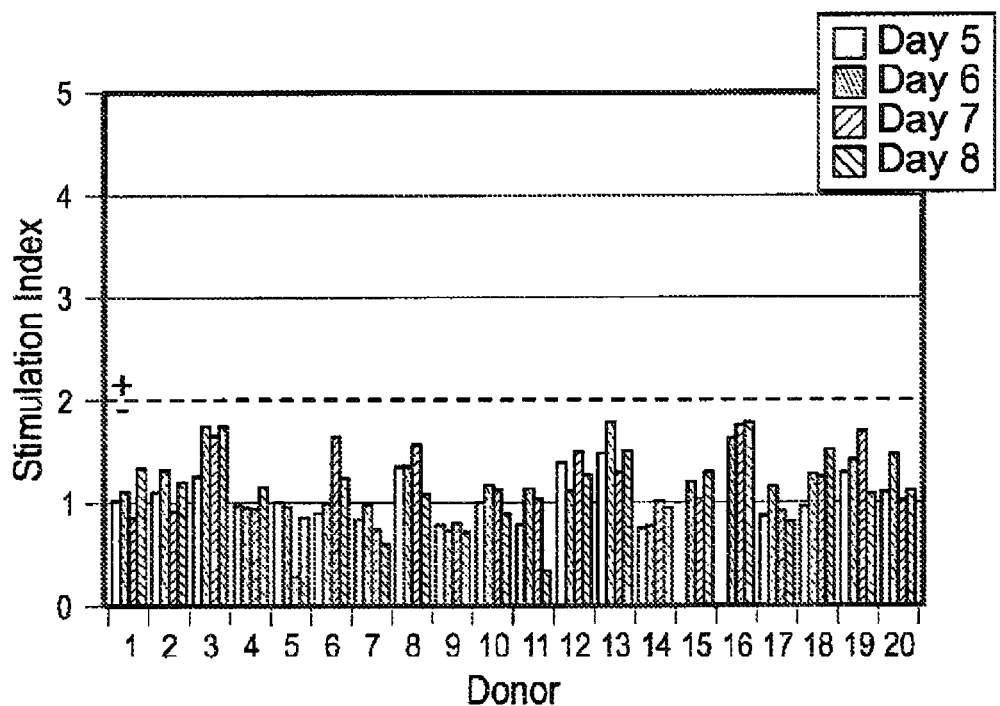
Figure 7E:
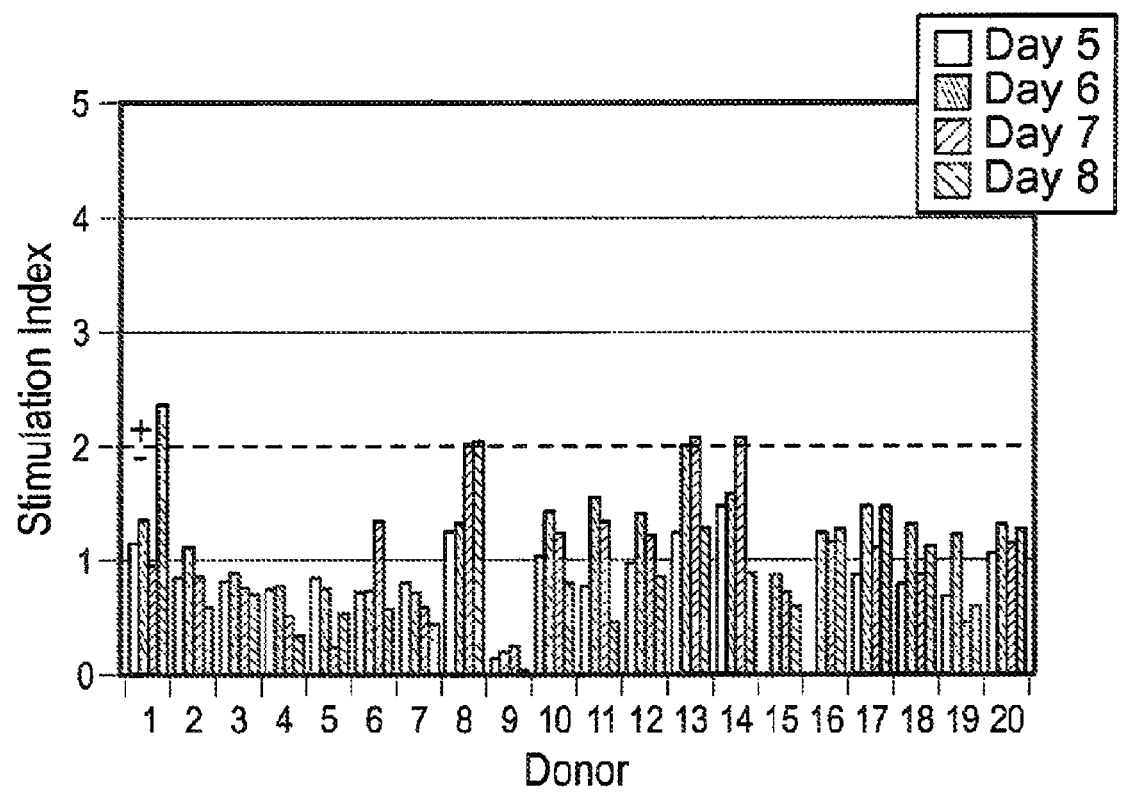

All composite variants of 1A8, other than variants containing VH4, gave similar binding profiles to chimeric 1A8 (FIG. 6). These data were used to calculate IC50 values for each antibody, which were normalized to the IC50 of the chimeric 1A8 antibody included on each plate (Table 2).

TABLE 2

| V Region IDs | IC50 relative to chimeric antibody |
|---|---|
| VH1/Vκ1 | 1.02 |
| VH1/Vκ2 | 1.19 |
| VH1/Vκ3 | 1.05 |
| VH2/Vκ1 | 1.48 |
| VH2/Vκ2 | 1.32 |
| VH2/Vκ3 | 0.98 |
| VH3/Vκ1 | 1.07 |
| VH3/Vκ2 | Not tested |
| VH3/Vκ3 | 1.2 |
| VH4/Vκ1 | 1.93 |
| VH4/Vκ2 | 2.30 |
| VH4/Vκ3 | 1.74 |

For inhibition of αvβ6 binding to LAP, the range of the IC50s for the 1A8 composite antibodies was from 0.98 to 2.30 (Table 2). Antibodies including the VH1 sequence (VH1/VK1, VH1/VK2 and VH1/VK3) showed similar inhibition to chimeric 1A8.

Example 6: EpiScreen™ Time Course Assay of Humanized 1A8 Antibodies

The objective of this study was to assess the immunogenic potential of humanized anti-αvβ6 1A8 antibodies (VH1/VK1, VH1/VK2, VH1/VK3) compared to the reference chimeric 1A8 antibody by measuring ex vivo T cell responses against the whole antibodies (compared to the chimeric antibody) using the EpiScreen™ time course T cell assay.

INTRODUCTION

Immune responses to biological therapeutic agents are wide ranging, and can be directed against agents that are both non-human and human in origin. These responses include those that elicit a weak clinical effect and those that limit efficacy which can occasionally result in morbidity or even mortality in patients. In particular, serious complications can arise with the production of neutralizing antibodies, especially when they target recombinant self-proteins and therefore have the potential to cross react with the patient's own endogenous protein (Lim, *Hematology*, 10(3): 255-9 (2005)). Problems associated with immunogenicity to biologics, especially monoclonal antibodies, have been reduced largely due to advances in molecular biology. There are, however, many recombinant protein biologics that are identical to endogenously expressed human sequences that still elicit potent neutralizing immune responses in patients (Hochuli, *J Interferon Cytokine Res.*, 17 Suppl 1:S15-21 (1997); Schellekens et al., *J Interferon Cytokine Res.*, 17 (Suppl. 1), S5-S8 (1997); Namaka et al., *Curr Med Res Opin.*, 22(2):223-39 (2006)). The mechanism by which immunogenicity is triggered remains unclear although the tolerance to self-proteins may be broken by a number of factors linked to both the product and the patient (reviewed in Chester et al., *Expert Rev Clin Immunol.*, 1(4): 549-559 (2005); Baker and Jones, *Curr Opin Drug Discov Devel.*, 10(2):219-27 (2007)). For the product, these include dose, frequency and route of administration, immunomodulatory capacity of the protein therapeutic, and the formulation (Jaber and Baker, *J Pharm Biomed Anal.*, 43(4):1256-61 (2007)). For the patient, factors such as immune competence, MHC haplotype and intrinsic tolerance to the protein therapeutic will influence immunogenicity. Regardless of how immunogenicity is triggered, one of the single most important factors in the development of an ensuing immune response is the presence of epitopes that are able to effectively stimulate a potent $CD4^+$ T cell response.

The value of T cell epitope analysis is becoming increasingly important particularly in the pre-clinical analysis of biologics. A pre-clinical ex vivo T cell assay (EpiScreen™) provides an effective technology for predicting T cell immunogenicity by quantifying T cell responses to protein therapeutics. EpiScreen™ time course T cell assays provide a format in which the immunogenicity of whole proteins can be assessed. Using a cohort of community blood donors carefully selected based on MHC haplotypes, purified therapeutic proteins are tested for T cell immunogenicity in vitro. This technology has been used successfully to compare protein variants for the potential to induce an immune response in vivo (Jones et al., *J Interferon Cytokine Res.*, 24(9):560-72 (2004); Jones et al., *J Thromb Haemost.*, 3(5):991-1000 (2005)). These studies show that EpiScreen™ provides a powerful screening technology due to the high degree of sensitivity along with the robust nature of the assay which allows an accurate pre-clinical assessment of the potential for immunogenicity of biologics.

In the study discussed below, fully-humanized anti-1A8 antibodies (VH1/VK1, VH1/VK2, VH1/VK3) and the reference chimeric antibody were assessed for immunogenic potential using EpiScreen™ time course T cell assays where bulk cultures were established using $CD8^+$ depleted PBMC, and T cell proliferation was measured by incorporation of [$^3$H]-Thymidine at various time points after the addition of the antibodies.

Methods

Preparation and Selection of Donor PBMC

PBMC were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMC were isolated from buffy coats by Lymphoprep (Axis-shield, Dundee, UK) density centrifugation and $CD8^+$ T cells were depleted using $CD8^+$ RosetteSep™ (StemCell Technologies Inc., London, UK). Donors were characterized by identifying HLA-DR haplotypes using an HLA SSP-PCR based tissue-typing kit (Biotest, Solihull, UK). T cell responses to a 'reproducibility' control antigen (KLH, Pierce (Perbio), Cramlington, UK) were also determined. PBMC were then frozen and stored in liquid nitrogen until required. A cohort of 20 donors was selected (study cohort BGI01) to best represent the number and frequency of HLA-DR allotypes expressed in the world population.

Purification of Antibodies

The chimeric and fully humanized antibodies were prepared from up to 2 L cultures of NS0 cell lines expressing the antibodies. Supernatants were separated from cells and debris by centrifugation, adjusted to pH 7.4 and 150 mM NaCl with 1/9 volumes 10×PBS (Invitrogen, Paisley, UK) and filter sterilized. Supernatants were then run through 1 ml Hi-Trap Mab Select Sure protein A affinity columns (GE Healthcare, Amersham, UK), which had previously been sanitized with 0.5 M NaOH and equilibrated into PBS, at a flow rate of 1 ml/min. The columns were washed with 50 ml PBS pH 7.4, and antibody was eluted in 1 ml fractions with 0.1 M sodium citrate pH 3.0 followed by immediate neutralization with 0.1 ml 1 M Tris pH 9.0. The protein content of each fraction was monitored by UV absorption at 280 nm and protein containing fractions were pooled and immediately buffer exchanged into 1×PBS pH 7.4 (PAA Laboratories, Yeovil, UK) using PD10 desalting columns (GE Healthcare). The antibodies were further purified by size exclusion chromatography using a 16/60 Superdex 5200 column (GE Healthcare) in 1×PBS. The major peak fractions were collected, pooled, filter sterilized and stored at +4° C. Final concentrations were determined by UV absorption using calculated molar extinction coefficients where $A_{280}$ 1.0=1.45 mg/ml.

Endotoxin levels were analyzed using an Endosafe®-PTS™ (Charles River, Margate, UK) and found to be within the tolerances of the EpiScreen assay (<5.0 EU/mg).

EpiScreen™ Time Course T Cell Proliferation Assays

PBMC from each donor were thawed, counted and viability assessed. Cells were revived in room temperature AIM-V® culture medium (Invitrogen, Paisley, UK), washed and resuspended in AIM-V® to $4-6\times10^6$ PBMC/ml. For each donor, bulk cultures were established in which 1 ml proliferation cell stock was added to the appropriate wells of a 24 well plate. 0.5 ml of culture medium and 0.5 ml of each diluted test sample were added to the PBMC to give a final antibody concentration of 50 µg/ml per sample. For each donor, a reproducibility control (cells incubated with 100 µg/ml KLH) and a culture medium-only control were also included. Cultures were incubated for a total of 8 days at 37° C. with κ% $CO_2$. On days 5, 6, 7, and 8, the cells in each well were gently resuspended and 3×100 µl aliquots transferred to each well of a round bottomed 96 well plate. The cultures were pulsed with 0.75 µCi [3H]-Thymidine (Perkin Elmer®, Beaconsfield, UK) in 100 µl AIM-V® culture medium and incubated for a further 18 hours before harvesting onto filter mats (Perkin Elmer®) using a TomTec Mach III cell harvester. Counts per minute (cpm) for each well were determined by Meltilex™ (Perkin Elmer®) scintillation counting on a 1450 Microbeta Wallac Trilux Liquid Scintillation Counter (Perkin Elmer®) in paralux, low background counting.

EpiScreen™ Data Analysis

For proliferation assays, an empirical threshold of a stimulation index (SI) equal to or greater than 2 (SI≥2.0) has been previously established whereby samples inducing proliferative responses above this threshold are deemed positive (where included, borderline SIs≥1.90 are highlighted). Extensive assay development and previous studies have shown that this is the minimum signal-to-noise threshold allowing maximum sensitivity without detecting large numbers of false positive responses. For proliferation data sets (n=3), positive responses were defined by statistical and empirical thresholds:
1. Significance (p<0.05) of the response by comparing cpm of test wells against medium control wells using unpaired two sample student's t-test.
2. SI equal to or greater than 2 (SI≥2.0).

In addition, intra-assay variation was assessed by calculating the CVs and SDs of the raw data from replicate cultures.

Results

The fully humanized and chimeric 1A8 antibodies were tested against a cohort of 20 healthy donors using EpiScreen™ time course T cell assay in order to determine the relative risk of immunogenicity. The samples were tested at a final concentration of 50 μg/ml based on previous studies showing that this is a saturating concentration for stimulation of antibody-specific T cell responses. In order to assess the immunogenic potential of each antibody, the EpiScreen™ time course T cell assay was used with analysis of proliferation to measure T cell activation.

Table 3 provides a summary of the results obtained in the EpiScreen™ time course T cell proliferation assay of CD4+ T cell responses induced by the test antibodies. Positive T cell responses (stimulation index (SI)≥2.00, significant p<0.05) ("P") for proliferation during the entire time course days 5-8 are shown. The frequencies of positive T cell responses for proliferation are shown as a percentage at the bottom of the columns. No day 5 data was obtained from donors 19 and 20.

TABLE 3

|  | BGI01 Chimera | VH1/VK1 | VH1/VK2 | VH1/VK3 | A33 | KLH |
|---|---|---|---|---|---|---|
| Donor 1 |  |  |  |  | P | P |
| Donor 2 | P |  |  |  |  | P |
| Donor 3 |  |  |  |  |  | P |
| Donor 4 |  |  |  |  |  | P |
| Donor 5 |  |  |  |  |  | P |
| Donor 6 |  |  |  |  |  |  |
| Donor 7 |  |  |  |  |  | P |
| Donor 8 |  |  |  |  | P | P |
| Donor 9 |  |  |  |  |  |  |
| Donor 10 |  |  |  |  |  | P |
| Donor 11 |  |  |  |  |  | P |
| Donor 12 |  |  |  |  |  | P |
| Donor 13 | P |  |  |  | P | P |
| Donor 14 | P |  |  |  | P | P |
| Donor 15 | P |  |  |  |  | P |
| Donor 16 |  |  |  |  |  | P |
| Donor 17 |  |  |  |  |  | P |
| Donor 18 |  |  |  |  |  | P |
| Donor 19 |  |  |  |  |  | P |
| Donor 20 | P |  |  |  |  | P |
| Proliferation % | 25 | 0 | 0 | 0 | 20 | 90 |

FIG. 7 illustrates the donor SI responses to each of the test antibodies throughout the time course. None of the fully humanized 1A8 antibodies (VH1/VK1, VH1/VK2, VH1/VK2) induced positive responses using a SI≥2.0, p<0.05 threshold, whereas the chimeric 1A8 antibody induced positive T cell proliferation responses in 25% of donors.

CONCLUSIONS

The EpiScreen™ time course T cell proliferation assay was used to determine the potential for clinical immunogenicity of the fully humanized 1A8 antibodies (VH1/VK1, VH1/VK2, VH1/VK2). The fully humanized and chimeric 1A8 antibodies were tested for their ability to induce CD4+ T cell responses as measured by proliferation against a panel of 20 HLA-typed donors. Frequent and potent positive CD4+ T cell proliferation responses were observed in the EpiScreen™ time course T cell assay against the reproducibility control antigen KLH and the clinical control (humanized A33) induced a response rate of 20%, which was in the normal range seen in previous EpiScreen™ studies (20% to 30%). T cell proliferation responses were observed with the chimeric 1A8 antibody (25% response rate), thus showing that the chimeric antibody has a significant immunogenic potential. No positive T cell proliferation responses were seen to the fully humanized 1A8 antibodies indicating that they have a very low potential for immunogenicity.

Figure 8:
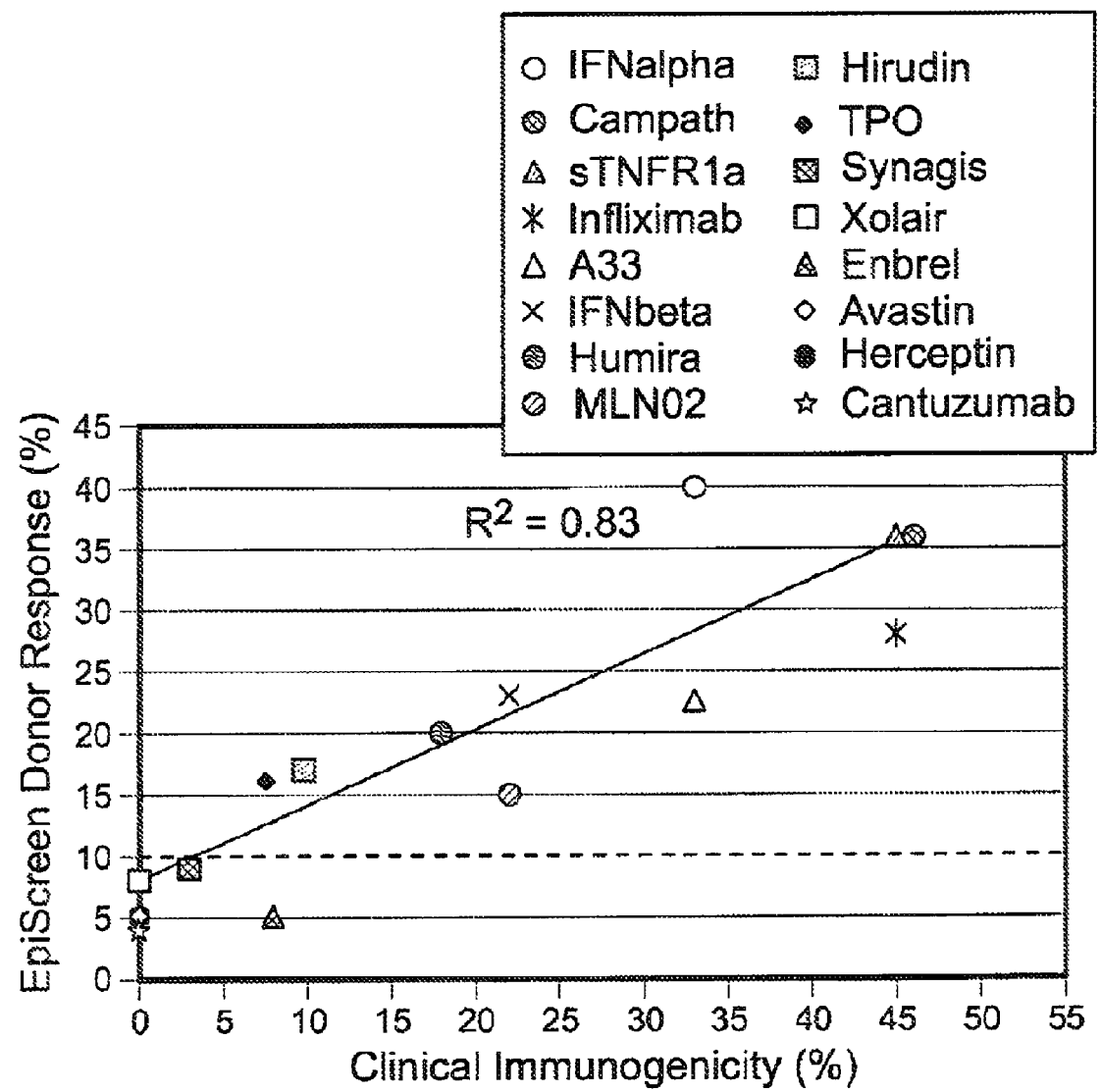
FIG. 8 is a graph comparing the immunogenicity predicted using EpiScreen™ analysis and immunogenicity observed in a clinical setting. Sixteen therapeutic proteins were tested for frequency of CD4$^+$ T cell responses using EpiScreen™ technology. Results were plotted against the frequency of immunogenicity (anti-therapeutic antibody responses) observed for each protein when used in the clinic (data sourced from PubMed). The line of regression and the correlation coefficient is shown.

Previous EpiScreen™ time course T cell assays with a range of biologics (FIG. 8) have shown a clear correlation between the percentage of donor T cell responses in the EpiScreen™ assay and the level of immunogenicity (anti-protein therapeutic antibody responses) observed in the clinic. High frequency donor responses were observed in EpiScreen™ assays for immunogenic antibodies such as Campath, whereas relatively low frequency donor responses were observed for non-immunogenic antibodies such as Xolair and Herceptin. In general, protein therapeutics that induce <10% positive responses in the EpiScreen™ assay are associated with a low risk of immunogenicity in the clinic. The current study shows that, in comparison to other protein therapeutics tested in EpiScreen™ assays (FIG. 8), each of the fully humanized 1A8 antibodies fall into the same range as Xolair, Herceptin, and Avastin, and would be considered as having a low risk of immunogenicity. In comparison, the chimeric 1A8 antibody stimulated 25% of donors to respond in the EpiScreen™ assay and would therefore fall into the same range as immunogenic antibodies such as Humira. In sum, the fully humanized 1A8 antibodies exhibit a clinically acceptable immunogenicity profile from the EpiScreen™ assay providing confirmation of reduced immunogenicity as a result of the humanization.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that specifically binds to αvβ6, wherein the antibody or the antigen-binding fragment thereof comprises:
   a heavy chain variable region that comprises the amino acid sequence set forth in SEQ ID NO:1 and a light chain variable region that comprises the amino acid sequence set forth in SEQ ID NO:9;
   a heavy chain variable region that comprises the amino acid sequence set forth in SEQ ID NO:3 and a light chain variable region that comprises the amino acid sequence set forth in SEQ ID NO:9;
   a heavy chain variable region that comprises the amino acid sequence set forth in SEQ ID NO:5 and a light chain variable region that comprises the amino acid sequence set forth in SEQ ID NO:9;
   a heavy chain variable region that comprises the amino acid sequence set forth in SEQ ID NO:7 and a light chain variable region that comprises the amino acid sequence set forth in SEQ ID NO:9;

a heavy chain variable region that comprises the amino acid sequence set forth in SEQ ID NO:50 and a light chain variable region that comprises the amino acid sequence set forth in SEQ ID NO:9; or a heavy chain variable region that comprises the amino acid sequence set forth in SEQ ID NO:52 and a light chain variable region that comprises the amino acid sequence set forth in SEQ ID NO:9.

2. An antibody or antigen-binding fragment thereof that specifically binds to αvβ6, wherein the antibody or the antigen-binding fragment thereof comprises:

a heavy chain variable region that comprises the amino acid sequence set forth in SEQ ID NO:1 and a light chain variable region that comprises the amino acid sequence set forth in SEQ ID NO:11;

a heavy chain variable region that comprises the amino acid sequence set forth in SEQ ID NO:3 and a light chain variable region that comprises the amino acid sequence set forth in SEQ ID NO:11;

a heavy chain variable region that comprises the amino acid sequence set forth in SEQ ID NO:5 and a light chain variable region that comprises the amino acid sequence set forth in SEQ ID NO:11;

a heavy chain variable region that comprises the amino acid sequence set forth in SEQ ID NO:7 and a light chain variable region that comprises the amino acid sequence set forth in SEQ ID NO:11;

a heavy chain variable region that comprises the amino acid sequence set forth in SEQ ID NO:50 and a light chain variable region that comprises the amino acid sequence set forth in SEQ ID NO:11; or a heavy chain variable region that comprises the amino acid sequence set forth in SEQ ID NO:52 and a light chain variable region that comprises the amino acid sequence set forth in SEQ ID NO:11.

3. An antibody or antigen-binding fragment thereof that specifically binds to αvβ6, wherein the antibody or the antigen-binding fragment thereof comprises:

a heavy chain variable region that comprises the amino acid sequence set forth in SEQ ID NO:1 and a light chain variable region that comprises the amino acid sequence set forth in SEQ ID NO:13;

a heavy chain variable region that comprises the amino acid sequence set forth in SEQ ID NO:3 and a light chain variable region that comprises the amino acid sequence set forth in SEQ ID NO:13;

a heavy chain variable region that comprises the amino acid sequence set forth in SEQ ID NO:5 and a light chain variable region that comprises the amino acid sequence set forth in SEQ ID NO:13;

a heavy chain variable region that comprises the amino acid sequence set forth in SEQ ID NO:7 and a light chain variable region that comprises the amino acid sequence set forth in SEQ ID NO:13;

a heavy chain variable region that comprises the amino acid sequence set forth in SEQ ID NO:50 and a light chain variable region that comprises the amino acid sequence set forth in SEQ ID NO:13; or a heavy chain variable region that comprises the amino acid sequence set forth in SEQ ID NO:52 and a light chain variable region that comprises the amino acid sequence set forth in SEQ ID NO:13.

4. A pharmaceutical composition comprising the antibody or the antigen-binding fragment thereof of claim 1 and a pharmaceutically acceptable carrier.

5. A pharmaceutical composition comprising the antibody or the antigen-binding fragment thereof of claim 2 and a pharmaceutically acceptable carrier.

6. A pharmaceutical composition comprising the antibody or the antigen-binding fragment thereof of claim 3 and a pharmaceutically acceptable carrier.

7. A method of treating a cancer in a human subject in need thereof, comprising administering to the human subject the antibody or the antigen-binding fragment thereof of claim 1.

8. The method of claim 7, wherein the cancer is a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, and an endometrial cancer.

9. A method of treating fibrosis in a human subject in need thereof, comprising administering to the human subject the antibody or the antigen-binding fragment thereof of claim 1.

10. A method of treating acute exacerbations of idiopathic pulmonary fibrosis in a human subject in need thereof, comprising administering to the human subject the antibody or the antigen-binding fragment thereof of claim 1.

11. A method of diagnosing an αvβ6-mediated disorder in a human subject, the method comprising:
(a) contacting a cell or tissue from the human subject with an isolated antibody or an antigen-binding fragment thereof of claim 1;
(b) detecting the formation of a complex between the antibody or the antigen-binding fragment thereof and the cell or tissue to determine the level of expression of αvβ6 in the cell or tissue,
wherein an increased level of αvβ6 in the cell or tissue compared to a cell or tissue from a control human subject not having the αvβ6-mediated disorder is indicative that the human subject has, or is likely to develop, the αvβ6-mediated disorder.

12. A method of treating a cancer in a human subject in need thereof, comprising administering to the human subject the antibody or the antigen-binding fragment thereof of claim 2.

13. A method of treating a cancer in a human subject in need thereof, comprising administering to the human subject the antibody or the antigen-binding fragment thereof of claim 3.

14. The method of claim 12, wherein the cancer is a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, and an endometrial cancer.

15. The method of claim 13, wherein the cancer is a pancreatic cancer, a lung cancer, a breast cancer, a colorectal cancer, a head and neck cancer, an esophageal cancer, a skin cancer, a cervical cancer, a prostate cancer, an ovarian cancer, a kidney cancer, and an endometrial cancer.

16. A method of treating fibrosis in a human subject in need thereof, comprising administering to the human subject the antibody or the antigen-binding fragment thereof of claim 2.

17. A method of treating fibrosis in a human subject in need thereof, comprising administering to the human subject the antibody or the antigen-binding fragment thereof of claim 3.

18. A method of treating acute exacerbations of idiopathic pulmonary fibrosis in a human subject in need thereof, comprising administering to the human subject the antibody or the antigen-binding fragment thereof of claim 2.

19. A method of treating acute exacerbations of idiopathic pulmonary fibrosis in a human subject in need thereof, comprising administering to the human subject the antibody or the antigen-binding fragment thereof of claim 3.

20. A method of diagnosing an αvβ6-mediated disorder in a human subject, the method comprising:
   (a) contacting a cell or tissue from the human subject with an isolated antibody or an antigen-binding fragment thereof of claim 2;
   (b) detecting the formation of a complex between the antibody or the antigen-binding fragment thereof and the cell or tissue to determine the level of expression of αvβ6 in the cell or tissue,
   wherein an increased level of αvβ6 in the cell or tissue compared to a cell or tissue from a control human subject not having the αvβ6-mediated disorder is indicative that the human subject has, or is likely to develop, the αvβ6-mediated disorder.

21. A method of diagnosing an αvβ6-mediated disorder in a human subject, the method comprising:
   (a) contacting a cell or tissue from the human subject with an isolated antibody or an antigen-binding fragment thereof of claim 3;
   (b) detecting the formation of a complex between the antibody or the antigen-binding fragment thereof and the cell or tissue to determine the level of expression of αvβ6 in the cell or tissue,
   wherein an increased level of αvβ6 in the cell or tissue compared to a cell or tissue from a control human subject not having the αvβ6-mediated disorder is indicative that the human subject has, or is likely to develop, the αvβ6-mediated disorder.

* * * * *

SEQUENCE LISTING

<160> NUMBER OF SEQ ID NOS: 68

<210> SEQ ID NO 1
<211> LENGTH: 126
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 1
```

Gln Val Gln Phe Val Gln Ser Gly Pro Glu Leu Lys Lys Pro Gly Ala
1               5                   10                  15

Ser Val Lys Val Ser Cys Lys Gly Ser Ser Tyr Thr Phe Thr Asp Tyr
            20                  25                  30

Thr Met His Trp Val Lys Leu Ala His Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Gly Arg Ala Thr Met Thr Val Asp Lys Ser Ser Thr Ala Tyr
65                  70                  75                  80

Met Glu Leu Ala Arg Leu Arg Ser Glu Asp Ser Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Ser Val Thr Val Ser Ser
        115                 120                 125

```
<210> SEQ ID NO 2
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
caggtgcagt tcgtgcagtc cggcccccgag ctgaagaagc ccggcgcctc cgtgaaggtg    60
tcctgcaagg gctcctccta caccttcacc gactacacca tgcactgggt gaagctggcc   120
cacgccaaga ccctggagtg gatcggcgtg atcgacacct actacggcaa gaccaactac   180
aaccagaagt tcgagggccg cgccaccatg accgtggaca gtcctcctc accgcctac    240
atggagctgg cccgcctgcg ctccgaggac tccgccgtgt actactgcgc ccgcggcggc   300
ttccgccgcg gcgaccgccc ctccctgcgc tacgccatgg actcctgggg ccagggcacc   360
tccgtgaccg tgtcctcc                                                 378

<210> SEQ ID NO 3
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

Gln Val Gln Leu Val Gln Ser Gly Ala Glu Val Lys Lys Pro Gly Ala
1               5                   10                  15

Ser Val Lys Val Ser Cys Lys Gly Ser Ser Tyr Thr Phe Thr Asp Tyr
            20                  25                  30

Thr Met His Trp Val Lys Leu Ala Ser Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Gly Arg Ala Thr Met Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Leu Val Thr Val Ser Ser
            115                 120                 125

<210> SEQ ID NO 4
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
caggtgcagc tggtgcagtc cggcgccgag gtgaagaagc ccggcgcctc cgtgaaggtg      60
tcctgcaagg gctcctccta caccttcacc gactacacca tgcactgggt gaagctggcc     120
tccgccaaga ccctggagtg gatcggcgtg atcgacacct actacggcaa gaccaactac     180
aaccagaagt tcgagggccg cgccaccatg accgtggaca gtcctcctc caccgcctac      240 atggagctgt cctccctgcg ctccgaggac accgccgtgt actactgcgc ccgcggcggc     300
ttccgccgcg gcgaccgccc ctccctgcgc tacgccatgg actcctgggg ccagggcacc     360
ctggtgaccg tgtcctcc                                                   378

<210> SEQ ID NO 5
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Gly Ser Ser Tyr Thr Phe Thr Asp Tyr
            20                  25                  30

Thr Met His Trp Val Arg Leu Ala Ser Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Gly Arg Ala Thr Met Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Leu Val Thr Val Ser Ser
            115                 120                 125

```
<210> SEQ ID NO 6
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
caggtgcagc tggtgcagtc cggcgccgag gtgaagaagc ccggcgcctc cgtgaaggtg     60
tcctgcaagg gctcctccta caccttcacc gactacacca tgcactgggt gcgcctggcc    120
tccgccaaga ccctggagtg gatcggcgtg atcgacacct actacggcaa gaccaactac    180
aaccagaagt tcgagggccg cgccaccatg accgtggaca gtcctcctc accgcctac     240 atggagctgt cctccctgcg ctccgaggac accgccgtgt actactgcgc ccgcggcggc    300
ttccgccgcg gcgaccgccc ctccctgcgc tacgccatgg actcctgggg ccagggcacc    360
ctggtgaccg tgtcctcc                                                  378

<210> SEQ ID NO 7
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Gly Ser Ser Tyr Thr Phe Thr Asp Tyr
            20                  25                  30

Thr Met His Trp Val Arg Leu Ala Ser Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Gly Arg Ala Thr Ile Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Leu Val Thr Val Ser Ser
        115                 120                 125

<210> SEQ ID NO 8
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
caggtgcagc tggtgcagtc cggcgccgag gtgaagaagc ccggcgcctc cgtgaaggtg     60
tcctgcaagg gctcctccta caccttcacc gactacacca tgcactgggt gcgcctggcc    120
tccgccaaga ccctggagtg gatcggcgtg atcgacacct actacggcaa gaccaactac    180
```

```
aaccagaagt tcgagggccg cgccaccatc accgtggaca agtcctcctc caccgcctac    240
atggagctgt cctccctgcg ctccgaggac accgccgtgt actactgcgc ccgcggcggc    300
ttccgccgcg gcgaccgccc ctccctgcgc tacgccatgg actcctgggg ccagggcacc    360
ctggtgaccg tgtcctcc                                                 378
```

<210> SEQ ID NO 9
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 9

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Ile Ser
            20                  25                  30

Thr Tyr Ser Tyr Ile His Trp Phe Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Asn Ile His
65                  70                  75                  80

Pro Val Glu Glu Glu Asp Val Gly Ile Tyr Tyr Cys Gln His Ser Trp
                85                  90                  95

Glu Ile Pro Tyr Thr Phe Gly Gly Gly Thr Lys Val Glu Ile Lys
            100                 105                 110
```

<210> SEQ ID NO 10
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 10

```
gacatcgtgc tgacccagtc ccccgactcc ctggccgtgt ccctgggcga gagagccacc    60
atcaactgcc gcgcctccca gtccgtgtcc atctccacct actcctacat ccactggttc    120
cagcagaagc ccggccagcc ccccaagctg ctgatcaagt acgcctccaa cctggagtcc    180
ggcgtgcccg accgcttctc cggctccggc tccggcaccg acttcaccct gaacatccac    240
cccgtggagg aggaggacgt gggcatctac tactgccagc actcctggga gatcccctac    300
accttcggcg gcggcaccaa ggtggagatc aag                                333
```

<210> SEQ ID NO 11
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

```
<400> SEQUENCE: 11

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Ile Ser
            20                  25                  30

Thr Tyr Ser Tyr Ile His Trp Phe Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Glu Glu Asp Val Gly Ile Tyr Tyr Cys Gln His Ser Trp
                85                  90                  95

Glu Ile Pro Tyr Thr Phe Gly Gly Gly Thr Lys Val Glu Ile Lys
            100                 105                 110

<210> SEQ ID NO 12
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
gacatcgtgc tgacccagtc ccccgactcc ctggccgtgt ccctgggcga gagagccacc      60
atcaactgcc gcgcctccca gtccgtgtcc atctccacct actcctacat ccactggttc     120
cagcagaagc ccggccagcc ccccaagctg ctgatcaagt acgcctccaa cctggagtcc     180
ggcgtgcccg accgcttctc cggctccggc tccggcaccg acttcaccct gaagatctcc     240
cgcgtggagg aggaggacgt gggcatctac tactgccagc actcctggga gatcccctac     300
accttcggcg gcggcaccaa ggtggagatc aag                                  333

<210> SEQ ID NO 13
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Ile Ser
            20                  25                  30

Thr Tyr Ser Tyr Ile His Trp Phe Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Ile Tyr Tyr Cys Gln His Ser Trp
                85                  90                  95

Glu Ile Pro Tyr Thr Phe Gly Gly Gly Thr Lys Val Glu Ile Lys
            100                 105                 110
```

```
<210> SEQ ID NO 14
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
gacatcgtga tgacccagtc ccccgactcc ctggccgtgt ccctgggcga gagagccacc    60
atcaactgcc gcgcctccca gtccgtgtcc atctccacct actcctacat ccactggttc   120
cagcagaagc ccggccagcc ccccaagctg ctgatcaagt acgcctccaa cctggagtcc   180
ggcgtgcccg accgcttctc cggctccggc tccggcaccg acttcaccct gaagatctcc   240
cgcgtggagg ccgaggacgt gggcatctac tactgccagc actcctggga gatcccctac   300
accttcggcg gcggcaccaa ggtggagatc aag                                 333

<210> SEQ ID NO 15
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Tyr Thr Met His
1               5

<210> SEQ ID NO 16
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Val Ile Asp Thr Tyr Tyr Gly Lys Thr Asn Tyr Asn Gln Lys Phe Glu
1               5                   10                  15

Gly

<210> SEQ ID NO 17
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Gly Phe Arg Arg Gly Asp Arg Pro Ser Leu Arg Tyr Ala Met Asp
1               5                   10                  15

Ser

<210> SEQ ID NO 18
<211> LENGTH: 15
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 18

Arg Ala Ser Gln Ser Val Ser Ile Ser Thr Tyr Ser Tyr Ile His
1               5                   10                  15

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Tyr Ala Ser Asn Leu Glu Ser
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln His Ser Trp Glu Ile Pro Tyr Thr
1               5

<210> SEQ ID NO 21
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Phe Val Gln Ser Gly Pro Glu Leu Lys Lys Pro Gly Ala
1               5                   10                  15

Ser Val Lys Val Ser Cys Lys Gly Ser Ser Tyr Thr Phe Thr
            20                  25                  30

<210> SEQ ID NO 22
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Trp Val Lys Leu Ala His Ala Lys Thr Leu Glu Trp Ile Gly
1               5                   10

<210> SEQ ID NO 23
<211> LENGTH: 32
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 23

Arg Ala Thr Met Thr Val Asp Lys Ser Ser Thr Ala Tyr Met Glu
1               5                  10                  15

Leu Ala Arg Leu Arg Ser Glu Asp Ser Ala Val Tyr Tyr Cys Ala Arg
            20                  25                  30

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Trp Gly Gln Gly Thr Ser Val Thr Val Ser Ser
1               5                  10

<210> SEQ ID NO 25
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Gln Ser Gly Ala Glu Val Lys Lys Pro Gly Ala
1               5                  10                  15

Ser Val Lys Val Ser Cys Lys Gly Ser Ser Tyr Thr Phe Thr
            20                  25                  30

<210> SEQ ID NO 26
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Trp Val Lys Leu Ala Ser Ala Lys Thr Leu Glu Trp Ile Gly
1               5                  10

<210> SEQ ID NO 27
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Arg Ala Thr Met Thr Val Asp Lys Ser Ser Thr Ala Tyr Met Glu
1               5                  10                  15

Leu Ser Ser Leu Arg Ser Glu Asp Thr Ala Val Tyr Tyr Cys Ala Arg
            20                  25                  30
```

```
<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Trp Gly Gln Gly Thr Leu Val Thr Val Ser Ser
1               5                   10

<210> SEQ ID NO 29
<211> LENGTH: 788
<212> TYPE: PRT
<213> ORGANISM: Homo sapiens

<400> SEQUENCE: 29

Met Gly Ile Glu Leu Leu Cys Leu Phe Phe Leu Phe Leu Gly Arg Asn
1               5                   10                  15

Asp Ser Arg Thr Arg Trp Leu Cys Leu Gly Gly Ala Glu Thr Cys Glu
                20                  25                  30

Asp Cys Leu Leu Ile Gly Pro Gln Cys Ala Trp Cys Ala Gln Glu Asn
            35                  40                  45

Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Gly Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp Ser Lys Asn Glu Tyr Ser Met Ser
    290                 295                 300
```

```
Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
            325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
            355                 360                 365

Glu Glu Leu Arg Ser Glu Val Glu Leu Glu Val Leu Gly Asp Thr Glu
            370                 375                 380

Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
            405                 410                 415

Phe Ser Val Thr Val Asn Ile Pro His Cys Glu Arg Arg Ser Arg His
            420                 425                 430

Ile Ile Ile Lys Pro Val Gly Leu Gly Asp Ala Leu Glu Leu Leu Val
            435                 440                 445

Ser Pro Glu Cys Asn Cys Asp Cys Gln Lys Glu Val Glu Val Asn Ser
450                 455                 460

Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
            485                 490                 495

Leu Ser Thr Asp Ser Cys Lys Glu Ala Pro Asp His Pro Ser Cys Ser
            500                 505                 510

Gly Arg Gly Asp Cys Tyr Cys Gly Gln Cys Ile Cys His Leu Ser Pro
            515                 520                 525

Tyr Gly Asn Ile Tyr Gly Pro Tyr Cys Gln Cys Asp Asn Phe Ser Cys
            530                 535                 540

Val Arg His Lys Gly Leu Leu Cys Gly Gly Asn Gly Asp Cys Asp Cys
545                 550                 555                 560

Gly Glu Cys Val Cys Arg Ser Gly Trp Thr Gly Glu Tyr Cys Asn Cys
            565                 570                 575

Thr Thr Ser Thr Asp Ser Cys Val Ser Glu Asp Gly Val Leu Cys Ser
            580                 585                 590

Gly Arg Gly Asp Cys Val Cys Gly Lys Cys Val Cys Thr Asn Pro Gly
            595                 600                 605

Ala Ser Gly Pro Thr Cys Glu Arg Cys Pro Thr Cys Gly Asp Pro Cys
610                 615                 620

Asn Ser Lys Arg Ser Cys Ile Glu Cys His Leu Ser Ala Ala Gly Gln
625                 630                 635                 640

Ala Gly Glu Glu Cys Val Asp Lys Cys Lys Leu Ala Gly Ala Thr Ile
            645                 650                 655

Ser Glu Glu Glu Asp Phe Ser Lys Asp Gly Ser Val Ser Cys Ser Leu
            660                 665                 670

Gln Gly Glu Asn Glu Cys Leu Ile Thr Phe Leu Ile Thr Thr Asp Asn
            675                 680                 685

Glu Gly Lys Thr Ile Ile His Ser Ile Asn Glu Lys Asp Cys Pro Lys
            690                 695                 700

Pro Pro Asn Ile Pro Met Ile Met Leu Gly Val Ser Leu Ala Thr Leu
705                 710                 715                 720
```

```
Leu Ile Gly Val Val Leu Leu Cys Ile Trp Lys Leu Val Ser Phe
                725                 730                 735

His Asp Arg Lys Glu Val Ala Lys Phe Glu Ala Glu Arg Ser Lys Ala
            740                 745                 750

Lys Trp Gln Thr Gly Thr Asn Pro Leu Tyr Arg Gly Ser Thr Ser Thr
        755                 760                 765

Phe Lys Asn Val Thr Tyr Lys His Arg Glu Lys Gln Lys Val Asp Leu
    770                 775                 780

Ser Thr Asp Cys
785
```

<210> SEQ ID NO 30
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

```
Trp Val Arg Leu Ala Ser Ala Lys Thr Leu Glu Trp Ile Gly
1               5                   10
```

<210> SEQ ID NO 31
<211> LENGTH: 787
<212> TYPE: PRT
<213> ORGANISM: Mus musculus

<400> SEQUENCE: 31

```
Met Gly Ile Glu Leu Val Cys Leu Phe Leu Leu Leu Gly Arg Asn
1               5                   10                  15

Asp His Val Gln Gly Gly Cys Ala Trp Gly Gly Ala Glu Ser Cys Ser
            20                  25                  30

Asp Cys Leu Leu Thr Gly Pro His Cys Ala Trp Cys Ser Gln Glu Asn
        35                  40                  45

Phe Thr His Leu Ser Gly Ala Gly Glu Arg Cys Asp Thr Pro Ala Asn
    50                  55                  60

Leu Leu Ala Lys Gly Cys Gln Leu Pro Phe Ile Glu Asn Pro Val Ser
65                  70                  75                  80

Arg Ile Glu Val Leu Gln Asn Lys Pro Leu Ser Val Gly Arg Gln Lys
                85                  90                  95

Asn Ser Ser Asp Ile Val Gln Ile Ala Pro Gln Ser Leu Val Leu Lys
            100                 105                 110

Leu Arg Pro Gly Arg Glu Gln Thr Leu Gln Val Gln Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Arg Leu Ala
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Met Lys Thr Thr Pro Glu Glu
            180                 185                 190

Ile Thr Asn Pro Cys Ser Ser Ile Pro Tyr Phe Cys Leu Pro Thr Phe
        195                 200                 205

Gly Phe Lys His Ile Leu Pro Leu Thr Asp Asp Ala Glu Arg Phe Asn
    210                 215                 220
```

-continued

```
Glu Ile Val Arg Lys Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp His Arg Asn Glu Tyr Ser Met Ser
290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
        355                 360                 365

Glu Glu Leu Arg Ser Glu Val Glu Leu Glu Val Leu Gly Asp Thr Glu
370                 375                 380

Gly Leu Asn Leu Ser Phe Thr Ala Leu Cys Asn Asn Gly Val Leu Phe
385                 390                 395                 400

Pro His Gln Lys Lys Cys Ser His Met Lys Val Gly Asp Thr Ala Ser
                405                 410                 415

Phe Asn Val Thr Val Ser Val Ser Asn Cys Glu Lys Arg Ser Arg Asn
            420                 425                 430

Leu Ile Ile Lys Pro Val Gly Leu Gly Asp Thr Leu Glu Ile Leu Val
        435                 440                 445

Ser Ala Glu Cys Asp Cys Asp Cys Gln Arg Glu Ile Glu Thr Asn Ser
450                 455                 460

Ser Lys Cys His Asn Gly Asn Gly Ser Phe Gln Cys Gly Val Cys Thr
465                 470                 475                 480

Cys Asn Pro Gly His Met Gly Pro His Cys Glu Cys Gly Glu Asp Met
                485                 490                 495

Val Ser Thr Asp Ser Cys Lys Glu Ser Pro Gly His Pro Ser Cys Ser
            500                 505                 510

Gly Arg Gly Asp Cys Tyr Cys Gly Gln Cys Ile Cys His Leu Ser Pro
        515                 520                 525

Tyr Gly Ser Ile Tyr Gly Pro Tyr Cys Gln Cys Asp Asn Phe Ser Cys
530                 535                 540

Leu Arg His Lys Gly Leu Leu Cys Gly Asp Asn Gly Asp Cys Asp Cys
545                 550                 555                 560

Gly Glu Cys Val Cys Arg Asp Gly Trp Thr Gly Glu Tyr Cys Asn Cys
                565                 570                 575

Thr Thr Asn Arg Asp Ser Cys Thr Ser Glu Asp Gly Val Leu Cys Ser
            580                 585                 590

Gly Arg Gly Asp Cys Val Cys Gly Lys Cys Val Cys Arg Asn Pro Gly
        595                 600                 605

Ala Ser Gly Pro Thr Cys Glu Arg Cys Pro Thr Cys Gly Asp Pro Cys
610                 615                 620

Asn Ser Lys Arg Ser Cys Ile Glu Cys Tyr Leu Ser Ala Asp Gly Gln
625                 630                 635                 640
```

```
Ala Gln Glu Glu Cys Ala Asp Lys Cys Lys Ala Ile Gly Ala Thr Ile
                645                 650                 655

Ser Glu Glu Asp Phe Ser Lys Asp Thr Ser Val Ser Cys Ser Leu Gln
            660                 665                 670

Gly Glu Asn Glu Cys Leu Ile Thr Phe Leu Ile Thr Thr Asp Asn Glu
            675                 680                 685

Gly Lys Thr Ile Ile His Asn Ile Asn Glu Lys Asp Cys Pro Lys Pro
        690                 695                 700

Pro Asn Ile Pro Met Ile Met Leu Gly Val Ser Leu Ala Ile Leu Leu
705                 710                 715                 720

Ile Gly Val Val Leu Leu Cys Ile Trp Lys Leu Leu Val Ser Phe His
                725                 730                 735

Asp Arg Lys Glu Val Ala Lys Phe Glu Ala Glu Arg Ser Lys Ala Lys
            740                 745                 750

Trp Gln Thr Gly Thr Asn Pro Leu Tyr Arg Gly Ser Thr Ser Thr Phe
            755                 760                 765

Lys Asn Val Thr Tyr Lys His Arg Glu Lys His Lys Ala Gly Leu Ser
        770                 775                 780

Ser Asp Gly
785

<210> SEQ ID NO 32
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Gly Gly Ser
1

<210> SEQ ID NO 33
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Gly Gly Gly
1

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Gly Gly Gly Ser
1               5
```

<210> SEQ ID NO 35
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

Arg Ala Thr Ile Thr Val Asp Lys Ser Ser Thr Ala Tyr Met Glu
1               5                   10                  15
Leu Ser Ser Leu Arg Ser Glu Asp Thr Ala Val Tyr Tyr Cys Ala Arg
            20                  25                  30

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Ser Gly Gly Gly Gly
1               5

<210> SEQ ID NO 37
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Asp Ile Val Leu Thr Gln Ser Pro Asp Ser Leu Ala Val Ser Leu Gly
1               5                   10                  15
Glu Arg Ala Thr Ile Asn Cys
            20

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Trp Phe Gln Gln Lys Pro Gly Gln Pro Pro Lys Leu Leu Ile Lys
1               5                   10                  15

<210> SEQ ID NO 39
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

Gly Val Pro Asp Arg Phe Ser Gly Ser Gly Ser Gly Thr Asp Phe Thr
1               5                   10                  15

Leu Asn Ile His Pro Val Glu Glu Glu Asp Val Gly Ile Tyr Tyr Cys
            20                  25                  30

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Phe Gly Gly Gly Thr Lys Val Glu Ile Lys
1               5                   10

<210> SEQ ID NO 41
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Gly Gly Gly Gly Ser
1               5

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Gly Gly Gly Gly Gly
1               5

<210> SEQ ID NO 43
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gly Val Pro Asp Arg Phe Ser Gly Ser Gly Ser Gly Thr Asp Phe Thr
1               5                   10                  15

Leu Lys Ile Ser Arg Val Glu Glu Glu Asp Val Gly Ile Tyr Tyr Cys
            20                  25                  30

<210> SEQ ID NO 44
<211> LENGTH: 7
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 44

Gly Gly Gly Gly Gly Gly Ser
1               5

<210> SEQ ID NO 45
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ser Gly Gly Gly Gly Gly Gly
1               5

<210> SEQ ID NO 47
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Ile Tyr Tyr Cys
            20                  25                  30

<210> SEQ ID NO 48
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Val Gln Phe Gln Gln Ser Gly Pro Glu Leu Val Arg Pro Gly Val
1               5                   10                  15

Ser Val Lys Leu Ser Cys Lys Gly Ser Ser Tyr Thr Phe Thr Asp Tyr
            20                  25                  30
```

```
Thr Met His Trp Val Lys Leu Ser His Ala Lys Thr Leu Glu Trp Ile
            35                  40                  45

Gly Val Ile Asp Thr Tyr Tyr Gly Lys Thr Asn Tyr Asn Gln Lys Phe
 50                  55                  60

Glu Gly Lys Ala Thr Met Thr Val Asp Lys Ser Ser Thr Ala Tyr
65                   70                  75                  80

Met Asp Leu Ala Arg Leu Thr Ser Glu Asp Ser Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Ser Val Thr Val Ser Ser
            115                 120                 125
```

<210> SEQ ID NO 49
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Ile Ser
            20                  25                  30

Thr Tyr Ser Tyr Ile His Trp Phe Gln Gln Lys Pro Gly Gln Pro Pro
            35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
65                   70                  75                  80

Pro Val Glu Glu Glu Asp Thr Ala Ile Tyr Tyr Cys Gln His Ser Trp
                85                  90                  95

Glu Ile Pro Tyr Thr Phe Gly Gly Gly Thr Lys Val Glu Ile Lys
            100                 105                 110
```

<210> SEQ ID NO 50
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

```
Gln Val Gln Phe Val Gln Ser Gly Pro Glu Leu Lys Lys Pro Gly Ala
1               5                   10                  15

Ser Val Lys Leu Ser Cys Lys Gly Ser Ser Tyr Thr Phe Thr Asp Tyr
            20                  25                  30

Thr Met His Trp Val Lys Leu Ala His Ala Lys Thr Leu Glu Trp Ile
            35                  40                  45

Gly Val Ile Asp Thr Tyr Tyr Gly Lys Thr Asn Tyr Asn Gln Lys Phe
 50                  55                  60

Glu Gly Arg Ala Thr Met Thr Val Asp Lys Ser Ser Thr Ala Tyr
65                   70                  75                  80
```

```
Met Glu Leu Ala Arg Leu Thr Ser Glu Asp Ser Ala Val Tyr Tyr Cys
            85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Ser Val Thr Val Ser Ser
        115                 120                 125

<210> SEQ ID NO 51
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
caggtgcagt tcgtgcagtc cggccccgag ctgaagaagc ccggcgcctc cgtgaagctg      60
tcctgcaagg gctcctccta caccttcacc gactacacca tgcactgggt gaagctggcc    120
cacgccaaga ccctggagtg gatcggcgtg atcgacacct actacggcaa gaccaactac    180
aaccagaagt tcgagggccg cgccaccatg accgtggaca gtcctcctc caccgcctac    240 atggagacgg cccgcctgcg ctccgaggac tccgccgtgt actactgcgc ccgcggcggc    300
ttccgccgcg gcgaccgccc ctccctgcgc tacgccatgg actcctgggg ccagggcacc    360
tccgtgaccg tgtcctcc                                                  378

<210> SEQ ID NO 52
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gln Val Gln Phe Val Gln Ser Gly Pro Glu Leu Lys Lys Pro Gly Ala
1               5                   10                  15

Ser Val Lys Leu Ser Cys Lys Gly Ser Ser Tyr Thr Phe Thr Asp Tyr
            20                  25                  30

Thr Met His Trp Val Lys Leu Ala His Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Gly Lys Ala Thr Met Thr Val Asp Lys Ser Ser Ser Thr Ala Tyr
65                  70                  75                  80

Met Asp Leu Ala Arg Leu Thr Ser Glu Asp Ser Ala Val Tyr Tyr Cys
            85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Ser Val Thr Val Ser Ser
        115                 120                 125

<210> SEQ ID NO 53
<211> LENGTH: 378
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 53
caggtgcagt tcgtgcagtc cggccccgag ctgaagaagc ccggcgcctc cgtgaagctg    60
tcctgcaagg gctcctccta caccttcacc gactacacca tgcactgggt gaagctggcc   120
cacgccaaga ccctggagtg gatcggcgtg atcgacacct actacggcaa gaccaactac   180
aaccagaagt tcgagaaacg cgccaccatg accgtggaca gtcctcctc caccgcctac   240 gacgagacgg cccgcctgcg ctccgaggac tccgccgtgt actactgcgc ccgcggcggc   300
ttccgccgcg gcgaccgccc ctccctgcgc tacgccatgg actcctgggg ccagggcacc   360
tccgtgaccg tgtcctcc                                                  378

<210> SEQ ID NO 54
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Phe Val Gln Ser Gly Pro Glu Leu Lys Lys Pro Gly Ala
1               5                   10                  15

Ser Val Lys Leu Ser Cys Lys Gly Ser Ser Tyr Thr Phe Thr
            20                  25                  30

<210> SEQ ID NO 55
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Arg Ala Thr Met Thr Val Asp Lys Ser Ser Ser Thr Ala Tyr Met Glu
1               5                   10                  15

Leu Ala Arg Leu Thr Ser Glu Asp Ser Ala Val Tyr Tyr Cys Ala Arg
            20                  25                  30

<210> SEQ ID NO 56
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Lys Ala Thr Met Thr Val Asp Lys Ser Ser Ser Thr Ala Tyr Met Asp
1               5                   10                  15

Leu Ala Arg Leu Thr Ser Glu Asp Ser Ala Val Tyr Tyr Cys Ala Arg
            20                  25                  30

```
<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Tyr Thr Phe Thr Asp Tyr
1               5

<210> SEQ ID NO 58
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Asp Thr Tyr Tyr Gly Lys
1               5

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ser Tyr Thr Phe Thr Asp Tyr Thr Met His
1               5                   10

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Val Ile Asp Thr Tyr Tyr Gly Lys Thr Asn
1               5                   10

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Thr Asp Tyr Thr Met His
1               5

<210> SEQ ID NO 62
<211> LENGTH: 13
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 62

Trp Ile Gly Val Ile Asp Thr Tyr Tyr Gly Lys Thr Asn
1               5                   10

<210> SEQ ID NO 63
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ala Arg Gly Gly Phe Arg Arg Gly Asp Arg Pro Ser Leu Arg Tyr Ala
1               5                   10                  15

Met Asp

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ser Ile Ser Thr Tyr Ser Tyr Ile His Trp Phe
1               5                   10

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Leu Leu Ile Lys Tyr Ala Ser Asn Leu Glu
1               5                   10

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gln His Ser Trp Glu Ile Pro Tyr
1               5

<210> SEQ ID NO 67
<211> LENGTH: 126
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 67

```
Gln Val Gln Phe Val Gln Ser Gly Pro Glu Leu Lys Lys Pro Gly Ala
1               5                   10                  15

Ser Val Lys Leu Ser Cys Lys Gly Ser Ser Tyr Thr Phe Thr Asp Tyr
            20                  25                  30

Thr Met His Trp Val Lys Leu Ala His Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Gly Arg Ala Thr Met Thr Val Asp Lys Ser Ser Ser Thr Ala Tyr
65                  70                  75                  80

Met Glu Thr Ala Arg Leu Arg Ser Glu Asp Ser Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Ser Val Thr Val Ser Ser
            115                 120                 125
```

<210> SEQ ID NO 68
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

```
Gln Val Gln Phe Val Gln Ser Gly Pro Glu Leu Lys Lys Pro Gly Ala
1               5                   10                  15

Ser Val Lys Leu Ser Cys Lys Gly Ser Ser Tyr Thr Phe Thr Asp Tyr
            20                  25                  30

Thr Met His Trp Val Lys Leu Ala His Ala Lys Thr Leu Glu Trp Ile
        35                  40                  45

Gly Val Ile Asp Thr Tyr Tyr Gly Lys Thr Asn Tyr Asn Gln Lys Phe
    50                  55                  60

Glu Lys Arg Ala Thr Met Thr Val Asp Lys Ser Ser Ser Thr Ala Tyr
65                  70                  75                  80

Asp Glu Thr Ala Arg Leu Arg Ser Glu Asp Ser Ala Val Tyr Tyr Cys
                85                  90                  95

Ala Arg Gly Gly Phe Arg Arg Gly Asp Arg Pro Ser Leu Arg Tyr Ala
            100                 105                 110

Met Asp Ser Trp Gly Gln Gly Thr Ser Val Thr Val Ser Ser
            115                 120                 125
```